US012780759B2

(12) United States Patent
Kinsho et al.

(10) Patent No.: US 12,780,759 B2

(45) Date of Patent: Nov. 3, 2026

(54) PROCESS FOR PREPARING ALPHA-FARNESENES AND 4-SUBSTITUTED 3-METHYL-1,3-BUTADIENE COMPOUND HAVING RELATED STRUCTURE, AND SYNTHETIC INTERMEDIATE COMPOUND THEREOF

(71) Applicant: Shin-Etsu Chemical Co., Ltd., Tokyo (JP)

(72) Inventors: Takeshi Kinsho, Joetsu (JP); Yusuke Nagae, Joetsu (JP); Akihiro Baba, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 135 days.

(21) Appl. No.: 19/019,790

(22) Filed: Jan. 14, 2025

(65) Prior Publication Data

US 2025/0230109 A1 Jul. 17, 2025

(30) Foreign Application Priority Data

Jan. 16, 2024 (JP) ................................ 2024-004371

(51) Int. Cl.
*C07C 1/32* (2006.01)

(52) U.S. Cl.
CPC .................................. *C07C 1/322* (2013.01)

(58) Field of Classification Search
CPC ....... C07C 4/00; C07C 2531/02; C07C 1/322; C07C 21/215; C07C 22/04; C07C 315/00; C07C 317/14; C07C 2531/12; C07C 2531/14; C07C 2531/24; C07C 1/30; C07C 17/361
See application file for complete search history.

(56) References Cited

U.S. PATENT DOCUMENTS 3,848,000 A 11/1974 Menet et al.
2006/0052643 A1 3/2006 Prakash et al.

OTHER PUBLICATIONS

Extended European Search Report corresponding to European Patent Application No. 25150406.4 (7 pages) (dated Jun. 17, 2025).
Alpoim, et al., "Ring opening reactions of vinyl cyclopropanes with para toluene sulphonyl iodide", Tetrahedron Letters, 29(33):4173-4176 (1988).
Philippe, et al., "Two new convenient syntheses of 14C-squalene from turbinaric acid", Journal of Labelled Compounds and Radiopharmaceuticals, 61:878-884 (2018).
Anet, E. F. L. J. , "Synthesis of (E,Z)-α-,(Z,Z)-α-, and (Z)-β-farnesene", Australian Journal of Chemistry, 23 (10):2101-2108 (1970).
Baeckstrom , et al., "A Synthesis of Trans-β-Farnesene from Myrcene which Includes a Modified Work up Method for DIBAH Reductions of Esters to Aldehydes", Synthetic Communications, 20(3):423-429 (1990).
Brieger , et al., "The Synthesis of trans, trans-α-Farnesene", The Journal of Organic Chemistry, 34(12):3789-3791 (1969).
Kang, et al., "A Convenient Synthesis of (E)-β-Farnesene", Bulletin of the Korean Chemical Society, 8(4):351-353 (1987).
Kang , et al., "A Practical Synthesis of (E)-β-Farnesene, the Alarm Pheromone of Aphids", Bulletin of the Korean Chemical Society, 7(2):157-158 (1986).
Kawashima , et al., "Highly Regio- and Stereoselective Ring-Opening Reaction of γ-Alkenyl-γ-butyrolactones with Allylsilanes in the Presence of Trimethyloxonium Salt Leading to Methyl 4,8-Alkadienoates", Bulletin of the Chemical Society of Japan, 61(11):4051-4055 (1988).
Knight , et al., "(Z,E)-α-farnesene: Major component of secretion from metathoracic scent gland of cotton seed bug, *Oxycarenus hyalinipennis* (Costa) (Heteroptera; Lygaeidae)", Journal of Chemical Ecology, 10:641-649 (1984).
Mandai , et al., "Highly Stereoselective Total Syntheses of β-Farnesene, β-Sinensal, and Dendrolasin Employing 2-(Hydroxymethyl)-4-(phenylthio)-1-butene as a Building Block", The Journal of Organic Chemistry, 48(26):5183-5185 (1983).
(Continued)

*Primary Examiner* — Ali Z Fadhel
(74) *Attorney, Agent, or Firm* — Myers Bigel, P.A.

(57) ABSTRACT

The present invention provides a process for preparing a 4-substituted 3-methyl-1,3-butadiene compound of the following general formula (A), wherein R represents a linear, branched, or cyclic hydrocarbon group having 1 to 20 carbon atoms and optionally having an unsaturated bond(s), the process comprising steps of subjecting a primary allylsulfone compound of the following general formula (D), wherein R represents a linear, branched, or cyclic hydrocarbon group having 1 to 20 carbon atoms and optionally having an unsaturated bond(s), X represents a halogen atom, and W represents an arenesulfonyl group, to a reductive removal of the arenesulfonyl group, W, to form a halide compound of the following general formula (B), wherein R represents a linear, branched, or cyclic hydrocarbon group having 1 to 20 carbon atoms and optionally having an unsaturated bond(s), and X represents a halogen atom; and subjecting the aforesaid halide compound (B) to an elimination reaction of a hydrogen halide, HX, to form the aforesaid 4-substituted 3-methyl-1,3-butadiene compound (A).

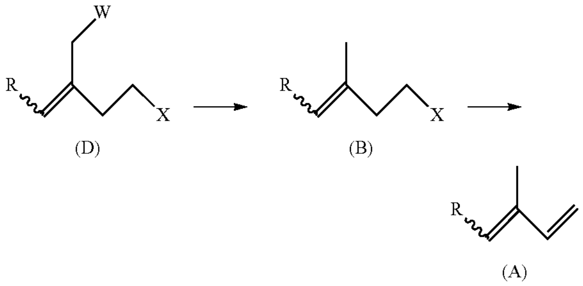

5 Claims, No Drawings

(56) References Cited

OTHER PUBLICATIONS

Mimura , et al., "Synthetic Utility of Allylic Thiolcarbamates. Stereoselective Synthesis of Simple Natural Products Including Optically Active Manicone and β-Sinensal", Chemistry Letters, 8(11):1361-1364 (1979).

Morgan , et al., "Synthesis of (Z,E)- and (Z,Z)-α-farnesenes and -homofarnesenes", Journal of the Chemical Society, Perkin Transactions 1, pp. 399-404 (1985).

Poppe , et al., "A Convenient Synthesis of (E)-β-Farnesene", Synthetic Communications, 17(2):173-179 (1987).

Ramaiah , et al., "A Short Synthesis of (3Z,6E)-α-Farnesene", The Journal of Organic Chemistry, 60:6211-6213 (1995).

Suckling , et al., "Trail Pheromone Disruption of Red Imported Fire Ant", Journal of Chemical Ecology, 36 (7):744-750 (2010).

Tanaka, et al., "A General Method for the Synthesis of 1,3-dienes. Simple Synthesis of β- and trans-α-Farnesene from Farnesol", Journal of the American Chemical Society, 97(11):3252-3254 (1975).

Vander Meer , et al., "Hydrocarbon components of the trail pheromone of the red imported fire ant, Solenopsis invicta", Tetrahedron Letters, 22(18):1651-1654 (1981).

Veselovskii , et al., "Regiospecific ene reaction of benzenesulfonyl chloride with linear isoprenoids", Organic Chemistry, 36:2583-2586 (1987).

Corey, et al., "Simple synthesis of (+/−)-beta-trans-bergamotene", Tetrahedron Letters, 26(30):3535-3538 (1985).

PROCESS FOR PREPARING ALPHA-FARNESENES AND 4-SUBSTITUTED 3-METHYL-1,3-BUTADIENE COMPOUND HAVING RELATED STRUCTURE, AND SYNTHETIC INTERMEDIATE COMPOUND THEREOF

TECHNICAL FIELD

The present invention relates to a process for preparing α-farnesenes, which are sesquiterpenes useful as fragrances and flavors, or as biologically active substances against insects and the like, and 4-substituted 3-methyl-1,3-butadiene compounds having related structures. The present invention also relates to useful synthetic intermediate compounds thereof.

BACKGROUND ART

Farnesenes, which are known for a long time terpene compounds, have alpha and beta forms, differing by the positions of double bonds. α-Farnesene has four geometric isomers with trisubstituted double bonds at positions 3 and 6, and β-farnesene has two geometric isomers with a trisubstituted double bond at position 6:

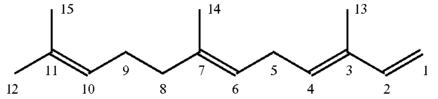

(3E,6E)-α-farnesene

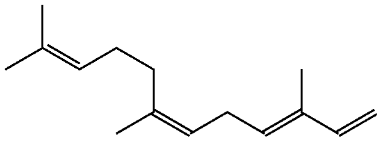

(3E,6Z)-α-farnesene

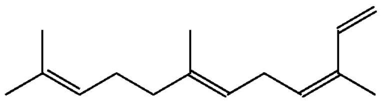

(3Z,6E)-α-farnesene

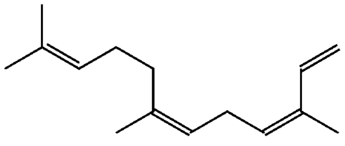

(3Z,6Z)-α-farnesene

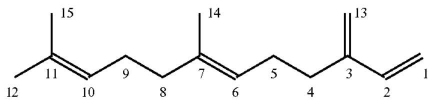

(E)-β-farnesene

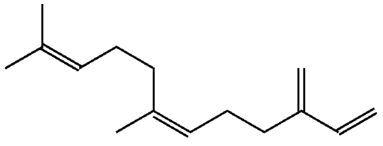

(Z)-β-farnesene wherein the numerals represent carbon positions.

Among farnesenes, α-farnesene has been identified in many plants, such as apples, pears, *Chrysanthemum, Perilla*, and *Achillea*. (3E,6E)-α-Farnesene is abundant in the skin of apple fruit, a natural source of this compound, and gives off a green apple odor. (3Z,6E)-α-Farnesene is found in essential oils of plants, such as *Perilla* and *Gardenia*. α-Farnesene also is found in extracts of many insects including several ants and the cotton seed bug, *Oxycarenus hyalinipennis*, and diverse biological activity has been reported. Examples include a trail pheromone of the hymenopteran, red imported fire ant, *Solenopsis invicta*; an alarm pheromone of the isopteran, termite; aggregation pheromones of the dipterans, Caribbean fruit fly and Mediterranean fruit fly; and an attractant of the lepidopteran, codling moth. β-Farnesene is a component of essential oils of various plants, and is known to have alarm pheromone activity against the hemipteran, aphid. These naturally-occurring and synthetic farnesenes also are used as fragrances and flavors as applications of biological activity of the human sense of smell.

α-Farnesenes are characterized by a 4-substituted 3-methyl-1,3-butadiene structure of the following general formula:

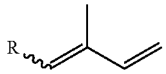

4-substituted 3-methyl-1,3-butadiene wherein the substituent group R represents a linear, branched, or cyclic hydrocarbon group having 1 to 20 carbon atoms and optionally having an unsaturated bond(s), and the wavy line represents a bond without a specific geometrical isomerism.

α-Farnesenes correspond to when the substituent group R of the aforesaid general formula is a (E)- or (Z)-3,7-dimethyl-2,6-octadienyl group. Other important related compounds having this characteristic structure also are known. Known examples of related compounds include corresponding monoterpenes, α-ocimene and β-ocimene, corresponding respectively to when the substituent group R in the aforesaid general formula is a 3-methyl-3-butenyl group and a 3-methyl-2-butenyl group. α- and β-ocimene each have two geometric isomers of trisubstituted double bonds. Ocimenes are found in various plants and fruits, and are commonly present in nature as isomeric mixtures. Isomers, both alone and in mixtures, are oily substances with pleasant fragrances for humans, and are used as fragrances and flavors, such as perfumes.

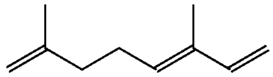

(E)-α-ocimene

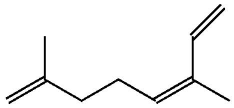

(Z)-α-ocimene

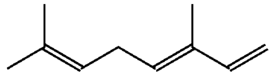

(E)-β-ocimene

-continued

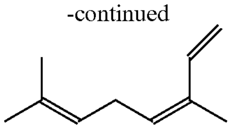

(Z)-β-ocimene

PRIOR ART

Non-Patent Literatures

[Non-Patent Literature 1]R. K. Vander Meer et al., Tetrahedron Lett., 1981, 22, 1651.

[Non-Patent Literature 2]D. W. Knight et al., J. Chem. Ecol., 1984, 10, 641.

[Non-Patent Literature 3]E. F. Anet et al., Aust. J. Chem., 1970, 23, 2101.

[Non-Patent Literature 4]G. Brieger et al., J. Org. Chem., 1969, 34, 3789.

[Non-Patent Literature 5]H. Yamamoto et al., J. Am. Chem. Soc., 1975, 97, 3252.

[Non-Patent Literature 6]E. D. Morgan et al., J. Chem. Soc. Perkin Trans. 1, 1985, 399.

[Non-Patent Literature 7]J. G. Millar et al., J. Org. Chem., 1995, 60, 6211.

[Non-Patent Literature 8]D. M. Suckling et al., J. Chem. Ecol., 2010, 36, 744.

OBJECT OF THE INVENTION

The economic synthesis and preparation of such farnesenes and their related derivatives are necessary for basic and applied research, and/or practical use. Isomers that occur naturally in large amounts may be sold inexpensively, while unnatural isomers that do not occur in nature are supplied by synthesis. Various other isomers may be obtained by the isomerization of natural products, but such isomers are typically complex isomeric mixtures, making it quite difficult to isolate and improve the purity of a specific isomer. To meet the needs of, for example, basic research such as comparative studies of isomer activity and correlation studies of the activity of derivatives with partially modified structures, it is desirable to selectively synthesize isomers by position and geometrical isomerism of the double bonds, and to have a higher degree of freedom for derivative synthesis by substituting substituent groups. Large amounts need to be synthesized for applications and practical use of pheromone activity for pest forecasting and pest control of organisms, such as insects, and for fragrances and flavors using the fragrance activity of humans, and it is desirable for the synthesis efficiency to be high enough to scale up for industrial purposes. Some applications and practical uses may not always require a pure isomer, and it may be economically advantageous to use a mixture of active isomers. For such purposes, there has been a high demand for a process applicable to both basic and applied research for efficiently preparing farnesenes and their related derivatives.

Various processes for synthesizing α-farnesenes are known. However, many known processes yield complex mixtures, from which pure compounds are isolated and purified with considerable difficulty. Non-Patent Literature 1, for example, describes dehydrating nerolidol to obtain α- and β-farnesene isomer mixtures, of which isomers were separated by Florisil chromatography. Non-Patent Literatures 2 and 3 used raw materials, nerolidol and farnesol, to form farnesene isomer mixtures, along with their isomers including cyclization products, and triterpenes by polymerization (dimerization); and isomer isolation was carried out by gas chromatography. Non-Patent Literature 2 describes a process of isomer separation by conversion to a Diels-Alder adduct with maleic anhydride for removal. A rhodium catalyzed isomerization reaction of β-farnesene in Non-Patent Literature 4 yields a similarly complex mixture. Non-Patent Literature 5 reports synthesis from farnesol via 3-ene-1,2-diol. Non-Patent Literature 6 reports synthesis of (Z, E)- and (Z, Z)-farnesene using a Wittig reaction, with separation by silver nitrate-silica gel column chromatography. Non-Patent Literature 7 describes a Synthetic Example in which diastereomers formed with Horner-type Wittig skeleton formation are separated by high performance liquid chromatography (HPLC) followed by diphenylphosphinic acid elimination with a base, and pure (E, Z)-α-farnesene is synthesized by removing a coexisting (E, E)-isomer by conversion to a Diels-Alder adduct with tetracyanoethylene. Non-Patent Literature 8 reports the extraction of (E, E)-α-farnesene from apples, followed by photoisomerization to form a mixture of (Z, E)- and (E, E)-α-farnesene, of which the (E, E)-isomer was reduced by the aforesaid conversion to a Diels-Alder adduct to obtain (Z, E)-α-farnesene [(Z, E):(E, E)=91:9], which was used in trail pheromone disruption of the red imported fire ant. It is reported that this technique formed 115 mg of the active agent, (Z, E)-α-farnesene, from 60 kg of apples. However, stability of intermediates is a major problem for industrial-scale preparation when such synthesis is carried out from a raw material having a conjugated diene structure that is unstable thermally and in the presence of acids, or by forming a conjugated diene structure in intermediates in the initial stages of synthesis. Furthermore, synthesis from natural products as starting materials is limited to specific raw materials that are available, and various derivatives with modified structures are not easy to synthesize. In particular, various derivatives with modified structures cannot be synthesized from natural starting materials, such as farnesol, in which a carbon framework (number of carbons and their connectivity) has already been determined.

Thus, the known synthesizing processes of α-farnesene have many problems, and there has been a great need for an efficient process for preparing α-farnesenes and their related derivatives to avoid these problems.

SUMMARY OF THE INVENTION

As a result of intensive research in view of the aforesaid circumstances, it was found that a primary allylsulfone compound, that will be explained below, could be designed as a reasonable synthetic intermediate and used as a synthetic route to selectively and efficiently prepare α-farnesenes and related 4-substituted 3-methyl-1,3-butadiene compounds, thus completing the present invention. The preparation process according to the present invention may be industrially advantageous as well.

According to an aspect of the present invention, there is provided a process for preparing a 4-substituted 3-methyl-1,3-butadiene compound of the following general formula (A):

(A)

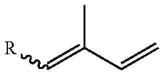

wherein R represents a linear, branched, or cyclic hydrocarbon group having 1 to 20 carbon atoms and optionally having an unsaturated bond(s), the process comprising the steps of:

subjecting a primary allylsulfone compound of the following general formula (D):

(D)

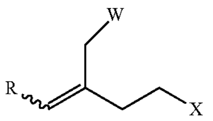

wherein R represents a linear, branched, or cyclic hydrocarbon group having 1 to 20 carbon atoms and optionally having an unsaturated bond(s), X represents a halogen atom, and W represents an arenesulfonyl group, to a reductive removal of the arenesulfonyl group, W, to form a halide compound of the following general formula (B):

(B)

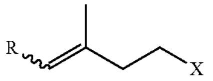

wherein R represents a linear, branched, or cyclic hydrocarbon group having 1 to 20 carbon atoms and optionally having an unsaturated bond(s), and X represents a halogen atom; and subjecting the aforesaid halide compound (B) to an elimination reaction of the hydrogen halide, HX, to form the aforesaid 4-substituted 3-methyl-1,3-butadiene compound (A).

According to another aspect of the present invention, there is provided a primary allylsulfone compound of the following general formula (D):

(D)

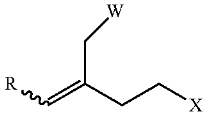

wherein R represents a linear, branched, or cyclic hydrocarbon group having 1 to 20 carbon atoms and optionally having an unsaturated bond(s), X represents a halogen atom, and W represents an arenesulfonyl group.

According to another aspect of the present invention, there is provided a process for preparing a primary allylsulfone compound of the following general formula (D):

(D)

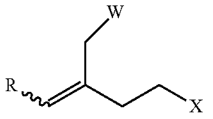

wherein R represents a linear, branched, or cyclic hydrocarbon group having 1 to 20 carbon atoms and optionally having an unsaturated bond(s), X represents a halogen atom, and W represents an arenesulfonyl group, the process comprising a step of:

subjecting a secondary allylsulfone compound of the following general formula (E):

(E)

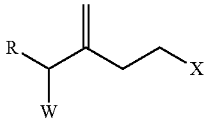

wherein R represents a linear, branched, or cyclic hydrocarbon group having 1 to 20 carbon atoms and optionally having an unsaturated bond(s), X represents a halogen atom, and W represents an arenesulfonyl group, to an allylic rearrangement reaction of the arenesulfonyl group, W, to form the aforesaid primary allylsulfone compound (D).

According to another aspect of the present invention, there is provided a secondary allylsulfone compound of the following general formula (E):

(E)

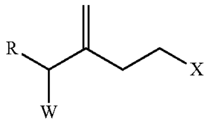

wherein R represents a linear, branched, or cyclic hydrocarbon group having 1 to 20 carbon atoms and optionally having an unsaturated bond(s), X represents a halogen atom, and W represents an arenesulfonyl group.

According to another aspect of the present invention, there is provided a halide compound of the following general formula (B'):

(B')

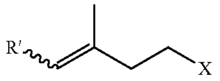

wherein R' represents a 3,7-dimethyl-2,6-octadienyl group or a 3-methyl-2-butenyl group, and X represents a halogen atom.

According to the present invention, α-farnesenes and 4-substituted 3-methyl-1,3-butadiene compounds having related structures may be selectively and efficiently prepared.

DETAILED DESCRIPTION OF THE INVENTION

Embodiments of the present invention will be explained below in detail. It should be understood that the present invention is not limited to or by the following embodiments.

Structures of intermediates, reagents, and target compounds represented by chemical formulae in the present specification may sometimes comprise stereoisomers, such as enantiomers or diastereomers. Unless otherwise stated, the chemical formulae shall be interpreted to represent all of these isomers. The isomers may be used alone or in combination at any ratio. A 50:50 mixture of two enantiomers is a racemic mixture, and a mixture containing two enantiomers at a non-equivalent ratio is a scalemic mixture. Either a racemic mixture or a scalemic mixture may be used.

The present inventors have investigated, according to a synthetic plan explained below, a process for preparing α-farnesenes and a related 4-substituted 3-methyl-1,3-butadiene compound (A):

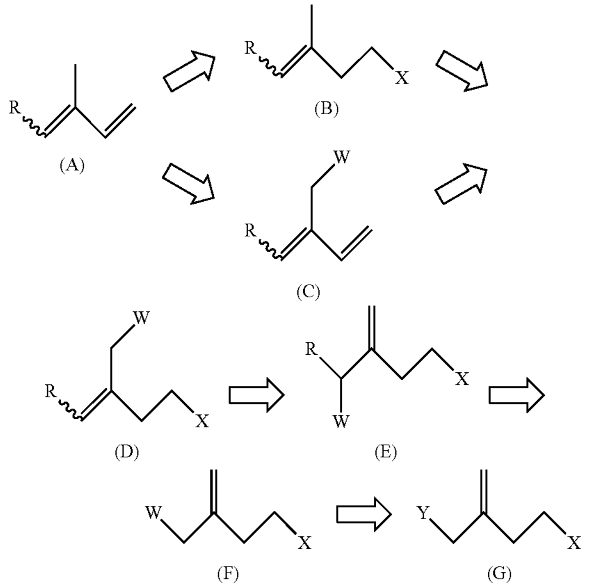

(A) (B) (C) (D) (E) (F) (G)

wherein the white arrows represent transformations in retrosynthetic analysis, R represents a linear, branched, or cyclic hydrocarbon group optionally having an unsaturated bond(s), X and Y represent, independently of each other, a halogen atom, and W represents an arenesulfonyl group.

In the aforesaid synthesis plan, the case where the hydrocarbon group R, which is the substituent group at position 4, is a 3,7-dimethyl-2,6-octadienyl group corresponds to α-farnesene.

A primary allylsulfone compound (D), 4-substituted 3-arenesulfonylmethyl-1-halo-3-butene compound, was designed as a key synthetic intermediate. The primary allylsulfone compound (D) is subjected to a reductive removal of the arenesulfonyl group, W, of the allyl position of the primary allylsulfone compound (D) (i.e., desulfonation) (or a reductive cleavage of the arenesulfonyl group, W, of the allyl position from the primary allylsulfone compound (D)) to form a halide compound (B), and then the halide compound (B) is subjected to an elimination reaction of the hydrogen halide, HX, of the halide compound (B) to obtain a 4-substituted 3-methyl-1,3-butadiene compound (A). Alternatively, by interchanging the order of converting the functional groups, the hydrogen halide, HX, is eliminated from the primary allylsulfone compound (D), and then the primary allylsulfone compound (D) is subjected to form a primary allylsulfonediene compound (C), and then the primary allylsulfonediene compound (C) is subjected to a reductive removal of the arenesulfonyl group, W, (i.e., desulfonation) to obtain the 4-substituted 3-methyl-1,3-butadiene compound (A). There is a possibility that the primary allylsulfone compound (D) may be synthesized by the key reaction, allylic rearrangement of an arenesulfonyl group, from a secondary allylsulfone compound (E), 4-substituted 1-halo-4-arenesulfonyl-3-methylenebutane. The secondary allylsulfone compound (E) may be synthesized by alkylation of an anion at position a of sulfone of an allylsulfone compound (F), and the allylsulfone compound (F) may be synthesized from a dihalide compound (G) with exo-methylene. Many of the intermediates, such as sulfone intermediates having exo-double bonds, of the aforesaid synthetic plan are novel compounds were subjected to intensive research based on the aforesaid synthetic plan.

As a result of intensive research based on the aforesaid investigation, the present inventors successfully realized the desired reaction, and efficiently synthesized α-farnesenes and 4-substituted 3-methyl-1,3-butadiene compounds having related structures. Embodiments of the present invention will be described by step in detail below.

Target compounds of the present invention, 4-substituted 3-methyl-1,3-butadiene compounds Target compounds of the present invention, α-farnesenes and 4-substituted 3-methyl-1,3-butadiene compounds having related structures, will be explained in detail below. A 4-substituted 3-methyl-1,3-butadiene compound is represented by the following general formula (A):

(A)

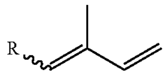

wherein the substituent group R represents a linear, branched, or cyclic hydrocarbon group having 1 to 20 carbon atoms and optionally having an unsaturated bond(s), and the wavy line represents a bond without a specific geometrical isomerism.

In the formula, the wavy line is a bond without a specific geometrical isomerism, and the general formula (A) above represents one or both of the following two geometric isomers: a (E)-isomer, E-(A), and a (Z)-isomer, Z-(A):

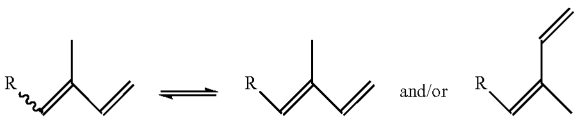

(A) E-(A) and/or Z-(A)

wherein R is as defined above.

The hydrocarbon group R is a hydrocarbon group having 1 to 20, preferably 1 to 15, and more preferably 5 to 15 carbon atoms. Examples of the hydrocarbon group R include linear alkyl groups such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-icosyl group; branched alkyl groups such as an isopropyl group, an isobutyl group, a sec-butyl group, a tert-butyl group, an isopentyl group, and an alkyl group wherein one to six hydrogen atoms of the aforesaid linear alkyl group are substituted with a methyl group or an ethyl group; and a cyclic alkyl group with a cyclic structure such as cyclopropane, cyclobutane, cyclopentane, cyclohexane, and benzene. Examples of the unsaturated bond of the hydrocarbon group R include a double bond and a triple bond. The unsaturated bond of the hydrocarbon group R is preferably a double bond. One to five unsaturated bonds are preferred. R represents, for example, a 3,7-dimethyl-2,6-octadienyl group, a 3-methyl-2-butenyl group, a 3-methyl-3-butenyl group, and a 3-phenyl-2-propenyl group. The 3,7-dimethyl-2,6-octadienyl group includes at least one of (E)- or (Z)-3,7-dimethyl-2,6-octadienyl groups.

Synthesis of Starting Material, Allylsulfone Compound (F)

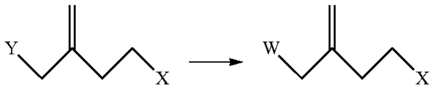

(G) (F)

wherein X and Y represent, independently of each other, a halogen atom, and W represents an arenesulfonyl group.

Although the process for synthesizing the starting material of the present invention, allylsulfone compound (F), is not particularly limited, the allylsulfone compound (F) is obtained, for example, by mixing a dihalide compound (G) having exo-methylene with arenesulfinate salt and heating in a solvent to substitute the halogen atom, Y, at the allyl position with the arenesulfonyl group, W:

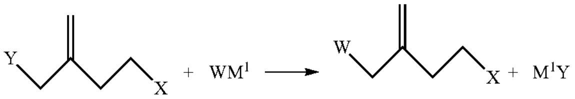

(G) (F)

wherein $WM^1$ represents a sulfonylation agent, and $M^1$ represents a metal atom. W, X, and Y are as defined above.

X and Y of the dihalide compound (G) are, independently of each other, a halogen atom, preferably a chlorine atom, a bromine atom, and an iodine atom, and more preferably a chlorine atom and a bromine atom. X is most preferably a chlorine atom. By using said chlorine atom, stability in subsequent steps may be ensured. Preferred specific examples of the compound (G) include 4-chloro-2-chloromethyl-1-butene, 2-bromomethyl-4-chloro-1-butene, 4-bromo-2-chloromethyl-1-butene, and 4-bromo-2-bromomethyl-1-butene. Instead of the halogen atoms X and Y, a pseudo-halogen group that functions as a leaving group in alkylation (a carbon-carbon bond-forming reaction) of α-anions and elimination of HX for olefin formation, that will be explained below, may be used, such as phosphoryloxy groups such as a dimethylphosphoryloxy group, a diethylphosphoryloxy group, and a diphenylphosphoryloxy group; and sulfonyloxy groups such as a methanesulfonyloxy group, a trifluoromethanesulfonyloxy group, a nonafluorobutanesulfonyloxy group, a benzenesulfonyloxy group, and a p-toluenesulfonyloxy group, which are generally referred to as halogen atoms in the present specification hereinafter. W in the allylsulfone compound (F) is an arenesulfonyl group. Because benzene sulfinate and p-toluene sulfinate are commercially available on an industrial basis as corresponding metal arenesulfinates $WM^1$ used as reagents, the arenesulfonyl group, W, is preferably a benzenesulfonyl group and a p-toluenesulfonyl group, and $M^1$ is preferably an alkali metal such as sodium, lithium, and potassium; and an alkaline earth metal such as magnesium and barium. The regioselectivity of this reaction is high, and the halogen atom, Y, at the allyl position reacts preferentially compared to the halogen atom, X, at the homoallyl position to form the allylsulfone compound (F) with high yield. Strictly speaking, W in $WM^1$ is a compound of an arylsulfenyl group Ar—S(═O)—O— in which an oxygen atom O is bonded to the metal atom $M^1$, and W in the sulfone compound (F) is a compound of an arylsulfonyl group Ar—S(═O)$_2$— in which a sulfur atom S is bonded to a carbon atom C.

Alkylation step of the secondary allylsulfone compound (E) from the allylsulfone compound (F)

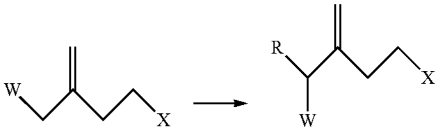

(F) (E)

wherein X and W are as defined above, and R represents a linear, branched, or cyclic hydrocarbon group having 1 to 20 carbon atoms and optionally having an unsaturated bond(s).

This step is directed for an alkylation reaction of position a of the sulfone. The reaction is typically carried out by subjecting a sulfone compound to α-anion formation with a base in a solvent, and by alkylation of the resulting anion with an electrophile:

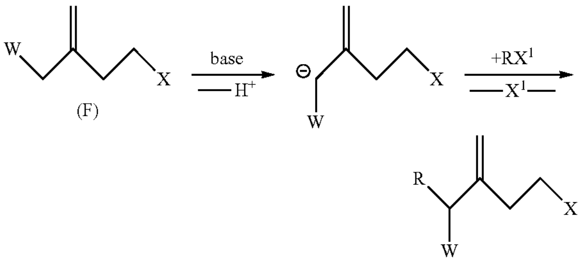

(F)

(E)

wherein "base" represents a base, $RX^1$ represents an electrophile, $X^1$ represents a leaving group, and R, W, and X are as defined above.

Although the base used in the anion formation is not particularly limited as long as an anion can be formed at position a of the sulfone compound, examples of the base include inorganic bases such as sodium hydride, potassium hydride, calcium hydride, sodium amide, potassium amide, sodium hydroxide, and potassium hydroxide; organic bases such as triethylamine, tributylamine, diisopropylethylamine, 1,5-diazabicyclo[4.3.0]-5-nonene (DBN), 1,4-diazabicyclo[2.2.2]octane (DABCO), and 1,8-diazabicyclo[5.4.0]-7-undecene (DBU); alkoxides such as sodium methoxide, sodium ethoxide, lithium tert-butoxide, and potassium tert-butoxide; alkyllithiums such as methyllithium, ethyllithium, n-butyllithium, sec-butyllithium, and tert-butyllithium; Grignard reagents such as methylmagnesium halide (including chloride, bromide, and iodide; hereinafter the same shall apply), ethylmagnesium halide, and phenylmagnesium halide; alkyl metal compounds such as dimethylzinc, diethylzinc, trimethylaluminum, triethylaluminum, and methylaluminumdichloride; and metal amides such as lithium diethylamide, lithium diisopropylamide, lithium isopropylcyclohexylamide, lithium hexamethyldisilazide, sodium hexamethyldisilazide, and halomagnesium hexamethyldisilazide. Any base selected from these is used alone, or in any combination thereof. Halide salts such as lithium chloride may be added. The base is particularly preferably alkyllithiums, Grignard reagents, and metal amides.

The electrophile $RX^1$ used in the alkylation includes a leaving group $X^1$ that introduces a hydrocarbon group R. Although $X^1$ is not particularly limited as long as $X^1$ functions as a leaving group, examples of $X^1$ include a halogen atom (a halo group); phosphoryloxy groups such as a dimethylphosphoryloxy group, a diethylphosphoryloxy group, and a diphenylphosphoryloxy group; and sulfonyloxy groups such as a methanesulfonyloxy group, a trifluoromethanesulfonyloxy group, a nonafluorobutanesulfonyloxy group, a benzenesulfonyloxy group, and a p-toluenesulfonyloxy group. A halogen atom is desirable. By using said halogen atom, desirable economy and availability may be ensured. Among halogen atoms, a chlorine atom, a bromine atom, and an iodine atom are particularly desirable.

Examples of the solvent include ethers such as diethyl ether, dibutyl ether, diethyleneglycol diethyl ether, diethyleneglycol dimethyl ether, tetrahydrofuran, 4-methyltetrahydropyran, and 1,4-dioxane; hydrocarbons such as hexane, heptane, benzene, toluene, xylene, and cumene; chlorinated solvents such as methylene chloride, chloroform, and trichloroethylene; nitriles such as acetonitrile; ketones such as acetone and 2-butanone; esters such as ethyl acetate and butyl acetate; and aprotic polar solvents such as N,N-dimethylformamide, dimethyl sulfoxide, and hexamethylphosphoric triamide. Any solvent selected from these is used alone, or in any combination thereof. A more appropriate reaction temperature may be selected according to the type of base used and reaction conditions. Typically, the reaction temperature is preferably −50° C. to the boiling point of the solvent, and more preferably −20° C. to a room temperature (5° C. to 35° C.; hereinafter the same shall apply). Although the reaction time may be arbitrarily set, the conversion and/or the isomer ratio may be optimized by monitoring with gas chromatography (GC) or thin layer chromatography (TLC). The reaction time is typically and preferably 5 minutes to 240 hours.

When the secondary allylsulfone compound (E) obtained in the aforesaid alkylation step and a halogen exchange step, that will be explained below, has a sufficient purity and isomer ratio, the secondary allylsulfone compound (E) may be used in a subsequent step as a crude product. However, purification and isomer separation may be selected from any suitable purification method or isomer separation process used in usual organic synthesis such as distillation or various chromatography.

Isomerization step from the secondary allylsulfone compound (E) to the primary allylsulfone compound (D) by allylic rearrangement of arenesulfonyl group

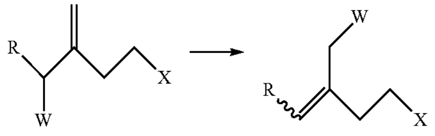

(E) (D)

wherein R, W, and X are as defined above.

This isomerization step is an isomerization step from a secondary allylsulfone compound (E) having an exo-methylene structure to a primary allylsulfone compound (D) having a trisubstituted double bond that is thermodynamically more stable. This step was found to proceed in the presence of a transition metal compound, thereby synthesizing the key intermediate, primary allylsulfone compound (D). The isomerization step typically proceeds by heating the secondary allylsulfone compound (E) with a transition metal compound in a solvent.

In this isomerization step, the reaction substrate, secondary allylsulfone compound (E), may be a chloride compound (when X=Cl), a bromide compound (when X=Br), and an iodide compound (when X=I). These compounds may be synthesized, for example, by "Halogen exchange step of intermediate" below.

Examples of the transition metal compound used in the isomerization step include transition metal compounds such as nickel, rhodium, palladium, ruthenium, and iridium. A palladium compound is particularly preferred. Specific examples of the palladium compound include zero-valent palladium compounds such as tetrakis(triphenylphosphine)palladium(0), bis(dibenzylideneacetone)palladium(0), tris(dibenzylideneacetone)dipalladium(0), tris(dibenzylideneacetone)(chloroform)dipalladium(0), and bis(tri-tert-butylphosphine)palladium(0); and divalent palladium compounds such as bis(acetylacetonato)palladium(II), dichlorobis(allyl)palladium(II), bis(acetonitrile)dichloropalladium(II), trifluoroacetic acid palladium(II), palladium acetate(II), dichlorobis(tricyclohexylphosphine)palladium(II), dichlorobis(triphenylphosphine)palladium(II), dichlorobis(tri-o-tolylphosphine)palladium(II), dichlorobis[di-t-butyl(p-dimethylaminophenyl)phosphine]palladium(II), 1,1'-bis(diphenylphosphino)ferrocenedichloropalladium(II), 1,1'-bis(diphenylphosphino)ferrocenedichloropalladium(II)-dichloromethane, tetrakis(acetonitrile)palladium(II) tetrafluoroborate, palladium(II) bromide, palladium(II) chloride, dichloro[1,3-bis(diphenylphosphino)propane]palladium(II), and dichloro[1,2-bis(diphenylphosphino)ethane]palladium(II). A phosphorus compound may be used as a ligand with these palladium compounds. Examples of the phosphorus compound used as the ligand include phosphines such as trimethylphosphine, tri-tert-butylphosphine, trioctylphosphine, tricyclohexylphosphine, tri(o-tolyl)phosphine, dimethylphenylphosphine, tri(2-furyl)phosphine, diphenyl-2-pyridylphosphine, tris(hydroxymethyl)phosphine, 1,2-bis(dimethylphosphino)ethane, bis(diphenylphosphino)methane, 1,2-bis(diphenylphosphino)ethane, 1,3-bis(diphenylphosphino)propane, 1,4-bis(diphenylphosphino)butane, 1,2-bis(dicyclohexylphosphino)ethane, and 2-dicyclohexylphosphino-2,6-dimethoxybiphenyl; and phosphite esters such as trimethylphosphite, triethylphosphite, and triphenylphosphite. These transition metal compounds and ligands may be used alone, or in any combination thereof. The palladium compound is preferably zero-valent palladium compounds, and combinations of divalent palladium compounds and bidentate phosphines. An organometallic compound or a metal hydride compound may be used to activate the catalytic activity of the transition metal compound. The amount of the transition metal compound used, per mol of the secondary allylsulfone compound (E), is 0.000001 to 10 mol, and preferably 0.00001 to 0.1 mol. By using said preferred amount, preferred economy may be ensured. The amount of the phosphorus compound used as the ligand, per mol of the palladium compound, is 0.1 to 1,000 mol, and preferably 1 to 100 mol. Examples of the solvent used in the isomerization step include, for example, ethers such as diethyl ether, dibutyl ether, t-butyl methyl ether, cyclopentyl methyl ether, tetrahydrofuran, 4-methyltetrahydropyran, and 1,4-dioxane; alcohols such as methanol, ethanol, 1-propanol, 2-propanol, tert-butyl alcohol, ethylene glycol monomethyl ether, and diethyleneglycol monomethyl ether; hydrocarbons such as hexane, heptane, benzene, toluene, xylene, and cumene; carboxylic acids such as formic acid, acetic acid, propionic acid, and benzoic acid; nitriles such as acetonitrile and propionitrile; ketones such as acetone and 2-butanone; esters such as ethyl acetate and butyl acetate; and aprotic polar solvents such as N,N-dimethylformamide (DMF), N,N-dimethylacetamide, N,N-dimethylpropionamide, 1,3-dimethyl-2-imidazolidinone (DMI), dimethyl sulfoxide (DMSO), and hexamethylphosphoric triamide (HMPA). The solvents may be used alone, or in any combination thereof. The reaction solvent is preferably ethers and hydrocarbons, alone or in combination thereof. The reaction solvent also is preferably a mixed solvent including alcohols and carboxylic acids as proton sources. The reaction temperature in the isomerization step is preferably −78° C. to the boiling point of the solvent, and more preferably −10° C. to 100° C. Although the reaction time may be arbitrarily set, optimization is possible by monitoring the progress of the reaction by gas chromatography (GC) or thin layer chromatography (TLC). The reaction time is typically and preferably 5 minutes to 240 hours. Appropriate reaction conditions of the isomerization step such as the transition metal catalyst, the solvent, the reaction concentration, and the reaction temperature may be selected and optimized in view of, for example, the reaction rate, the generation of by-products, and the geometric isomer ratio of the target, primary allylsulfone compound (D).

A crude product of the primary allylsulfone compound (D) obtained by the aforesaid isomerization step may be used as such in a subsequent step when having a sufficient purity. Alternatively, the crude product may be separated and purified in any purification method used in usual organic synthesis, such as distillation and/or various chromatography. Although dependent on the structure of the substituent group R at position 4, the starting material, the secondary allylsulfone compound (E), may be separated from the target compound, primary allylsulfone compound (D), even when the isomerization reaction does not proceed to completion and the secondary allylsulfone compound (E) remains in the primary allylsulfone compound (D).

Although dependent on the structure of the substituent group R at position 4, it was found that the geometric isomers of the primary allylsulfone compound (D), E-(D) and Z-(D) below, may be separated from each other:

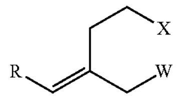

E-(D)

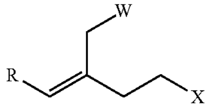

Z-(D)

wherein R, W, and X are as defined above.

As explained below, the two types of geometric isomers of the primary allylsulfone compound (D) may be used to form geometric isomers of the 4-substituted 3-methyl-1,3-butadiene compound (A) that are stereospecifically corresponding target compounds, that is, the compound E-(D) may be used to form a diene compound Z-(A), and the compound Z-(D) may be used to form a diene compound E-(A). Therefore, to obtain the 4-substituted 3-methyl-1,3-butadiene compound (A) with high geometric isomer purity, it is extremely important to be able to separate the geometric isomers. Examples of a separation process of the isomers particularly include separation processes that use a polarity difference, such as chromatography. Silica gel column chromatography is particularly preferred.

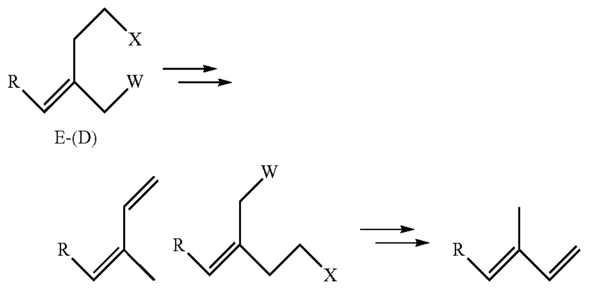

E-(D)

Z-(A) Z-(D) E-(A)

wherein R, W, and X are as defined above.

Reisomerization may be carried out by reusing a mixture of the starting material, secondary allylsulfone compound (E), and the geometric isomers E-(D) and Z-(D) of the product, primary allylsulfone compound, at any ratio, as the substrate of this isomerization step. To prepare specific geometric isomers, the ability to recycle unnecessary isomers by reisomerization has great industrial significance.

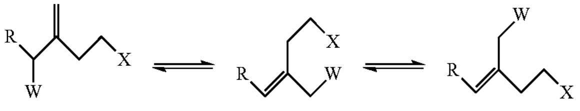

(E) E-(D) Z-(D)

wherein R, W, and X are as defined above.

When the primary allylsulfone compound (D) obtained by the aforesaid isomerization step or by "Halogen exchange step of intermediate", to be explained below, has a sufficient purity and/or isomer ratio, the crude product may be used as such in a subsequent step. Alternatively, the crude product may be separated into isomers and/or purified in any isomer separation process or purification method used in usual organic synthesis, such as distillation and/or various chromatography.

Next, the following two processes are possible as synthetic routes from the primary allylsulfone compound (D) thus obtained to the 4-substituted 3-methyl-1,3-butadiene compound (A).

(I) A process via a halide compound (B), specifically, (I)-(1) reductive reductive removal of the arenesulfonyl group, W, of the allyl position of the primary allylsulfone compound (D) (i.e., desulfonation) to form a halide compound (B), and then (I)-(2) elimination of the hydrogen halide, HX, of the halide compound (B) to form the target compound, 4-alkyl-3-methyl-1,3-butadiene compound (A):

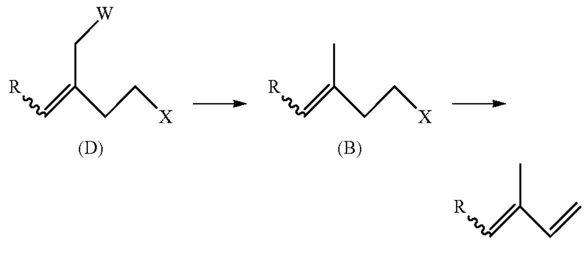

(D) (B) (A)

wherein R, W, and X are as defined above.

(II) A process via a primary allylsulfonediene compound (C), specifically, (II)-(1) elimination of the hydrogen halide, HX, of the primary allylsulfone compound (D) to form a primary allylsulfonediene compound (C), and then (II)-(2) reductive removal of the arenesulfonyl group, W, of the primary allylsulfonediene compound (C) (i.e., desulfonation) to form the target compound, 4-substituted 3-methyl-1,3-butadiene compound (A):

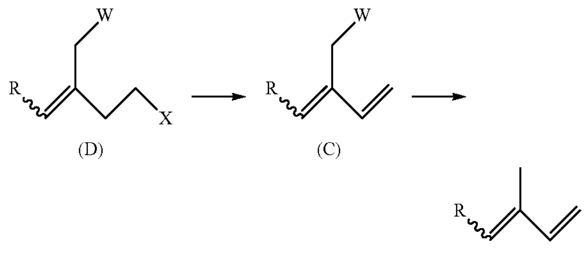

(D) (C) (A)

wherein R, W, and X are as defined above.

The synthetic routes (I) and (II) will be explained below in order, and their applications will be explained below.

(I)-(1) Reductive Removal Step of Arenesulfonyl Group, W, of the Allyl Position of the Primary Allylsulfone Compound (D) to Form Halide Compound (B)

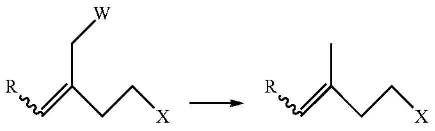

(D) (B)

wherein R, W, and X are as defined above.

The reductive removal (i.e., desulfonation) step is a step of substituting the arenesulfonyl group, W, with the hydrogen atom H.

In the reductive removal step, the reaction substrate, primary allylsulfone compound (D), may be a chloride compound (when X=Cl), a bromide compound (when X=Br), and an iodide compound (when X=I). While the aforesaid compounds may be synthesized, for example, in "Halogen exchange step of intermediate" that will be explained below, a chloride compound is preferred as the substrate of the reductive removal step. By using said chloride compound, a preferred suppression of side reactions may be ensured.

Although the process used for the reductive removal may be a known process and is not particularly limited, examples include a direct electron reduction reaction with a metal or metal salt, a nucleophilic substitution reduction reaction with a hydride ($H^-$) nucleophilic reagent, and a radical substitution reduction reaction with a hydrogen radical (H') reagent.

Examples of reagents used in the direct electron reduction reaction with a metal or metal salt include alkali metals such as sodium and lithium; other metals such as magnesium, zinc, and tin; amalgams of various metals and combinations of protic solvents such as lower amines such as ammonia, methylamine, ethylamine, and propylamine; lower alcohols such as methanol, ethanol, 1-propanol, 2-propanol, 1-butanol, and 2-butanol; carboxylic acids such as formic acid, acetic acid, and propionic acid; and metal salts such as samarium diiodide. Preferred specific examples of metal-protic solvents include lithium-ammonia, sodium-ammonia, sodium-lower amine, lithium-lower amine, magnesium-methanol, and zinc-acetic acid. It is preferred to use sodium-naphthalenide and Raney-nickel (Raney-Ni) in a solvent. Examples of amalgams include sodium-amalgam and aluminum-amalgam. Among these reagents, lithium-ammonia, sodium-ammonia, sodium-lower amine, lithium-lower amine, and magnesium-methanol are preferred. By using said lithium-ammonia, sodium-ammonia, sodium-lower amine, lithium-lower amine, and magnesium-methanol, a preferred industrial application may be ensured. Examples of the hydride ($H^-$) nucleophilic reagent used in the nucleophilic substitution reduction reaction include borane compounds such as borane, alkylborane, dialkylborane, bis(3-methyl-2-butyl)borane; silane compounds such as dialkylsilane and trialkylsilane; alane compounds such as alkylaluminum, dialkylaluminum (diisobutylaluminum hydride, etc.); metal hydrides such as sodium hydride, lithium hydride, potassium hydride, and calcium hydride; complex hydrides such as sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri-tert-butoxyaluminum hydride, sodiumbis(2-methoxyethoxy)aluminum hydride, and lithium triethylborohydride; and alkoxy or alkyl derivatives thereof. Such complex hydrides also may be combined with formic acid as a hydride source. The transition metal catalyst may be incorporated in the nucleophilic reduction reaction. Examples of the transition metal catalyst include transition metal compounds such as nickel, rhodium, palladium, ruthenium, and iridium. Palladium compounds are particularly preferred. Examples of preferred palladium compounds include zerovalent palladium compounds and divalent palladium compounds similar to those mentioned above in the isomerization step from the secondary allylsulfone compound (E) to the primary allylsulfone compound (D) by allylic rearrangement of the arenesulfonyl group. A phosphorus compound may be used as a ligand with these palladium compounds as mentioned above. A combination of a complex hydride with a palladium compound is preferred. Combinations of lithium triethylborohydride with a transition metal catalyst; and lithium borohydride with formic acid and a transition metal catalyst are particularly preferred. By using said combinations of lithium triethylborohydride with a transition metal catalyst; and lithium borohydride with formic acid and a transition metal catalyst, particularly preferred specificity (in this case, a substitution reaction of the $S_N2$ mechanism without allylic rearrangement) may be ensured. Although the aforesaid palladium compound is preferably zero-valent, a divalent palladium compound also is preferred due to the divalent metallic compound reducing to zero-valent under reduction conditions in the reaction system. Examples of the hydrogen radical (H') reagent used in the radical substitution reduction reaction include tributyltin hydride (TBTH). A radical initiator such as an azo compound such as 2,2'-azobisisobutyronitrile, dimethyl 2,2'-azobis(isobutyrate), and 1,1'-azobis(cyclohexanecarbonitrile); and an organic peroxide such as di-tert-butyl peroxide, tert-butylhydroperoxide, and benzoyl peroxide may be used in combination in the radical reduction reaction.

In addition to the aforesaid protic solvents, examples of a solvent used in the reductive removal step include water; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, 1,4-dioxane, and 4-methyltetrahydropyran; alcohols such as methanol, ethanol, 1-propanol, 2-propanol, t-butyl alcohol, benzyl alcohol, methoxyethanol, and ethoxyethanol; ketones such as acetone and 2-butanone; nitriles such as acetonitrile and propionitrile; esters such as ethyl acetate and butyl acetate; and aprotic polar solvents such as N,N-dimethylformamide (DMF), 1,3-dimethyl-2-imidazolidinone (DMI), dimethyl sulfoxide (DMSO), and hexamethylphosphoric triamide (HMPA). The solvent is appropriately selected, depending on the type of reagent to be used, and may be used alone, or in any combination thereof. A reaction temperature of the reductive removal step varies, depending on the reagent and the solvent to be used, and is preferably −78° C. to 50° C., and more preferably −70° C. to 20° C. A reaction time may be arbitrarily set. In view of the yield, it is desirable to monitor progress of the reaction with gas chromatography (GC) and/or thin layer chromatography (TLC) to complete the reaction. The reaction time is typically and preferably 5 minutes to 240 hours.

Excessive reagents and extreme reaction conditions in the aforesaid reductive removal step should be avoided due to the risk of a side reaction in which not only the arenesulfonyl group, W, but also the halogen atom (halo group) X is reductively removed and substituted with a hydrogen atom. It was found that appropriate selection of the reagent types and reaction conditions gave good selectivity, in which the arenesulfonyl group, W, was reductively removed while the halo group X remained, and that X is particularly preferably a chlorine atom. By using said chlorine atom, a particularly preferred selectivity may be ensured.

A halide compound (B) also may be obtained directly by using the secondary allylsulfone compound (E) of the previous step as a reaction substrate, and by selecting the conditions of the reductive removal step, such as the reductive removal below having a substitution reaction by the $S_N2'$ mechanism with allylic rearrangement. In such a case, typically, there is competition between the $S_N2$ mechanism without rearrangement and the $S_N2'$ mechanism with rearrangement, which is effective for obtaining an isomeric mixture as the target compound. However, to selectively synthesize individual isomers, the primary allylsulfone compound (D) is better as the reaction substrate.

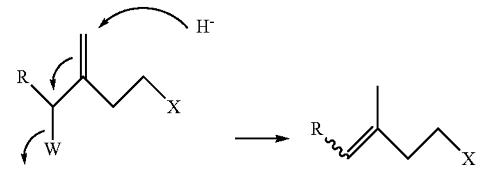

(E) (B)

wherein R, W, and X are as defined above.

A crude product of the halide compound (B) obtained from the aforesaid reductive removal step or the halogen exchange step, that will be explained below, may be used as such in a subsequent step when having a sufficient purity and isomer ratio. Alternatively, the crude product may be purified and separated into isomers in any purification method and isomer separation process used in usual organic synthesis such as distillation and/or various chromatography.

(I)-(2) Elimination Step of Hydrogen Halide, HX, from Halide Compound (B) to 4-Substituted 3-Methyl-1,3-Butadiene Compound (A)

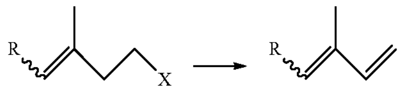

(B) (A)

wherein R and X are as defined above.

This elimination step typically may be carried out by eliminating HX in the presence of a base in a solvent or without a solvent, with heating or cooling, if necessary.

The reaction substrate of this elimination step, halide compound (B), may be a chloride compound (when X═Cl), a bromide compound (when X═Br), and an iodide compound (when X═I). These compounds may be synthesized, for example, in "Halogen exchange step of intermediate" that will be explained below.

Examples of the base used in the elimination step include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; hydrides such as lithium hydride, sodium hydride, potassium hydride, and calcium hydride; hydroxide salts such as sodium hydroxide, lithium hydroxide, potassium hydroxide, and barium hydroxide; carbonates such as sodium carbonate, potassium carbonate, sodium bicarbonate, and potassium bicarbonate; organometallic reagents such as methyllithium, ethyllithium, n-butyllithium, and methylmagnesium chloride; metal amides such as lithium amide, sodium amide, lithium diisopropylamide, lithium hexamethyldisilazide, sodium hexamethyldisilazide, and lithium dicyclohexylamide; and organic bases such as ammonia, methylamine, ethylamine, propylamine, diethylamine, di-n-propylamine, diisopropylamine, di-n-butylamine, triethylamine, diisopropylethylamine, tributylamine, N,N-dimethylaniline, N,N-diethylaniline, pyridine, 4-dimethylaminopyridine, quinoline, pyrrolidine, piperidine, collidine, lutidine, morpholine, piperazine, 1,5-diazabicyclo [4.3.0]-5-nonene (DBN), 1,4-diazabicyclo[2.2.2]octane (DABCO), and 1,8-diazabicyclo[5.4.0]-7-undecene (DBU). The base may be used alone, or in any combination thereof, and is selected, depending on the substrate type, reactivity, and/or selectivity. Preferred examples of the base include carbonates such as potassium carbonate; alkoxides such as potassium t-butoxide; and organic bases such as 1,5-diazabicyclo[4.3.0]-5-nonene (DBN), 1,4-diazabicyclo[2.2.2] octane (DABCO), and 1,8-diazabicyclo[5.4.0]-7-undecene (DBU). The amount of the base used is 0.01 to 100 mol, per mol of the substrate, halide compound (B), and preferably 0.1 to 10 mol. Examples of the solvent used in the elimination step include water; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, 1,4-dioxane, and 4-methyltetrahydropyran; alcohols such as methanol, ethanol, 1-propanol, 2-propanol, t-butyl alcohol, benzyl alcohol, methoxyethanol, and ethoxyethanol; ketones such as acetone and 2-butanone; nitriles such as acetonitrile and propionitrile; esters such as ethyl acetate and butyl acetate; and aprotic polar solvents such as N,N-dimethylformamide (DMF), 1,3-dimethyl-2-imidazolidinone (DMI), dimethyl sulfoxide (DMSO), and hexamethylphosphoric triamide (HMPA). The solvent is appropriately selected, depending on the type of reagent to be used, and may be used alone, or in any combination thereof. A reaction temperature of the elimination step varies, depending on the reagent and/or the solvent used, and is preferably −78° C. to 200° C., and more preferably 0° C. to 100° C. A reaction time may be arbitrarily set. In view of the yield, it is desirable to monitor progress of the reaction with gas chromatography (GC) and/or thin layer chromatography (TLC) to complete the reaction. The reaction time is typically and preferably 5 minutes to 240 hours. The target compound, 3-methyl-1,3-butadiene compound (A), has a thermally unstable diene structure, and so reactions at high temperatures for long periods of time should be avoided. Mild conditions such that the reaction proceeds at low temperatures for short periods of time are preferred.

Next, the synthetic route (II) will be explained in detail below. The synthetic route (II) is the two steps of.

(II)-(1) Elimination Step of Hydrogen Halide, HX, from Primary Allylsulfone Compound (D) to Primary Allylsulfonediene Compound (C):

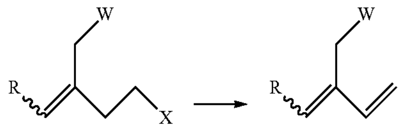

(D) (C)

wherein R, W, and X are the aforesaid, and (II)-(2) Reductive Removal Step of Arenesulfonyl Group, W, from Primary Allylsulfonediene Compound (C) (i.e., Desulfonation) to 4-Substituted 3-Methyl-1,3-Butadiene Compound (A):

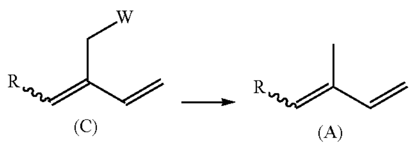

(C) (A)

wherein R, W, and X are the aforesaid.

The step (II)-(1) may be carried out by eliminating HX, similarly to the aforementioned (I)-(2) “Elimination step of hydrogen halide, HX, from halide compound (B) to 4-substituted 3-methyl-1,3-butadiene compound (A)”. The step (II)-(2) may be carried out by reductively removing the arenesulfonyl group, W, of the allyl position, similarly to (I)-(1) “Reductive reductive step of arenesulfonyl group, W, of the allyl position from the primary allylsulfone compound (D) to the halide compound (B)”.

However, it was found from various investigations that the elimination reaction of HX from the primary allylsulfone compound (D) having the arenesulfonyl group, W, was more difficult than from the halide compound (B) without an arenesulfonyl group, W, and an extended heating time needed for the reaction resulted in side reactions such as isomerization due to the allylic rearrangement, polyene formation due to the elimination of the arenesulfonyl group, W, thermal decomposition, and dimerization of products. Details will be explained below as Comparative Synthetic Examples.

Thus, it was found that, as the synthetic route from the primary allylsulfone compound (D) to the 4-substituted 3-methyl-1,3-butadiene compound (A), the synthetic route (I) via the halide compound (B) is more preferred than the synthetic route (II) via the primary allylsulfonediene compound (C), in view of the cleanness of the reaction, the stereospecificity, the yield, thermally, and the ability to construct an unstable conjugated diene structure in the presence of an acid in the final step.

Halogen Exchange Step of Intermediate

Among the intermediates of this preparation process, the secondary allylsulfone compound (E), the primary allylsulfone compound (D), and the halide compound (B) have the halogen atom (halo group) X and may be three types of compounds, specifically, a chloride compound, a bromide compound, and an iodide compound, depending on the type of the halogen atom X. One type of halide compound may be used as a starting material to synthesize, with a halogen conversion reaction, another type of halide compound to be used in the step. To improve the reactivity, it is preferred to convert to a halide compound having high reactivity such as, for example, converting from a chloride compound to a bromide compound, from a chloride compound to an iodide compound, and from a bromide compound to an iodide compound. The conversion may be selected based on the yield, the reactivity, and the stability of the intermediate. The halogen exchange reaction may be a known process such as heating a halide compound as a starting material such as, for example, a chloride compound and/or a bromide compound in a solvent with a halogen source such as a halide salt having a halide ion X-such as, for example, $Br^-$ and/or $I^-$ of another halogen atom present in the target compound such as a bromide compound and/or an iodide compound. The halogen exchange reaction may be carried out in situ in the step. Although the halogen exchange reaction may be carried out with any of the secondary allylsulfone compound (E), the primary allylsulfone compound (D), and the halide compound (B) as an intermediate, it is preferred to use an appropriate intermediate to avoid undesirable side reactions such as, for example, reduction of the halogen atom in the reductive removal step of the arenesulfonyl group, W. The appropriate intermediate is preferably the primary allylsulfone compound (D) or the halide compound (B), and particularly preferably the halide compound (B).

Examples of advantages of the preparation process of the present invention above include the following:

(1) The stability of the synthetic intermediate, in the steps and in storage, is high because the unstable conjugated diene structure is constructed in the final stage of the synthesis or in one step previous.

(2) When the substituent group R and/or W is achiral in the synthetic intermediate, there is one or no asymmetric carbons in the molecule (multiple asymmetric carbon atoms are not present), and so diastereomers derived from asymmetric carbons are not generated, and purification and/or analysis of the intermediate is easier than synthesis with a mixture of diastereomers as an intermediate.

(3) The target compound may be synthesized with high purity of isomers by selecting reagents and/or reaction conditions having good selectivity.

(4) Applications to synthesize various derivatives having substituted butadiene structures characteristic to farnesenes are possible.

(5) An isomeric mixture may be used as such for the purpose of biological activity. In such a case, an economic synthesizing process may be advantageous, even with low selectivity.

(6) The target compound thus obtained is highly stable, and may be stored at a room temperature. Purification may be carried out with a common purification method of organic compounds, such as distillation and/or silica gel chromatography.

EXAMPLES

The present invention will be described with reference to the following Examples. It should be noted that the present invention is not limited to or by the Examples.

Purities of raw materials, products, and intermediates were determined by gas chromatography (GC) and expressed as % GC, and determined by proton nuclear magnetic resonance ($^1$H-NMR) and expressed as % NMR. Isomer ratios of products and intermediates were the ratios of GC or $^1$H-NMR.

GC conditions: GC: Capillary gas chromatograph GC-14A (Shimadzu Corporation); column: 5% Ph-Me silicone, 0.25 mmφ×25 m; carrier gas: He, detector: FID.

The yield is a calculated yield based on % GC or % NMR. Because raw materials used in reactions and products obtained in reactions do not always have a purity of 100%, a yield is calculated by the following equation: Calculated Yield (%)={[(weight of a product obtained in a reaction x % GC)/molecular weight of a product]÷[(weight of a starting material in a reaction x % GC)/molecular weight of a starting material]×100. Detection sensitivities in gas chromatography may differ among compounds, so that calculated yields may sometimes exceed 100%, particularly when raw materials or products are crude.

Purification was carried out to obtain samples for measuring spectra of the materials, where necessary.

Synthetic Examples: Synthesis of Allylsulfone Compound of the Following General Formula (F)

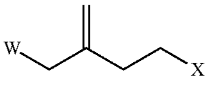

(F)

Synthetic Example 1: Synthesis of 4-Chloro-2-Methylenebutyl p-Tolyl Sulfone (When W=Ts=p-Toluenesulfonyl Group and X=Cl in General Formula (F))

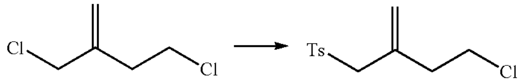

4-Chloro-2-chloromethyl-1-butene (12.51 g) was added dropwise to a mixture of sodium p-toluenesulphinate-tetrahydrate (22.60 g) and dimethylformamide (DMF; 120 ml) in a nitrogen atmosphere at 25° C. or lower, while cooled in an ice-water bath with stirring. After stirring for 17 hours at a room temperature, sodium p-toluenesulphinate-tetrahydrate (5.05 g) was added, and the reaction mixture was stirred for three more days. Water was added to the mixture, and the mixture was extracted with ethyl acetate. The ethyl acetate solution was subjected to ordinary work-up, i.e., washing, drying, and concentration to obtain 4-chloro-2-methylenebutyl p-tolyl sulfone (23.85 g, 96.7 to 89% NMR, including DMF 3.3 to 11%, quantitative yield). A part of the reaction mixture was subjected to spectra measurement after removing DMF under vacuum.

4-Chloro-2-methylenebutyl p-tolyl sulfone

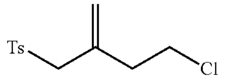 [SMILES: C=C(CCCl)CS(=O)(=O)c1ccc(C)cc1]

$C_{12}H_{15}ClO_2S$

Colorless Crystal

Melting point [inflection point of endothermic peak of DSC (differential scanning calorimeter); hereinafter the same shall apply]: 61.7° C.

IR (D-ATR): ν=2985, 2946, 2929, 1647, 1598, 1494, 1448, 1418, 1405, 1381, 1315, 1308, 1298, 1274, 1237, 1206, 1170, 1147, 1121, 1086, 1034, 1020, 938, 920, 816, 804, 780, 709, 650, 637, 611, 516, 454 $cm^{-1}$.

$^1$H-NMR (500 MHz, $CDCl_3$): δ=2.44 (3H, s), 2.68 (2H, t, J=6.7 Hz), 3.64 (2H, t, J=6.7 Hz), 3.78 (2H, s), 4.89 (1H, br.s), 5.15 (1H, br.s), 7.34 (2H, d-like, J=~8 Hz), 7.74 (2H, d-like, J=~8 Hz) ppm.

$^{13}$C-NMR (125 MHz, $CDCl_3$): δ=21.61, 37.91, 42.07, 62.57, 122.44, 128.44, 129.67, 133.60, 135.12, 144.84 ppm.

GC-MS (EI, 70 eV): 27, 41, 67 (base peak), 91, 105, 131, 155, 179, 194, 223, 241, 258 ($M^+$).

Synthetic Example 2: Synthesis of 4-chloro-2-methylenebutyl phenyl sulfone (When W=Benzenesulfonyl Group and X=Cl in General Formula (F))

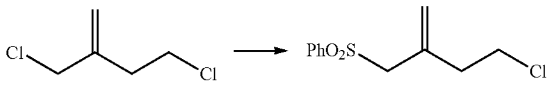

wherein Ph represents a phenyl group; hereinafter the same shall apply.

4-Chloro-2-chloromethyl-1-butene (41.2 g) was added dropwise for 35 minutes to a mixture of sodium benzene-sulfinate-dihydrate (71.0 g), tetrabutylammonium chloride (TBAC; 2.00 g), and acetonitrile (500 ml) in a nitrogen atmosphere with stirring at 50° C. The mixture was heated under reflux at 80 to 95° C. for 6 hours, and then stirred for 2 days at a room temperature. Water was added to the mixture, and the mixture was extracted with ethyl acetate. The ethyl acetate solution was subjected to ordinary work-up, i.e., washing, drying, and concentration to obtain a crude product. The crude product was recrystallized from ethyl acetate-n-hexane to obtain 4-chloro-2-methylenebutyl phenyl sulfone (63.54 g, including TBAC 2.3% NMR, yield 89.4%). A part of the reaction mixture was purified by silica gel column chromatography and subjected to spectra measurement.

4-Chloro-2-methylenebutyl phenyl sulfone

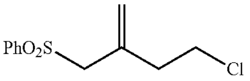

$C_{11}H_{13}ClO_2S$

Colorless Crystal

Melting point: 45.1° C.

IR (D-ATR): ν=3086, 2970, 2927, 1649, 1585, 1479, 1447, 1409, 1317, 1294, 1273, 1237, 1203, 1168, 1145, 1118, 1084, 1029, 999, 939, 922, 888, 797, 784, 757, 712, 690, 651, 615, 531 $cm^{-1}$.

$^1$H-NMR (500 MHz, $CDCl_3$): δ=2.70 (2H, t, J=6.7 Hz), 3.65 (2H, t, J=6.7 Hz), 3.81 (2H, s), 4.90 (1H, br.s), 5.16 (1H, br.s), 7.54-7.59 (2H, m), 7.64-7.68 (1H, m) 7.86-7.90 (2H, m) ppm.

$^{13}$C-NMR (125 MHz, $CDCl_3$): δ=37.92, 42.06, 62.55, 122.62, 128.48, 129.09, 133.49, 133.85, 138.07 ppm.

GC-MS (EI, 70 eV): 51, 77, 91, 117 (base peak), 141, 164, 178, 193, 221, 258 ($M^+$).

Examples: Synthesis of a Secondary Allylsulfone Compound of the Following General Formula (E)

(E)

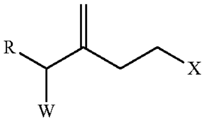

Example 1: Synthesis of (E)-1-chloro-7,11-dimethyl-3-methylene-6,10-dodecadien-4-yl phenyl sulfone (When R=(E)-3,7-dimethyl-2,6-octadienyl group, W=Benzenesulfonyl Group, and X=Cl in General Formula (E))

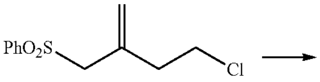

-continued

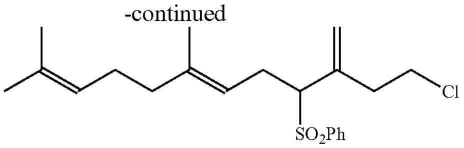

2.80 M n-Butyllithium in n-hexane (70.0 ml) was added dropwise to a mixture of 4-chloro-2-methylenebutyl phenyl sulfone (43.21 g, >99% NMR) synthesized in the aforesaid Synthetic Example 2 and tetrahydrofuran (THF; 500 ml) in a nitrogen atmosphere, while cooling to −65° C. or lower with stirring. The reaction mixture was stirred for 1 hour at this temperature, and then geranyl bromide (42.6 g) was added dropwise for 30 minutes. The reaction mixture was gradually raised to a room temperature and stirred for 30 hours. The reaction mixture was ice-cooled, and the reaction was stopped by adding an aqueous solution of ammonium chloride. The reaction mixture was extracted with ethyl acetate. The ethyl acetate solution was subjected to ordinary work-up, i.e., washing, drying, and concentration, and then purified by silica gel column chromatography to obtain (E)-1-chloro-7,11-dimethyl-3-methylene-6,10-dodecadien-4-yl phenyl sulfone (36.4 g) (yield 54%).

(E)-1-Chloro-7,11-dimethyl-3-methylene-6,10-dodecadien-4-yl phenyl sulfone

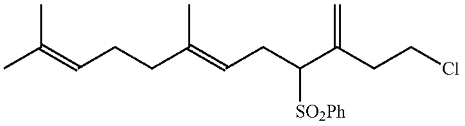

$C_{21}H_{29}ClO_2S$

Yellowish Oil

IR (D-ATR): ν=2965, 2918, 2856, 1644, 1585, 1447, 1377, 1305, 1205, 1146, 1084, 923, 823, 755, 721, 670, 615, 546 $cm^{-1}$.

$^1$H-NMR (500 MHz, $CDCl_3$): δ=1.54 (3H, br.s), 1.56 (3H, br.s), 1.65 (3H, br.s), 1.89-2.03 (4H, m), 2.43-2.59 (3H, m), 2.75-2.81 (1H, m), 3.47-3.59 (3H, m), 4.90-4.95 (1H, m), 4.98-5.03 (1H, m), 5.10 (1H, s-like), 5.22 (1H, s-like), 7.52-7.57 (2H, m), 7.63-7.67 (1H, m), 7.84-7.88 (2H, m) ppm.

$^{13}$C-NMR (125 MHz, $CDCl_3$): δ=16.20, 17.64, 25.65, 26.21, 26.38, 38.29, 39.52, 41.79, 70.56, 118.08, 120.42, 123.81, 128.87, 129.27, 131.63, 133.72, 137.08, 137.29, 139.06 ppm.

Example 2: Synthesis of (Z)-1-chloro-7,11-dimethyl-3-methylene-6,10-dodecadien-4-yl p-tolyl sulfone (When R=(Z)-3,7-dimethyl-2,6-octadienyl group, W=p-toluenesulfonyl Group, and X=Cl in General Formula (E))

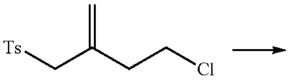

-continued

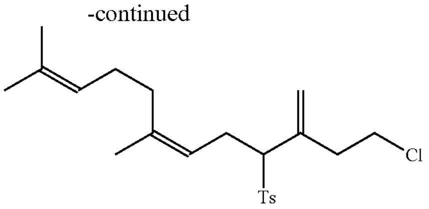

2.80 M n-Butyllithium in n-hexane (28.5 ml) was added dropwise to a mixture of 4-chloro-2-methylenebutyl p-tolyl sulfone (17.1 g, 96.0% NMR) synthesized in the aforesaid Synthetic Example 1 and tetrahydrofuran (250 ml) in a nitrogen atmosphere, while cooling to −60° C. or lower with stirring. The reaction mixture was stirred for 30 minutes at this temperature, and then nellyl bromide (14.60 g) (Z 95.1% NMR) was added dropwise for 10 minutes. The reaction mixture was gradually raised to a room temperature and stirred for 15 hours. The reaction mixture was ice-cooled, and the reaction was stopped by adding an aqueous solution of ammonium chloride. The reaction mixture was extracted with ethyl acetate. The ethyl acetate solution was subjected to ordinary work-up, i.e., washing, drying, and concentration, and then purified by silica gel column chromatography to obtain (Z)-1-chloro-7,11-dimethyl-3-methylene-6,10-dodecadien-4-yl p-tolyl sulfone (19.1 g) (yield 76%).

(Z)-1-Chloro-7,11-dimethyl-3-methylene-6,10-dodecadien-4-yl p-tolyl sulfone

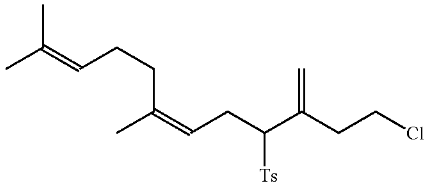 [SMILES: C=C(CCCl)C(C/C=C(/C)CCC=C(C)C)S(=O)(=O)c1ccc(C)cc1]

$C_{22}H_{31}ClO_2S$

Colorless Oil

IR (D-ATR): ν=2965, 2923, 2858, 1643, 1597, 1448, 1377, 1315, 1301, 1290, 1145, 1085, 922, 816, 735, 667, 593 $cm^{-1}$.

$^1$H-NMR (500 MHz, $CDCl_3$): δ=1.59 (3H, br.s), 1.63 (3H, d, J=~1.3 Hz), 1.67 (3H, br.s), 1.87-2.03 (4H, m), 2.41-2.58 (3H, m), 2.45 (3H, s), 2.74-2.81 (1H, m), 3.43-3.60 (3H, m), 4.93 (1H, t-like, J=~8 Hz), 4.99-5.03 (1H, m), 5.11 (1H, s-like), 5.23 (1H, s-like), 7.33 (2H, dd-like, J=~8.5, ~0.6 Hz), 7.72 (2H, dt-like, J=~8.5, ~2 Hz) ppm.

$^{13}$C-NMR (125 MHz, $CDCl_3$): δ=17.63, 21.63, 23.28, 25.73, 26.15, 26.25, 31.95, 38.56, 41.81, 70.72, 118.94, 120.28, 123.78, 129.28, 129.49, 131.94, 134.41, 137.12, 139.04, 144.69 ppm.

Example 3: Synthesis of 1-chloro-7-methyl-3-methylen-6-octen-4-yl p-tolyl sulfone (When R=3-methyl-2-butenyl Group, W=p-toluenesulfonyl Group, and X=Cl in General Formula (E))

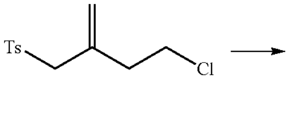

-continued

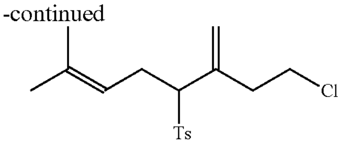

2.80 M n-Butyllithium in n-hexane (7.35 ml) was added dropwise to a mixture of 4-chloro-2-methylenebutyl p-tolyl sulfone (5.00 g, 96.7% NMR) synthesized in the aforesaid Synthetic Example 2 and tetrahydrofuran (80 ml) in a nitrogen atmosphere, while cooling to −60° C. or lower with stirring. The reaction mixture was stirred for 40 minutes at this temperature, and then prenyl bromide (1-bromo-3-methyl-2-butene) (3.35 g) was added dropwise for 5 minutes. The reaction mixture was gradually raised to a room temperature and stirred for 16 hours. The reaction mixture was ice-cooled, and the reaction was stopped by adding an aqueous solution of ammonium chloride. The reaction mixture was extracted with ethyl acetate. The ethyl acetate solution was subjected to ordinary work-up, i.e., washing, drying, and concentration, and then purified by silica gel column chromatography to obtain 1-chloro-7-methyl-3-methylen-6-octen-4-yl p-tolyl sulfone [5.35 g, 97.4 to 98.7% GC (a purity written as a range means that the purities of the multiple fractions obtained were in the range; hereinafter the same shall apply for purities written % GC and % NMR), including 1.1 to 2.2% of corresponding bromide, 1-bromo-7-methyl-3-methylen-6-octen-4-yl p-tolyl sulfone, yield 88%].

1-Chloro-7-methyl-3-methylen-6-octen-4-yl p-tolyl sulfone

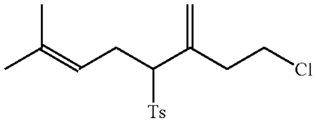 [SMILES: C=C(CCCl)C(CC=C(C)C)S(=O)(=O)c1ccc(C)cc1]

$C_{17}H_{23}ClO_2S$

Yellowish Oil

IR (D-ATR): ν=2967, 2917, 1643, 1597, 1450, 1378, 1315, 1301, 1289, 1144, 1086, 923, 816, 709, 667, 593 $cm^{-1}$.

$^1$H-NMR (500 MHz, $CDCl_3$): δ=1.55 (3H, br.s), 1.63 (3H, d-like, J=~1.2 Hz), 2.42-2.57 (3H, m), 2.44 (3H, s), 2.73-2.79 (1H, m), 3.47-3.52 (2H, m), 3.53-3.58 (1H, m), 4.88-4.93 (1H, m), 5.08 (1H, s-like), 5.21 (1H, s-like), 7.32 (2H, dd-like, J=~8, ~1 Hz), 7.72 (2H, dt-like, J=~8, ~2 Hz) ppm.

$^{13}$C-NMR (125 MHz, $CDCl_3$): δ=17.85, 21.62, 25.63, 38.26, 38.38, 41.83, 70.49, 118.36, 120.25, 129.27, 129.48, 134.32, 135.32, 137.23, 144.69 ppm.

1-Bromo-7-methyl-3-methylen-6-octen-4-yl p-tolyl sulfone

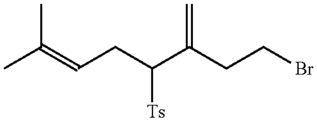 [SMILES: C=C(CCBr)C(CC=C(C)C)S(=O)(=O)c1ccc(C)cc1]

$C_{17}H_{23}BrO_2S$

GC-MS (EI, 70 eV): 41, 79, 107 (base peak), 135, 170, 215, 217.

GC-MS (CI, isobutane): 157, 215, 371, 373 (M+H$^+$, base peak).

Example 4: Synthesis of 1-chloro-7-methyl-3-methylen-6-octen-4-yl phenyl sulfone (When R=3-methyl-2-butenyl Group, W=Benzenesulfonyl Group, and X=Cl in General Formula (E))

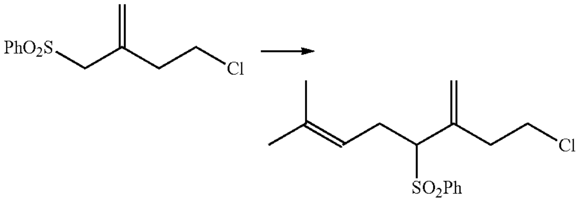

2.76 M n-Butyllithium in n-hexane (150 ml) was added dropwise for 20 minutes to a mixture of 4-chloro-2-methylenebutyl phenyl sulfone (91.4 g, 96% NMR) synthesized by a process similar to the aforesaid Synthetic Example 2 and tetrahydrofuran (800 ml) in a nitrogen atmosphere, while cooling to −60° C. or lower with stirring. The reaction mixture was stirred for 35 minutes at this temperature, and then prenyl bromide (1-bromo-3-methyl-2-butene) (67.0 g) was added dropwise for 20 minutes. The reaction mixture was gradually raised to a room temperature and stirred for 16.5 hours. The reaction mixture was ice-cooled, and the reaction was stopped by adding an aqueous solution of ammonium chloride. The reaction mixture was extracted with ethyl acetate. The ethyl acetate solution was subjected to ordinary work-up, i.e., washing, drying, and concentration to obtain 1-chloro-7-methyl-3-methylen-6-octen-4-yl phenyl sulfone (116.29 g, yield 99%).

1-Chloro-7-methyl-3-methylen-6-octen-4-yl phenyl sulfone

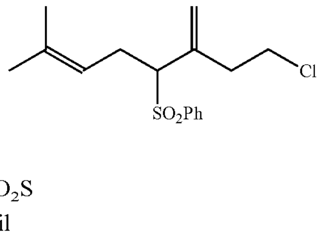

$C_{16}H_{21}ClO_2S$

Yellowish Oil

IR (D-ATR): ν=3064, 2965, 2916, 1673, 1643, 1585, 1447, 1377, 1304, 1244, 1146, 1085, 923, 755, 720, 690, 615 cm$^{-1}$.

$^1$H-NMR (500 MHz, $CDCl_3$): δ=1.54 (3H, br.s), 1.63 (3H, d-like, J=~1 Hz), 2.42-2.58 (3H, m), 2.73-2.82 (1H, m), 3.47-3.59 (3H, m), 4.88-4.93 (1H, m), 5.10 (1H, s-like), 5.22 (1H, s-like), 7.52-7.58 (2H, m), 7.62-7.67 (1H, m), 7.83-7.89 (2H, m) ppm.

$^{13}$C-NMR (125 MHz, $CDCl_3$): δ=17.84, 25.64, 26.35, 38.33, 41.78, 70.49, 118.24, 120.41, 128.86, 129.25, 133.71, 135.47, 137.09, 137.32 ppm.

Example 5: Synthesis of 8-chloro-2-methyl-6-methylen-1-octen-5-yl phenyl sulfone (When R=3-methyl-3-butenyl Group, W=Benzenesulfonyl Group, and X=Cl in General Formula (E))

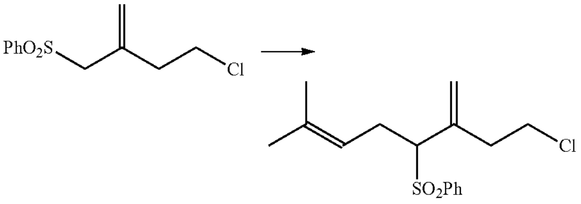

2.64 M n-Butyllithium in n-hexane (28.8 ml) was added dropwise for 10 minutes to a mixture of 4-chloro-2-methylenebutyl phenyl sulfone (16.9 g, ~100% NMR) synthesized by a process similar to the aforesaid Synthetic Example 2 and tetrahydrofuran (160 ml) in a nitrogen atmosphere, while cooling to −60° C. or lower with stirring. The reaction mixture was stirred for 45 minutes at this temperature, and then 4-bromo-2-methyl-2-butene (12.35 g) was added dropwise for 5 minutes. The reaction mixture was gradually raised to a room temperature and stirred for 30 hours. The reaction mixture was ice-cooled, and the reaction was stopped by adding an aqueous solution of ammonium chloride. The reaction mixture was extracted with ethyl acetate. The ethyl acetate solution was subjected to ordinary work-up, i.e., washing, drying, and concentration, and then purified by silica gel column chromatography to obtain 8-chloro-2-methyl-6-methylen-1-octen-5-yl phenyl sulfone (9.38 g, 59.1 to 96.0% GC, including 0 to 4.3% of corresponding bromide: 8-bromo-2-methyl-6-methylen-1-octen-5-yl phenyl sulfone, yield 40%).

8-Chloro-2-methyl-6-methylen-1-octen-5-yl phenyl sulfone

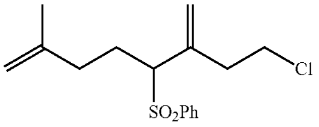

$C_{16}H_{21}ClO_2S$

Yellowish Oil

IR (D-ATR): ν=3071, 2965, 1648, 1585, 1447, 1376, 1305, 1196, 1146, 1085, 895, 756, 721, 690, 612 cm$^{-1}$.

$^1$H-NMR (500 MHz, $CDCl_3$): δ=1.62 (3H, s-like), 1.86-1.98 (2H, m), 2.05-2.12 (1H, m), 2.21-2.28 (1H, m), 2.47-2.55 (1H, m), 2.59-2.66 (1H, m), 3.52-3.67 (3H, m), 4.63 (1H, br.s), 4.74 (1H, br.s), 5.04 (1H, s-like), 5.24 (1H, t-like, J=1.4 Hz), 7.52-7.58 (2H, m), 7.62-7.67 (1H, m), 7.82-7.88 (2H, m) ppm.

$^{13}$C-NMR (125 MHz, $CDCl_3$): δ=21.99, 24.89, 34.03, 37.86, 41.80, 69.97, 111.54, 120.28, 128.87, 129.29, 133.75, 136.91, 137.09, 143.52 ppm.

GC-MS (EI, 70 eV): 39, 55, 77, 93, 109, 129, 155, 171 (base peak).

8-Bromo-2-methyl-6-methylen-1-octen-5-yl phenyl sulfone $C_{16}H_{21}BrO_2S$

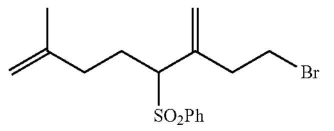

GC-MS (EI, 70 eV): 55, 77 (base peak), 93, 107, 135, 155, 173, 197, 215, 217.

Example 6: Synthesis of (E)-7-chloro-5-methylene-1-phenyl-1-hepten-4-yl p-tolyl sulfone (When R=3-phenyl-2-propenyl Group, W=p-toluenesulfonyl Group, and X=Cl in General Formula (E))

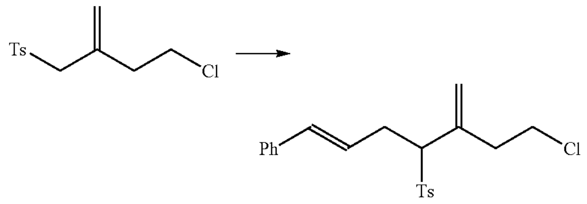

2.80 M n-Butyllithium in n-hexane (26.4 ml) was added dropwise for 15 minutes to a mixture of 4-chloro-2-methylenebutyl p-tolyl sulfone (17.4 g, 97% NMR) synthesized in the aforesaid Synthetic Example 1 and tetrahydrofuran (150 ml) in a nitrogen atmosphere, while cooling to −60° C. or lower with stirring. The reaction mixture was stirred for 1 hour at this temperature, and then cinnamyl bromide (14.6 g) was added dropwise for 15 minutes. The reaction mixture was gradually raised to a room temperature and stirred for 16 hours. The reaction mixture was ice-cooled, and the reaction was stopped by adding an aqueous solution of ammonium chloride. The reaction mixture was extracted with ethyl acetate. The ethyl acetate solution was subjected to ordinary work-up, i.e., washing, drying, and concentration to obtain crude (E)-7-chloro-5-methylene-1-phenyl-1-hepten-4-yl p-tolyl sulfone (26.03 g, quantitative yield). This crude product had sufficient purity, and was used as such as a starting material in a subsequent step.

7-Chloro-5-methylene-1-phenyl-1-hepten-4-yl p-tolyl sulfone

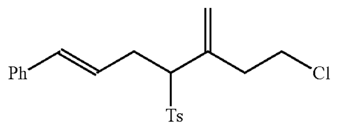 [SMILES: C=C(CCCl)C(C/C=C/c1ccccc1)S(=O)(=O)c1ccc(C)cc1]

$C_{21}H_{23}ClO_2S$

Colorless Oil

IR (D-ATR): ν=3026, 2959, 2923, 2869, 1643, 1597, 1494, 1447, 1313, 1302, 1290, 1144, 1085, 967, 923, 816, 743, 708, 693, 669, 606, 588 $cm^{-1}$.

$^{1}H$-NMR (500 MHz, $CDCl_3$): δ=2.45 (3H, s), 2.48-2.62 (2H, m), 2.68-2.76 (1H, m), 2.96-3.02 (1H, m), 3.51-3.61 (2H, m), 3.66 (1H, dd, J=4.0, 11.4 Hz), 5.14 (1H, s), 5.27 (1H, s-like), 5.99 (1H, dt, J=15.7, 7.2 Hz), 6.42 (1H, dt-like, J=15.7, ~1.2 Hz), 7.18-7.22 (1H, m), 7.26-7.29 (4H, m), 7.34 (2H, d-like, J=~8.5, ~0.6 Hz), 7.75 (2H, dt-like, J=~8.5, ~1.9 Hz) ppm.

$^{13}C$-NMR (125 MHz, $CDCl_3$): δ=21.65, 31.32, 38.32.41, 84, 70.37, 120.67, 124.06, 126.14, 127.54, 128.52, 129.37, 129.58, 133.53, 134.02, 136.69, 136.89, 144.93 ppm.

Example 7: Synthesis of 1-chloro-3-methylenedodecan-4-yl p-tolyl sulfone (When R=n-octyl Group, W=p-toluenesulfonyl Group, and X=Cl in General Formula (E))

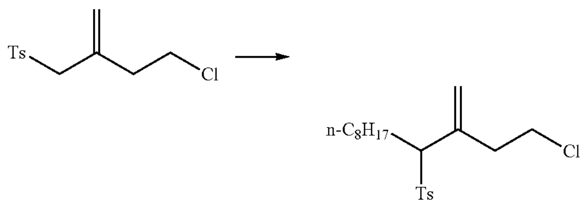

2.76 M n-Butyllithium in n-hexane (65.5 ml) was added dropwise for 30 minutes to a mixture of 4-chloro-2-methylenebutyl p-tolyl sulfone (41.58 g, ~97% NMR) synthesized by a process similar to the aforesaid Synthetic Example 1 and tetrahydrofuran (500 ml) in a nitrogen atmosphere, while cooling to −60° C. or lower with stirring. The reaction mixture was stirred for 40 minutes at this temperature, and then 1-bromooctane (34.8 g) was added dropwise for 10 minutes. The reaction mixture was gradually raised to a room temperature and stirred for 16 hours. The reaction mixture was ice-cooled, and the reaction was stopped by adding an aqueous solution of ammonium chloride. The reaction mixture was extracted with ethyl acetate. The ethyl acetate solution was subjected to ordinary work-up, i.e., washing, drying, and concentration, and then purified by silica gel column chromatography to obtain 1-chloro-3-methylenedodecan-4-yl p-tolyl sulfone (51.1 g, yield 86%).

1-Chloro-3-methylenedodecan-4-yl p-tolyl sulfone

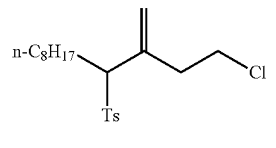

$C_{20}H_{31}ClO_2S$

Colorless Solid

Melting point: 52.5° C.

IR (D-ATR): ν=2954, 2925, 2855, 1642, 1597, 1494, 1456, 1379, 1313, 1302, 1289, 1145, 1086, 1019, 923, 815, 708, 667 $cm^{-1}$.

$^{1}H$-NMR (500 MHz, $CDCl_3$): δ=0.86 (3H, t, J=7.0 Hz), 1.13-1.37 (12H, m), 1.72-1.82 (1H, m), 1.98-2.08 (1H, m), 2.44 (3H, s), 2.45-2.53 (1H, m), 2.56-2.66 (1H, m), 3.50 (1H, dd, J=11.7, 3.5 Hz), 3.56 (1H, dt-like, J=11.7, 3.5 Hz), 3.61 (1H, ddd, J=11.0, 7.5, 6.3 Hz), 5.01 (1H, s), 5.19 (1H, t-like, J=~1.4 Hz), 7.32 (2H, dd-like, J=0.6, 8.6), 7.70 (2H, dt-like, J=8.2, ~2 Hz) ppm.

$^{13}$C-NMR (125 MHz, $CDCl_3$): δ=14.07, 21.64, 22.59, 26.49, 27.12, 29.09, 29.15, 29.19, 31.74, 37.83, 41.90, 71.04, 119.92, 129.29, 129.46, 134.18, 137.33, 144.66 ppm.

Examples: Synthesis of Primary Allylsulfone Compound of the Following General Formula (D)

(D)

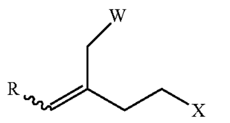

Example 8: Synthesis of (3Z,6E)-(1-chloro-7,11-dimethyl-3,6,10-dodecatrien-3-yl)methyl phenyl sulfone (When R=(E)-3,7-dimethyl-2,6-octadienyl Group, W═Benzenesulfonyl Group, X═Cl, and Geometrical Isomerism of Double Bond of Position 3 is Z-Form in General Formula (D)) and (3E,6E)-(1-chloro-7,11-dimethyl-3,6,10-dodecatrien-3-yl) methyl phenyl sulfone (When R=(E)-3,7-dimethyl-2,6-octadienyl Group, W=Benzenesulfonyl Group, X═Cl, and Geometrical Isomerism of Double Bond of Position 3 is E-Form in General Formula (D))

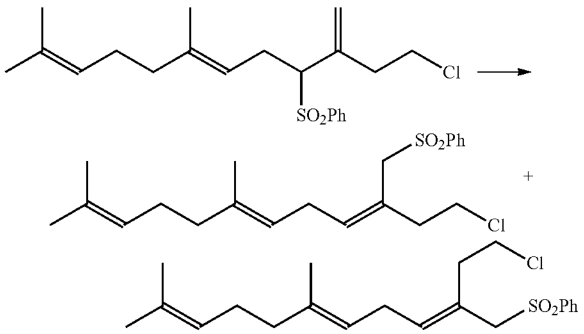

Tetrakis(triphenylphosphine)palladium(0) ($Pd(tpp)_4$) (2.03 g) was added to a mixture of (E)-1-chloro-7,11-dimethyl-3-methylene-6,10-dodecadien-4-yl phenyl sulfone (18.10 g, ~100% NMR) synthesized in the aforesaid Example 1, triphenylphosphine (1.86 g), tetrahydrofuran (125 ml), and methanol (125 ml) in a nitrogen atmosphere at a room temperature with stirring. The reaction mixture was stirred for 30 minutes at a room temperature, and then for 1.5 hours at 70° C. After cooling the reaction mixture, the reaction mixture was filtered off through celite, and eluted with diethyl ether. The diethyl ether solution was concentrated and then separated by silica gel column chromatography to obtain the target compounds, (3Z,6E)-(1-chloro-7,11-dimethyl-3,6,10-dodecatrien-3-yl)methyl phenyl sulfone and (3E,6E)-(1-chloro-7,11-dimethyl-3,6,10-dodecatrien-3-yl)methyl phenyl sulfone, with the following fractions: 4.80 g (~100% GC, ZE:EE=100:0), 5.09 g (~100% GC, ZE:EE=42:57), 2.86 g (~100% GC, ZE:EE=12.3:87.7), and 3.84 g (~100% GC, ZE:EE=2.3:97.7).

The isomerization from secondary sulfone compound to primary sulfone compound proceeded, the resulting two primary sulfone compounds were easily separated, and key intermediates for α-farnesene synthesis were obtained with high purity, as shown in Example 8 and the Examples below.

(3Z,6E)-(1-chloro-7,11-dimethyl-3,6,10-dodecatrien-3-yl)methyl phenyl sulfone

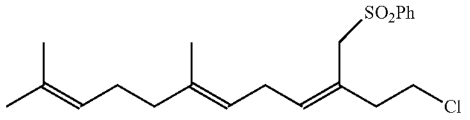

$C_{21}H_{29}ClO_2S$

Colorless Oil

IR (D-ATR): ν=2967, 2918, 2855, 1669, 1585, 1447, 1376, 1317, 1308, 1243, 1147, 1113, 1085, 902, 837, 746, 723, 689, 656, 614, 532 $cm^{-1}$.

$^1$H-NMR (500 MHz, $CDCl_3$): δ=1.48 (3H, br.s), 1.59 (3H, br.s), 1.67 (3H, br.s), 1.87-1.95 (2H, m), 1.98-2.04 (2H, m), 2.30 (2H, t, J=7.0 Hz), 2.67 (2H, dt, J=1.0, 6.7 Hz), 3.63 (2H, t, J=6.7 Hz), 3.89 (2H, s), 4.74-4.80 (1H, m), 5.01-5.07 (1H, m), 5.53 (1H, t, J=7.4 Hz), 7.53-7.59 (2H, m), 7.63-7.69 (1H, m), 7.86-7.92 (2H, m) ppm.

A 2D-NOESY (NOE: nuclear Overhauser effect) correlation was observed between signals of hydrogen atoms bonded to carbon atoms at the positions shown by the bidirectional arrows in the following chemical formula:

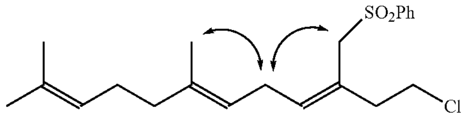

The stereochemistry (geometrical isomerism of the double bonds) of the target compound was verified from chemical shifts of the signals and patterns including the $^1$H-$^1$H coupling constant J in the aforesaid $^1$H-NMR, and also from the 2D-NOESY spectra correlation.

$^{13}$C-NMR (125 MHz, $CDCl_3$): δ=16.05, 17.66, 25.67, 26.50, 26.93, 39.01, 39.45, 42.82, 57.30, 120.53, 123.03, 123.99, 128.50, 129.21, 131.51, 133.82, 136.79, 136.92, 138.70 ppm.

(3E,6E)-(1-chloro-7,11-dimethyl-3,6,10-dodecatrien-3-yl)methyl phenyl sulfone

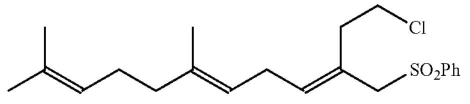

$C_{21}H_{29}ClO_2S$

Colorless Oil

IR (D-ATR): ν=2967, 2918, 2855, 1668, 1586, 1447, 1377, 1316, 1307, 1252, 1142, 1086, 887, 839, 742, 689, 657, 621, 531 $cm^{-1}$.

$^1$H-NMR (500 MHz, $CDCl_3$): δ=1.55 (3H, br.s), 1.60 (3H, br.s), 1.68 (3H, br.s), 1.90-1.97 (2H, m), 1.99-2.06 (2H, m), 2.69 (2H, t, J=7.1 Hz), 2.73 (2H, t, J=7.0 Hz), 3.61 (2H, t, J=6.9 Hz), 3.78 (2H, s), 4.80-4.86 (1H, m), 5.03-5.09 (1H, m), 5.19 (1H, t, J=7.4 Hz), 7.52-7.58 (2H, m), 7.62-7.67 (1H, m), 7.82-7.87 (2H, m) ppm.

A 2D-NOESY (NOE: nuclear Overhauser effect) correlation was observed between signals of hydrogen atoms bonded to carbon atoms at the positions shown by the bidirectional arrows in the following chemical formula:

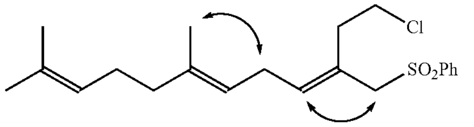

The stereochemistry (geometrical isomerism of the double bonds) of the target compound was verified from the 2D-NOESY spectra correlation, and chemical shift of the signals and patterns including the $^{1}H$-$^{1}H$ coupling constant J in the aforesaid $^{1}H$-NMR.

$^{13}C$-NMR (125 MHz, $CDCl_3$): δ=16.11, 17.69, 25.69, 26.56, 27.29, 32.62, 39.56, 42.42, 63.35, 120.40, 123.50, 123.98, 128.56, 128.98, 131.60, 133.63, 136.69, 138.05, 138.94 ppm.

Example 9: Synthesis of (3Z,6Z)-(1-chloro-7,11-dimethyl-3,6,10-dodecatrien-3-yl)methyl p-tolyl sulfone (When R=(Z)-3,7-dimethyl-2,6-octadienyl group, W=p-toluenesulfonyl Group, X=Cl, and Geometrical Isomerism of Double Bond of Position 3 is Z-Form in General Formula (D)) and (3E,6Z)-(1-chloro-7,11-dimethyl-3,6,10-dodecatrien-3-yl) methyl phenyl sulfone (When R=(Z)-3,7-dimethyl-2,6-octadienyl Group, W=p-toluenesulfonyl Group, X=Cl, and Geometrical Isomerism of Double Bond of Position 3 is E-Form in General Formula (D))

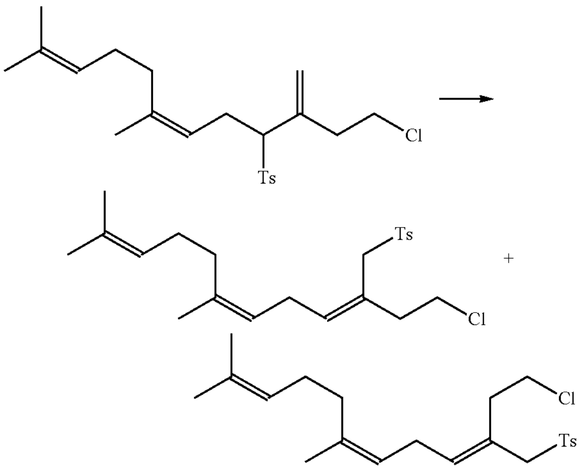

Tetrakis(triphenylphosphine)palladium(0) (0.15 g) was added to a mixture of (Z)-1-chloro-7,11-dimethyl-3-methylene-6,10-dodecadien-4-yl p-tolyl sulfone (1.07 g, ~100% NMR) synthesized in a process similar to the aforesaid Example 2, triphenylphosphine (0.10 g), tetrahydrofuran (10 ml), and methanol (10 ml) in a nitrogen atmosphere at a room temperature with stirring. The reaction mixture was stirred for 2.1 hours at 70 to 75° C., and then for 14 hours at a room temperature. The reaction mixture was cooled, and then eluted with water and diethyl ether. The crude product obtained by concentrating the diethyl ether solution was a 2.0:42.4:55.6 ($^{1}H$-NMR) isomeric mixture of starting material, (Z)-1-chloro-7,11-dimethyl-3-methylene-6,10-dodecadien-4-yl p-tolyl sulfone:target compound, ZZ-isomer (3Z,6Z)-(1-chloro-7,11-dimethyl-3,6,10-dodecatrien-3-yl) methyl p-tolyl sulfone:target compound, EZ-isomer (3E,6Z)-(1-chloro-7,11-dimethyl-3,6,10-dodecatrien-3-yl) methyl p-tolyl sulfone. The isomeric mixture was separated by silica gel column chromatography to obtain the target compounds, (3Z,6Z)-(1-chloro-7,11-dimethyl-3,6,10-dodecatrien-3-yl)methyl p-tolyl sulfone and (3E,6Z)-(1-chloro-7,11-dimethyl-3,6,10-dodecatrien-3-yl)methyl p-tolylsulfone, in amounts of 0.34 g (89.5% NMR, ZZ:EZ=100:0 GC), 0.22 g (~100% NMR, ZZ:EZ=42.2:57.8 GC to 43.2:56.8 NMR), 0.21 g (~100% NMR, ZZ:EZ=9.5:90.5 GC to 9.5:90.5 NMR), and 0.19 g (~100% NMR, ZZ:EZ=0:100 NMR) (isomer total yield 96%).

(3Z,6Z)-(1-chloro-7,11-dimethyl-3,6,10-dodecatrien-3-yl)methyl p-tolyl sulfone

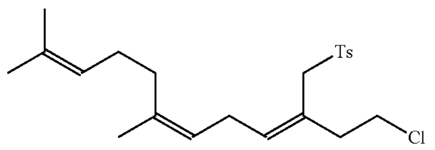 [SMILES: CC(C)=CCC/C(C)=C\C/C=C(/CCCl)CS(=O)(=O)c1ccc(C)cc1]

$C_{22}H_{31}ClO_2S$

Colorless Oil

IR (D-ATR): ν=3030, 2965, 2925, 2856, 1597, 1495, 1449, 1407, 1377, 1317, 1303, 1292, 1242, 1147, 1115, 1087, 951, 901, 816, 729, 671 $cm^{-1}$.

$^{1}H$-NMR (500 MHz, $CDCl_3$): δ=1.60 (3H, br.s), 1.62 (3H, q-like, J=~1.2 Hz), 1.69 (3H, q-like, J=~1.2 Hz), 1.89 (2H, t-like, J=~8 Hz), 1.99 (2H, q-like, J=~7.3 Hz), 2.28 (2H, t, J=7.0 Hz), 2.45 (3H, s), 2.67 (2H, dt-like, J=~1, ~7 Hz), 3.62 (2H, t, J=6.8 Hz), 3.86 (2H, s), 4.73 (1H, t-like, J=~7 Hz), 5.01-5.08 (1H, m), 5.50 (1H, t, J=7.3 Hz), 7.32-7.38 (2H, m), 7.74-7.89 (2H, m) ppm.

A 2D-NOESY (NOE: nuclear Overhauser effect) correlation was observed between signals of hydrogen atoms bonded to carbon atoms at the positions shown by the bidirectional arrows in the following chemical formula, and stereochemistry (double bond geometrical isomerism) was determined.

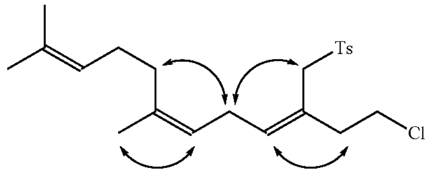 [SMILES: CC(C)=CCC/C(C)=C\C/C=C(/CCCl)CS(=O)(=O)c1ccc(C)cc1]

The stereochemistry (geometrical isomerism of the double bonds) of the target compound was verified from the 2D-NOESY spectra correlation, and chemical shift of the signals and patterns including the $^{1}H$-$^{1}H$ coupling constant J in the aforesaid $^{1}H$-NMR.

$^{13}$C-NMR (125 MHz, $CDCl_3$): δ=17.67, 21.62, 23.24, 25.73, 26.33, 26.84, 31.82, 39.07, 42.82, 57.35, 121.42, 123.24, 123.92, 128.55, 129.82, 131.79, 135.80, 136.79 (2C overlapped), 144.83 ppm.

(3E,6Z)-(1-chloro-7,11-dimethyl-3,6,10-dodecatrien-3-yl)methyl p-tolyl sulfone

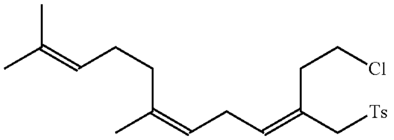 [SMILES: CC(C)=CCC/C(C)=C\C/C=C(\CCCl)CS(=O)(=O)c1ccc(C)cc1]

$C_{22}H_{31}ClO_2S$

Colorless Oil

IR (D-ATR): ν=3032, 2965, 2924, 2856, 1597, 1495, 1447, 1404, 1377, 1315, 1302, 1255, 1184, 1145, 1116, 1087, 1039, 1019, 886, 816, 731, 673 $cm^{-1}$.

$^1$H-NMR (500 MHz, $CDCl_3$): δ=1.59 (3H, br.s), 1.66 (3H, q-like, J=~1.3 Hz), 1.67 (3H, q-like, J=~0.8 Hz), 1.92-2.05 (4H, m), 2.44 (3H, s), 2.67 (2H, br.t, J=~7 Hz), 2.71 (2H, t, J=6.9 Hz), 3.60 (2H, t, J=7.0 Hz), 3.74 (2H, s), 4.81 (1H, t-like, J=~7 Hz), 5.02-5.09 (1H, m), 5.14 (1H, t, J=7.4 Hz), 7.32 (2H, d, J=8.2 Hz), 7.69 (2H, dt, J=8.2, 1.9 Hz) ppm.

$^{13}$C-NMR (125 MHz, $CDCl_3$): δ=17.63, 21.60, 23.27, 25.69, 26.37, 27.14, 31.91, 32.58, 42.45, 63.42, 121.31, 123.60, 123.88, 128.60, 129.58, 131.84, 135.09, 136.65, 138.83, 144.56 ppm.

Example 10: Synthesis of (3Z,6E)-(1-bromo-7,11-dimethyl-3,6,10-dodecatrien-3-yl)methyl phenyl sulfone (When R=(E)-3,7-dimethyl-2,6-octadienyl Group, W=Benzenesulfonyl Group, X=Br, and Geometrical Isomerism of Double Bond of Position 3 is Z-Form in General Formula (D))

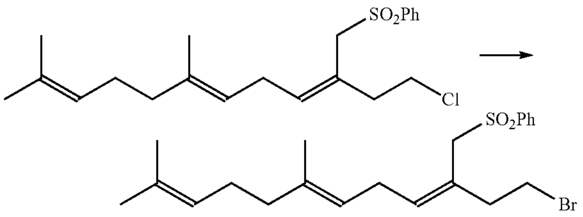

A mixture of (3Z,6E)-(1-chloro-7,11-dimethyl-3,6,10-dodecatrien-3-yl)methyl phenyl sulfone (2.24 g, ~100% NMR, ZE:EE=100:0) synthesized in the aforesaid Example 8, bromoethane (5.00 g), sodium bromide (0.200 g), and N-methyl-2-pyrrolidone (20 ml) was stirred in a nitrogen atmosphere for 11 hours at 60 to 72° C. The reaction mixture was cooled, and then water was added. The reaction mixture was extracted with ethyl acetate. The ethyl acetate solution was subjected to ordinary work-up, i.e., washing, drying, and concentration, and then purified by silica gel column chromatography to obtain the target compound, (3Z,6E)-(1-bromo-7,11-dimethyl-3,6,10-dodecatrien-3-yl)methyl phenyl sulfone (1.84 g, including a trace amount of the starting material, chloride, ~93% NMR, yield 81%).

(3Z,6E)-(1-bromo-7,11-dimethyl-3,6,10-dodecatrien-3-yl)methyl phenyl sulfone

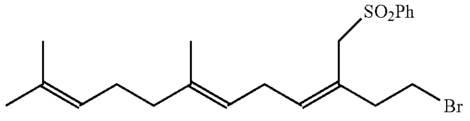

$C_{21}H_{29}BrO_2S$

Yellowish Oil

IR (D-ATR): ν=3061, 2967, 2917, 2855, 1585, 1447, 1376, 1317, 1307, 1145, 1109, 1085, 746, 723, 688, 611, 590, 532 $cm^{-1}$.

$^1$H-NMR (500 MHz, $CDCl_3$): δ=1.48 (3H, br.s), 1.58 (3H, br.s), 1.67 (3H, q-like, J=~1 Hz), 1.87-1.95 (2H, m), 1.98-2.04 (2H, m), 2.30 (2H, t, J=7.1 Hz), 2.67 (2H, dt-like, J=~1, 7.0 Hz), 3.48 (2H, t, J=7.0 Hz), 3.89 (2H, s), 4.74-4.81 (1H, m), 5.01-5.07 (1H, m), 5.53 (1H, t, J=7.3 Hz), 7.53-7.59 (2H, m), 7.63-7.69 (1H, m), 7.87-7.92 (2H, m) ppm.

$^{13}$C-NMR (125 MHz, $CDCl_3$): δ=16.06, 17.66, 25.67, 26.50, 26.92, 31.08, 39.14, 39.45, 57.14, 120.49, 123.74, 123.99, 128.49, 129.21, 131.49, 133.83, 136.82, 136.87, 138.70 ppm.

GC-MS (EI, 70 eV): 41, 69, 105 (base peak), 133, 175, 213, 239, 282.

Example 11: Synthesis of (Z)-(1-chloro-7-methyl-3,6-octadienen-3-yl)methyl p-tolyl sulfone (When R=3-methyl-2-butenyl group, W=p-toluenesulfonyl group, X=Cl, and Geometrical Isomerism Of Double Bond Of Position 3 is Z-Form in General Formula (D)) and (E)-(1-chloro-7-methyl-3,6-octadienen-3-yl)methyl p-tolyl sulfone (When R=3-methyl-2-butenyl Group, W=p-toluenesulfonyl Group, X=Cl, and Geometrical Isomerism of Double Bond of Position 3 is E-Form in General Formula (D))

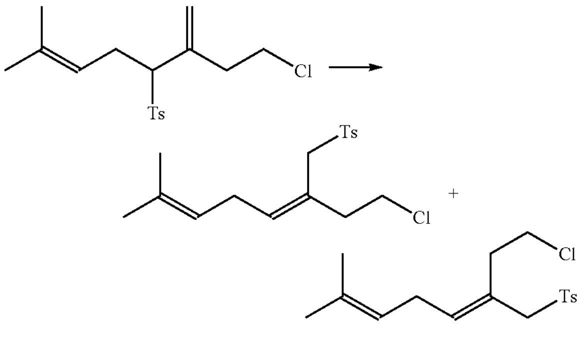

Tetrakis(triphenylphosphine)palladium(0) (0.500 g) was added to a mixture of 1-chloro-7-methyl-3-methylen-6-octen-4-yl p-tolyl sulfone (2.70 g, >~95% NMR) synthesized in the aforesaid Example 3, tetrahydrofuran (30 ml), and methanol (8 ml) in a nitrogen atmosphere at a room temperature with stirring. The reaction mixture was stirred for 25 minutes at 50° C., and then refluxed with stirring at 70° C. Diethyl ether was added. The reaction mixture was filtered off through celite, concentrated, and then separated by silica gel column chromatography to obtain the target compounds, Z-isomer (Z)-(1-chloro-7-methyl-3,6-octadienen-3-yl)methyl p-tolyl sulfone and E-isomer (E)-(1-chloro-7-methyl-3,6-octadienen-3-yl)methyl p-tolyl sulfone, in amounts of 0.740 g (~90.5% GC, Z:E=100:0), 0.120 g (83.0% GC, Z:E=34.6:65.4), and 0.96 g (86.7% GC, Z:E=0:100) (isomer total yield 67%).

(Z)-(1-Chloro-7-methyl-3,6-octadienen-3-yl)methyl p-tolyl sulfone

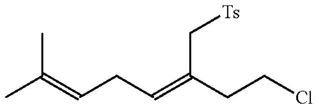 [SMILES: CC(C)=CC/C=C(/CCCl)CS(=O)(=O)c1ccc(C)cc1]

$C_{17}H_{23}ClO_2S$

Colorless Oil

IR (D-ATR): ν=3031, 2968, 2924, 2875, 1597, 1494, 1407, 1377, 1316, 1303, 1292, 1244, 1146, 1117, 1087, 1019, 816, 728, 672, 518 $cm^{-1}$.

$^1H$-NMR (500 MHz, $CDCl_3$): δ=1.48 (3H, br.s), 1.61 (3H, q-like, J=~1 Hz), 2.29 (2H, t, J=7.2 Hz), 2.44 (3H, s), 2.66 (2H, tq-like, J=6.7, 1.2 Hz), 3.62 (2H, t, J=6.9 Hz), 3.86 (2H, s), 4.70-4.77 (1H, m), 5.50 (1H, t, J=7.4 Hz), 7.33-7.37 (2H, m), 7.73-7.78 (2H, m) ppm.

$^{13}C$-NMR (125 MHz, $CDCl_3$): δ=17.60, 21.60, 25.50, 27.02, 39.00, 42.82, 57.33, 120.79, 123.19, 128.49, 129.79, 133.01, 135.74, 136.66, 144.83 ppm.

GC-MS (EI, 70 eV): 41, 65, 91 (base peak), 107, 122, 129, 145, 155, 170.

(E)-(1-Chloro-7-methyl-3,6-octadienen-3-yl)methyl p-tolyl sulfone

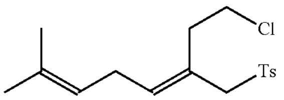 [SMILES: CC(C)=CC/C=C(\CCCl)CS(=O)(=O)c1ccc(C)cc1]

$C_{17}H_{23}ClO_2S$

Colorless Oil

IR (D-ATR): ν=3031, 2970, 2924, 2877, 1597, 1494, 1448, 1405, 1377, 1314, 1302, 1253, 1141, 1118, 1087, 1019, 816, 730, 673, 517 $cm^{-1}$.

$^1H$-NMR (500 MHz, $CDCl_3$): δ=1.54 (3H, br.s), 1.65 (3H, q-like, J=~1 Hz), 2.43 (3H, s), 2.66 (2H, t, J=7.2 Hz), 2.71 (2H, t, J=7.0 Hz), 3.59 (2H, t, J=7.0 Hz), 3.74 (2H, s), 4.78-4.83 (1H, m), 5.16 (1H, t, J=7.6 Hz), 7.30-7.34 (2H, m), 7.67-7.72 (2H, m) ppm.

$^{13}C$-NMR (125 MHz, $CDCl_3$): δ=17.66, 21.57, 25.54, 27.34, 32.58, 42.42, 63.35, 120.66, 123.51, 128.54, 129.54, 132.85, 135.04, 138.67, 144.55 ppm.

GC-MS (EI, 70 eV): 41, 65, 91, 107, 122, 129, 155, 171 (base peak).

Example 12: Synthesis of (Z)-(1-chloro-7-methyl-3,6-octadienen-3-yl)methyl phenyl sulfone (When R=3-methyl-2-butenyl Group, W=benzenesulfonyl Group, X=Cl, and Geometrical Isomerism of Double Bond of Position 3 is Z-Form in General Formula (D)) and (E)-(1-chloro-7-methyl-3,6-octadienen-3-yl)methyl phenyl sulfone (When R=3-methyl-2-butenyl Group, W=benzenesulfonyl Group, X=Cl, and Geometrical Isomerism of Double Bond of Position 3 is E-Form in General Formula (D))

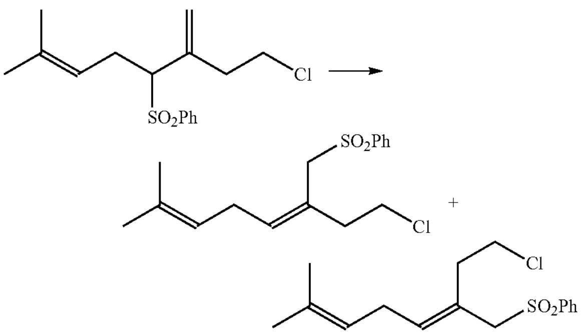

Tetrakis(triphenylphosphine)palladium(0) (18.0 g) was added to a mixture of 7-methyl-3-methylen-6-octen-4-yl phenyl sulfone (100.0 g, ~100% GC) synthesized in the aforesaid Example 4, tetrahydrofuran (500 ml), and methanol (125 ml) in a nitrogen atmosphere at a room temperature with stirring. The reaction mixture was refluxed with stirring for 3.5 hours at 70° C., and then stirred for 19 hours at a room temperature. Diethyl ether was added. The reaction mixture was filtered off through celite, concentrated, and then separated by silica gel column chromatography to obtain the target compounds, Z-isomer (Z)-(1-chloro-7-methyl-3,6-octadienen-3-yl)methyl phenyl sulfone and E-isomer (E)-(1-chloro-7-methyl-3,6-octadienen-3-yl) methyl phenyl sulfone, in amounts of 14.85 g (Z:E=100:0 to 95.7:4.3), 32.55 g (Z:E=70.6:29.4 to 32.3:67.7), and 16.15 g (Z:E=10.9:89.1 to 0:100) (isomer total yield 66%).

(Z)-(1-Chloro-7-methyl-3,6-octadienen-3-yl)methyl phenyl sulfone

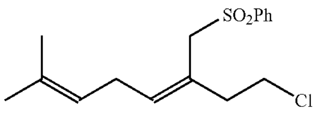

$C_{16}H_{21}ClO_2S$

Colorless Waxy Solid

Melting point: 36.4° C. (DSC)

IR (D-ATR): ν=3063, 2966, 2927, 2873, 1585, 1479, 1447, 1317, 1308, 1147, 1085, 903, 745, 722, 689, 655, 614, 533 $cm^{-1}$.

$^1H$-NMR (500 MHz, $CDCl_3$): δ=1.49 (3H, br.s), 1.62 (3H, s-like), 2.30 (2H, t, J=7.1 Hz), 2.67 (2H, tq-like, J=6.9, ~1 Hz), 3.62 (2H, t, J=6.9 Hz), 3.89 (2H, s), 4.73-4.78 (1H, m), 5.53 (1H, t, J=7.3 Hz), 7.52-7.59 (2H, m), 7.63-7.69 (1H, m), 7.86-7.91 (2H, m) ppm.

$^{13}C$-NMR (125 MHz, $CDCl_3$): δ=17.70, 25.51, 27.05, 39.03, 42.81, 57.32, 120.70, 123.04, 128.49, 129.22, 133.15, 133.82, 136.86, 138.73 ppm.

(E)-(1-Chloro-7-methyl-3,6-octadienen-3-yl)methyl phenyl sulfone

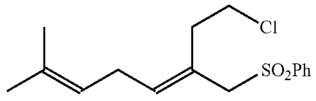

$C_{16}H_{21}ClO_2S$
Colorless Oil

IR (D-ATR): ν=3062, 2970, 2916, 1712, 1585, 1479, 1447, 1406, 1377, 1307, 1142, 1085, 743, 689, 655, 620, 531 $cm^{-1}$.

$^1H$-NMR (500 MHz, $CDCl_3$): δ=1.55 (3H, br.s), 1.65 (3H, s-like), 2.66 (2H, t, J=7.1 Hz), 2.72 (2H, t, J=6.9 Hz), 3.60 (2H, t, J=7.0 Hz), 3.77 (2H, s), 4.78-4.84 (1H, m), 5.17 (1H, t, J=7.5 Hz), 7.51-7.58 (2H, m), 7.61-7.67 (1H, m), 7.81-7.85 (2H, m) ppm.

$^{13}C$-NMR (125 MHz, $CDCl_3$): δ=17.71, 25.56, 27.38, 32.58, 42.42, 63.32, 120.58, 123.39, 128.55, 128.96, 132.96, 133.60, 138.02, 138.89 ppm.

Example 13: Synthesis of (Z)-(8-chloro-2-methyl-1,5-octadienen-6-yl)methyl phenyl sulfone (When R=3-methyl-3-butenyl Group, W=benzenesulfonyl Group, X=Cl, and Geometrical Isomerism of Double Bond of Position 3 is Z-Form in General Formula (D)) and (E)-(8-chloro-2-methyl-1,5-octadienen-6-yl)methyl phenyl sulfone (When R=3-methyl-3-butenyl Group, W=Benzenesulfonyl Group, X=Cl, and Geometrical Isomerism of Double Bond of Position 3 is E-Form in General Formula (D))

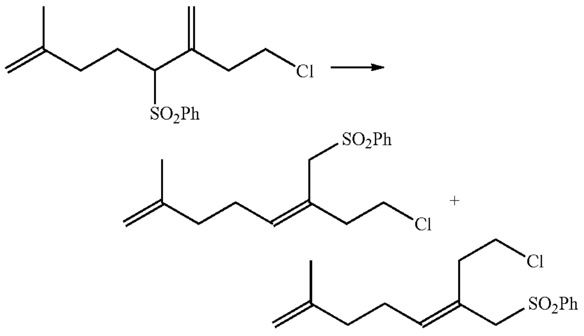

Tetrakis(triphenylphosphine)palladium(0) (0.840 g) was added to a mixture of 8-chloro-2-methyl-6-methylen-1-octen-5-yl phenyl sulfone (4.58 g, 96.0% GC, including 4.3% of corresponding bromide: 8-bromo-2-methyl-6-methylen-1-octen-5-yl phenyl sulfone) synthesized in the aforesaid Example 5, tetrahydrofuran (60 ml), and methanol (16 ml) in a nitrogen atmosphere at a room temperature with stirring. The reaction mixture was refluxed with stirring for 3 hours at 70° C., and then stirred for 18 hours at a room temperature. Diethyl ether was added. The reaction mixture was filtered off through celite, concentrated, and then separated by silica gel column chromatography to obtain the target compounds, Z-isomer (Z)-(8-chloro-2-methyl-1,5-octadienen-6-yl)methyl phenyl sulfone and E-isomer (E)-(8-chloro-2-methyl-1,5-octadienen-6-yl)methyl phenyl sulfone, in amounts of 1.67 g (84.2 to 94.3% GC, Z:E=100:0 to 96.4:3.6), 1.51 g (95.6% GC, Z:E=32.9:67.1), and 1.22 g (93.0% GC, Z:E=0:100) (isomer total yield 90%).

(Z)-(8-Chloro-2-methyl-1,5-octadienen-6-yl)methyl phenyl sulfone

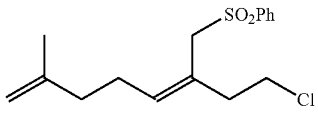

$C_{16}H_{21}ClO_2S$
Colorless Oil

IR (D-ATR): ν=3070, 2967, 2934, 1649, 1585, 1478, 1447, 1317, 1307, 1147, 1085, 891, 744, 725, 689, 655, 614, 532 $cm^{-1}$.

$^1H$-NMR (500 MHz, $CDCl_3$): δ=1.61 (3H, br.s), 1.71-1.77 (2H, m), 1.79-1.84 (2H, m), 2.67 (2H, dt, J=1.0, 6.7 Hz), 3.62 (2H, t, J=6.7 Hz), 3.88 (2H, s), 4.51-4.53 (1H, m), 4.66-4.68 (1H, m), 5.57 (1H, t, J=7.0 Hz), 7.54-7.58 (2H, m), 7.64-7.68 (1H, m), 7.87-7.91 (2H, m) ppm.

$^{13}C$-NMR (125 MHz, $CDCl_3$): δ=22.34, 26.11, 36.59, 39.00, 42.86, 57.35, 110.42, 123.33, 128.49, 129.20, 133.82, 137.53, 138.68, 144.45 ppm.

GC-MS (EI, 70 eV): 39, 55, 77 (base peak), 93,109,129, 155, 171.

(E)-8-Chloro-2-methyl-1,5-octadienen-6-yl)methyl phenyl sulfone $SO_2Ph$

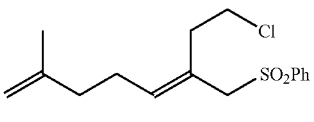

$C_{16}H_{21}ClO_2S$
Colorless Oil

IR (D-ATR): ν=3070, 2968, 2932, 1735, 1649, 1586, 1479, 1447, 1406, 1375, 1307, 1254, 1142, 1085, 889, 742, 689, 656, 621, 532 $cm^{-1}$.

$^1H$-NMR (500 MHz, $CDCl_3$): δ=1.66 (3H, br.s), 1.85-1.90 (2H, m), 2.11-2.17 (2H, m), 2.72 (2H, t, J=6.9 Hz), 3.62 (2H, t, J=6.9 Hz), 3.78 (2H, d, J=0.6 Hz), 4.55-4.48 (1H, m), 4.67-4.70 (1H, m), 5.25 (1H, t, J=~7.2 Hz), 7.53-7.58 (2H, m), 7.64-7.68 (1H, m), 7.83-7.87 (2H, m) ppm.

$^{13}C$-NMR (125 MHz, $CDCl_3$): δ=22.34, 26.40, 32.59, 36.72, 42.40, 63.28, 110.52, 123.79, 128.49, 129.03, 133.68, 138.19, 139.61, 144.45 ppm.

GC-MS (EI, 70 eV): 39, 55, 77 (base peak), 107, 129, 155, 171.

Example 14: Synthesis of (3Z,6E)-(1-chloro-7-phenyl-3,6-heptadien-3-yl)methyl p-tolyl sulfone (When R=(E)-cinnamyl Group, W=p-toluenesulfonyl Group, X=Cl, and Geometrical Isomerism of Double Bond of Position 3 is Z-Form in General Formula (D)) and (3E,6E)-(1-chloro-7-phenyl-3,6-heptadien-3-yl)methyl p-tolyl sulfone (When R=(E)-cinnamyl Group, W=p-toluenesulfonyl Group, X=Cl, and Geometrical Isomerism of Double Bond of Position 3 is E-Form in General Formula (D))

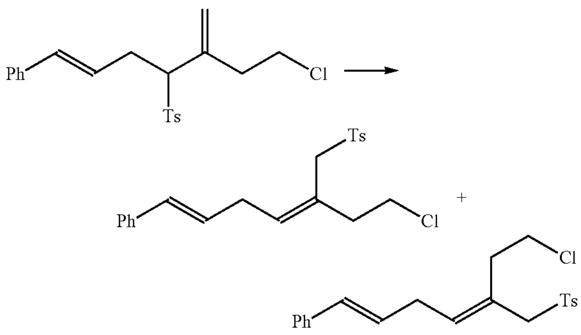

Tetrakis(triphenylphosphine)palladium(0) (3.42 g) was added to a mixture of crude (E)-7-chloro-5-methylene-1-phenyl-1-hepten-4-yl p-tolyl sulfone (22.2 g) synthesized in the aforesaid Example 6, triphenylphosphine (2.33 g), tetrahydrofuran (300 ml), and methanol (100 ml) in a nitrogen atmosphere at a room temperature with stirring. The reaction mixture was refluxed with stirring for 12 hours at 70° C. The reaction mixture was filtered off through celite, concentrated, and then separated by silica gel column chromatography to obtain the target compounds, Z-isomer (3Z,6E)-(1-chloro-7-phenyl-3,6-heptadien-3-yl)methyl p-tolyl sulfone and E-isomer (3E,6E)-(1-chloro-7-phenyl-3,6-heptadien-3-yl)methyl p-tolyl sulfone, in amounts of 6.17 g (Z:E=95.6:4.4), 4.76 g (Z:E=~40:60), and 4.68 g (Z:E=0:100) (isomer total yield 74%).

(3Z,6E)-(1-chloro-7-phenyl-3,6-heptadien-3-yl) methyl p-tolyl sulfone

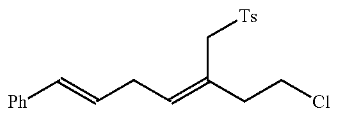 [SMILES: Cc1ccc(S(=O)(=O)C/C(=C\C/C=C/c2ccccc2)CCCl)cc1]

$C_{21}H_{23}ClO_2S$

Colorless Oil

IR (D-ATR): ν=3026, 2961, 2923, 1597, 1494, 1448, 1315, 1302, 1145, 1118, 1086, 967, 816, 735, 694, 671, 635, 603, 516 $cm^{-1}$.

$^1$H-NMR (500 MHz, $CDCl_3$): δ=2.40 (3H, s), 2.62 (2H, br.t, J=~6.8 Hz), 2.73 (2H, dt-like, J=1.0, 6.7 Hz), 3.67 (2H, t, J=6.7 Hz), 3.91 (2H, s), 5.69 (1H, t, J=7.4 Hz), 5.88 (1H, dt, J=~15.8, 6.3 Hz), 6.24 (1H, dt-like, J=16.1, ~1.6 Hz), 7.18-7.23 (1H, m), 7.25-7.32 (4H, m), 7.35 (2H, d-like, J=~8.5 Hz), 7.78 (2H, dt-like, J=8.2, ~1.8 Hz) ppm.

$^{13}$C-NMR (125 MHz, $CDCl_3$): δ=21.61, 31.34, 39.07, 42.78, 57.15, 124.73, 125.97, 126.63, 127.21, 128.45, 128.49, 129.87, 131.02, 134.85, 135.77, 137.13, 144.93 ppm.

(3E,6E)-(1-chloro-7-phenyl-3,6-heptadien-3-yl) methyl p-tolyl sulfone

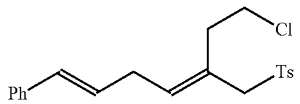 [SMILES: Cc1ccc(S(=O)(=O)C/C(=C/C/C=C/c2ccccc2)CCCl)cc1]

$C_{21}H_{23}ClO_2S$

Yellow Solid

IR (D-ATR): ν=3026, 2993, 2969, 2953, 2925, 1596, 1493, 1444, 1405, 1312, 1301, 1251, 1217, 1177, 1139, 1111, 1084, 962, 815, 744, 725, 694, 657, 631, 532, 510 $cm^{-1}$.

$^1$H-NMR (500 MHz, $CDCl_3$): δ=2.33 (3H, s), 2.78 (2H, br.t, J=~6.8 Hz), 2.92 (2H, dt-like, J=1.3, 7.1 Hz), 3.65 (2H, t, J=6.8 Hz), 3.81 (2H, s-like), 5.33 (1H, t, J=7.5 Hz), 5.94 (1H, dt, J=15.9, 6.7 Hz), 6.24 (1H, dt-like, J=15.9, 1.5 Hz), 7.20-7.38 (7H, m), 7.71 (2H, dt-like, J=8.2, ~1.9 Hz) ppm.

$^{13}$C-NMR (125 MHz, $CDCl_3$): δ=21.52, 31.68, 32.53, 42.47, 63.31, 125.06, 125.99, 126.65, 127.27, 128.54, 128.56, 129.66, 131.03, 135.00, 136.98, 137.18, 144.73 ppm.

Example 15: Synthesis of (Z)-(1-chloro-3-dodecen-3-yl)methyl p-tolyl sulfone (When R=n-octyl Group, W=p-toluenesulfonyl Group, X=Cl, and Geometrical Isomerism of Double Bond of Position 3 is Z-Form in General Formula (D)) and (E)-(1-chloro-3-dodecen-3-yl)methyl p-tolyl sulfone (When R=n-octyl Group, W=p-toluenesulfonyl Group, X=Cl, and Geometrical Isomerism of Double Bond of Position 3 is E-Form in General Formula (D))

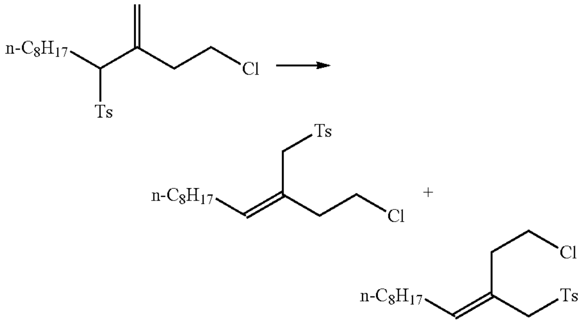

Tetrakis(triphenylphosphine)palladium(0) (1.20 g) was added to a mixture of 1-chloro-3-methylenedodecan-4-yl p-tolyl sulfone (7.720 g) synthesized in the aforesaid Example 7, triphenylphosphine (0.820 g), tetrahydrofuran (80 ml), and methanol (20 ml) in a nitrogen atmosphere at a room temperature with stirring. The reaction mixture was refluxed with stirring for 5 hours at 70° C. Diethyl ether was added to the reaction mixture. The reaction mixture was filtered off through celite, concentrated, and then separated by silica gel column chromatography to obtain the target compounds, Z-isomer (Z)-(1-chloro-3-dodecen-3-yl)methyl p-tolyl sulfone and E-isomer (E)-(1-chloro-3-dodecen-3-yl) methyl p-tolyl sulfone, in amounts of 2.40 g (Z:E=100:0), 1.30 g (Z:E=30.2:69.8), and 2.83 g (Z:E=0:100) (isomer total yield 86%).

(Z)-(1-Chloro-3-dodecen-3-yl)methyl p-tolyl sulfone

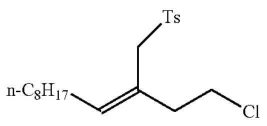

$C_{20}H_{31}ClO_2S$

Colorless Waxy Solid

Melting point: 50.7° C. (DSC)

IR (D-ATR): ν=3067, 3045, 2962, 2919, 2849, 1599, 1494, 1468, 1451, 1435, 1413, 1386, 1311, 1302, 1292, 1256, 1245, 1175, 1149, 1131, 1087, 1020, 945, 918, 893, 812, 738, 705, 654, 640, 609, 550, 522, 511 $cm^{-1}$.

$^1$H-NMR (500 MHz, $CDCl_3$): δ=0.88 (3H, t, J=6.8 Hz), 1.05-1.32 (12H, m), 1.56-1.62 (2H, m), 2.45 (3H, s), 2.66 (2H, dt, J=1.0, 6.8 Hz), 3.62 (2H, t, J=6.7 Hz), 3.84 (2H, s), 5.55 (1H, t, J=7.3 Hz), 7.34 (2H, d-like, J=~8 Hz), 7.75 (2H, dt, J=~8, 1.9 Hz) ppm.

$^{13}$C-NMR (125 MHz, $CDCl_3$): δ=14.09, 21.63, 22.63, 28.14, 28.92, 29.17, 29.20, 29.34, 31.82, 38.99, 42.93, 57.28, 122.97, 128.51, 129.74, 135.78, 138.33, 144.76 ppm.

GC-MS (EI, 70 eV): 41, 69, 77, 91, 109, 130, 157, 178, 214 (base peak), 249, 277, 327, 355.

(E)-(1-Chloro-3-dodecen-3-yl)methyl p-tolyl sulfone

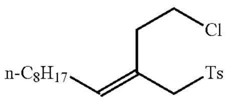

$C_{20}H_{31}ClO_2S$

Colorless Waxy Solid

Melting point: 37.3° C. (DSC)

IR (D-ATR): ν=2987, 2954, 2921, 2871, 2851, 1598, 1494, 1469, 1449, 1431, 1406, 1384, 1309, 1301, 1260, 1246, 1177, 1144, 1125, 1087, 1020, 946, 920, 881, 815, 775, 720, 704, 656, 632, 620, 540, 510 $cm^{-1}$.

$^1$H-NMR (500 MHz, $CDCl_3$): δ=0.88 (3H, t, J=7.1 Hz), 1.12-1.32 (12H, m), 1.94-2.02 (2H, m), 2.44 (3H, s), 2.69 (2H, t, J=7.1 Hz), 3.59 (2H, t, J=7.1 Hz), 3.75 (2H, s), 5.25 (1H, t, J=7.3 Hz), 7.33 (2H, d-like, J=~8 Hz), 7.71 (2H, dt, J=8.4, 1.9 Hz) ppm.

$^{13}$C-NMR (125 MHz, $CDCl_3$): δ=14.10, 21.62, 22.66, 28.32, 29.00, 29.17, 29.19, 29.40, 31.86, 32.56, 42.51, 63.45, 123.49, 128.52, 129.61, 135.26, 140.36, 144.59 ppm.

GC-MS (EI, 70 eV): 41, 69, 77, 91, 109, 139, 157, 178, 214 (base peak), 249, 277, 303, 341.

Examples: Synthesis of Halide Compound of the Following General Formula (B)

(B)

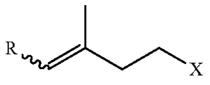

Example 16: Synthesis of (6E,9E)-12-chloro-2,6,10-trimethyl-2,6,9-dodecatriene (When R=(E)-3,7-dimethyl-2,6-octadienyl Group, X═Cl, and Geometrical Isomerism of Double Bond of Position 9 is E-Form in General Formula (B))

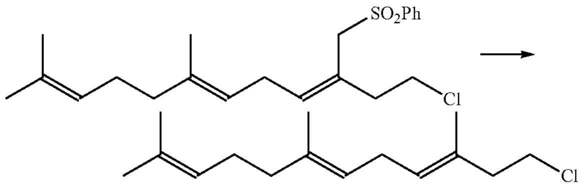

1.7 M Lithium triethylborohydride in tetrahydrofuran (6.95 ml) was poured for 5 minutes into a mixture of (3Z,6E)-(1-chloro-7,11-dimethyl-3,6,10-dodecatrien-3-yl) methyl phenyl sulfone (2.50 g, 100% ZE) synthesized in the aforesaid Example 8, 1,3-bis(diphenylphosphino)propane palladium(II) chloride (0.195 g), and tetrahydrofuran (70 ml) in a nitrogen atmosphere under ice cooling with stirring. The reaction mixture was stirred for 65 minutes under ice cooling, then an aqueous solution (42 g) of 12.5% sodium hydroxide was added dropwise, and then 35% aqueous hydrogen peroxide (4.73 g) was added dropwise. Water was added to the reaction mixture, and the reaction mixture was extracted with n-hexane. The n-hexane solution was subjected to ordinary work-up, i.e., washing, drying, and concentration to obtain a crude product.

The crude product was a 79.5:20.5 mixture of the target compound, (6E,9E)-12-chloro-2,6,10-trimethyl-2,6,9-dodecatriene, and an E-p-isomer, (E)-(12-chloro-2,6-dimethyl-10-methylene-2,6-dodecadiene, formed by a desulfonation reaction accompanying allylic rearrangement.

The crude product was separated by silica gel column chromatography to obtain the target compound, (6E,9E)-12-chloro-2,6,10-trimethyl-2,6,9-dodecatriene, in amounts of 0.610 g (97.7% GC, EE-α:E-β=72.8:27.2 GC) and 0.550 g (97.3% GC, target compound: E-β-isomer=87.8:12.2 GC) (isomer total yield 73%). Thus, the purity of isomers of the target compound may be improved by means for purification such as chromatography.

(6E,9E)-12-Chloro-2,6,10-trimethyl-2,6,9-dodecatriene

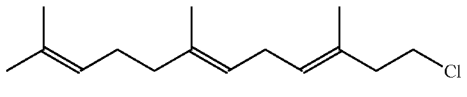 [SMILES: CC(C)=CCC/C(C)=C/C/C=C(\C)CCCl]

$C_{15}H_{25}Cl$

Colorless Oil

IR (D-ATR): ν=2967, 2916, 2856, 1670, 1450, 1382, 1325, 1294, 1246, 1151, 1108, 984, 935, 888, 834, 727, 661 $cm^{-1}$.

$^1$H-NMR (500 MHz, $CDCl_3$): δ=1.60 (3H, s), 1.62 (3H, q-like, J=~1 Hz), 1.65 (3H, q-like, J=~1 Hz), 1.68 (3H, q-like, J=~1 Hz), 1.95-2.01 (2H, m), 2.03-2.11 (2H, m), 2.44 (2H, t-like, J=7 Hz), 2.71 (2H, t-like, J=~7 Hz), 3.57 (2H, t, J=7.4 Hz), 5.07-5.12 (2H, m), 5.19-5.24 (1H, m) ppm.

$^{13}$C-NMR (125 MHz, $CDCl_3$): δ=15.78, 16.06, 17.68, 25.69, 26.66, 26.95, 39.64, 42.63, 43.20, 122.51, 124.25, 126.70, 130.90, 131.38, 135.43 ppm.

GC-MS (EI, 70 eV): 41, 55, 69, 81, 93, 107, 123 (base peak), 135, 157, 171, 183, 197, 211, 225, 240 ($M^+$).

Comparative Examples: E-p-isomer: (E)-12-chloro-2,6-dimethyl-10-methylene-2,6-dodecadiene synthesized separately

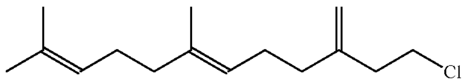 [SMILES: C=C(CCCl)CC/C=C(\C)CCC=C(C)C]

$C_{15}H_{25}Cl$

Colorless Oil

IR (D-ATR): ν=2965, 2925, 2855, 1646, 1448, 1377, 1325, 1300, 1242, 1152, 1108, 984, 895, 834, 739, 661 $cm^{-1}$.

$^1$H-NMR (500 MHz, $CDCl_3$): δ=1.61 (6H, br.s), 1.68 (3H, br.s.), 1.67 (3H, s), 1.96-2.01 (2H, m), 2.03-2.11 (4H, m), 2.12-2.17 (2H, m), 2.50 (2H, t, J=7.5 Hz), 3.61 (1H, t, J=7.5 Hz), 4.82 (1H, br.s), 4.88 (1H, br.s), 5.07-5.15 (2H, m) ppm.

$^{13}$C-NMR (125 MHz, $CDCl_3$): δ=16.02, 17.67, 25.67, 26.17, 26.65, 35.82, 39.16, 39.65, 42.80, 111.67, 123.54, 124.26, 131.32, 135.55, 145.55 ppm.

GC-MS (EI, 70 eV): 27, 41, 55, 69 (base peak), 81, 93, 109, 121, 136, 169, 197, 240 ($M^+$).

Example 17: Synthesis of (6E,9Z)-12-chloro-2,6,10-trimethyl-2,6,9-dodecatriene (When R=(E)-3,7-dimethyl-2,6-octadienyl Group, X=Cl, and Geometrical Isomerism of Double Bond of Position 9 is Z-Form in General Formula (B))

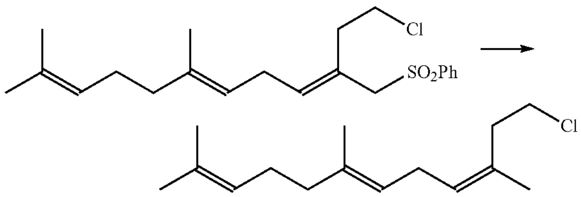

1.7 M Lithium triethylborohydride in tetrahydrofuran (8.00 ml) was poured for 5 minutes into a mixture of (3E,6E)-(1-chloro-7,11-dimethyl-3,6,10-dodecatrien-3-yl) methyl phenyl sulfone (2.75 g, 87.7% GC, 97.7% ZE) synthesized in the aforesaid Example 8, 1,3-bis(diphenylphosphino)propane palladium(II) chloride (0.210 g), and tetrahydrofuran (80 ml) in a nitrogen atmosphere under ice cooling with stirring. The reaction mixture was stirred for 50 minutes under ice cooling, then an aqueous solution (48.0 g) of 12.5% sodium hydroxide was added dropwise, and then 35% aqueous hydrogen peroxide (5.40 g) was added dropwise. Water was added to the reaction mixture, and the reaction mixture was extracted with diethyl ether. The diethyl ether solution was subjected to ordinary work-up, i.e., washing, drying, and concentration, and then purified by silica gel column chromatography to obtain the target compound, (6E,9Z)-(12-chloro-2,6,10-trimethyl-2,6,9-dodecatriene (1.53 g, 84.7 to 95.8% GC) (yield 86%).

(6E,9Z)-12-Chloro-2,6,10-trimethyl-2,6,9-dodecatriene

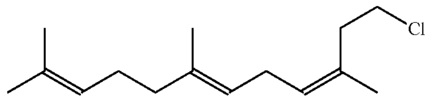 [SMILES: CC(C)=CCC/C(C)=C/C/C=C(/C)CCCl]

$C_{15}H_{25}Cl$

Colorless Oil

IR (D-ATR): ν=2967, 2915, 2856, 1650, 1445, 1378, 1318, 1297, 1242, 1152, 1134, 1108, 1023, 984, 934, 886, 833, 725, 659 $cm^{-1}$.

$^1$H-NMR (500 MHz, $CDCl_3$): δ=1.60 (3H, s), 1.63 (3H, q-like, J=~1 Hz), 1.68 (3H, q-like, J=~1.5 Hz), 1.72 (3H, q, J=1.3 Hz), 1.95-2.01 (2H, m), 2.03-2.11 (2H, m), 2.53 (2H, t, J=7.6 Hz), 2.71 (2H, t, J=7.3 Hz), 3.54 (2H, t, J=7.7 Hz), 5.05-5.12 (2H, m), 5.28 (1H, t-like, J=~7.4 Hz) ppm.

$^{13}$C-NMR (125 MHz, $CDCl_3$): δ=16.08, 17.68, 23.16, 25.68, 26.64, 26.90, 35.23, 39.65, 42.64, 122.53, 124.24, 127.34, 130.87, 131.41, 135.44 ppm.

GC-MS (EI, 70 eV): 41, 55, 69, 81, 93, 107, 123 (base peak), 135, 157, 171, 183, 197, 211, 225, 240 ($M^+$).

Example 18: Synthesis of (6Z,9E)-12-chloro-2,6,10-trimethyl-2,6,9-dodecatriene (When R=(Z)-3,7-dimethyl-2,6-octadienyl Group, X=Cl, and Geometrical Isomerism of Double Bond of Position 9 is E-Form in General Formula (B))

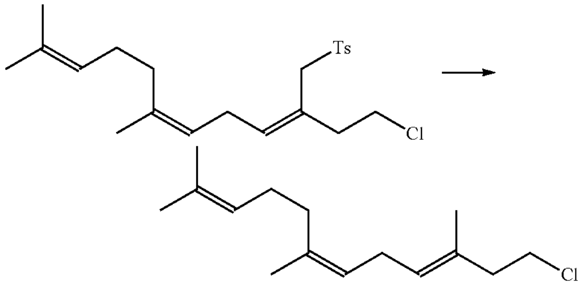

1.0 M Lithium triethylborohydride in tetrahydrofuran (27.4 ml) was poured for 5 minutes into a mixture of (3Z,6Z)-(1-chloro-7,11-dimethyl-3,6,10-dodecatrien-3-yl) methyl p-tolyl sulfone (6.0 g, 100% ZE) synthesized by a process similar to the aforesaid Example 9, 1,3-bis(diphenylphosphino)propane palladium(II) chloride (0.400 g), and tetrahydrofuran (160 ml) in a nitrogen atmosphere under ice cooling with stirring. The reaction mixture was stirred under ice cooling for 3 hours, then an aqueous solution (96 g) of 12.5% sodium hydroxide was added dropwise, and then 35% aqueous hydrogen peroxide (10.4 g) was added dropwise. Water was added to the reaction mixture, and an organic layer was fractionated. The organic layer was subjected to ordinary work-up, i.e., washing, drying, and concentration to obtain a crude product.

The crude product was a 80.7:19.3 mixture of target compound, (6Z,9E)-12-chloro-2,6,10-trimethyl-2,6,9-dodecatriene:Z-β-isomer, (Z)-12-chloro-2,6-dimethyl-10-methylene-2,6-dodecadiene, formed by a desulfonation reaction accompanying allylic rearrangement.

The crude product was separated by silica gel column chromatography to obtain the target compound, (6Z,9E)-12-chloro-2,6,10-trimethyl-2,6,9-dodecatriene, in amounts of 1.01 g (99.1% GC, target compound: Z-β-isomer=65.3:32.9 GC) and 2.50 g (97.8% GC, 84.7:13.1) (isomer total yield 82%). Thus, purity of isomers of the target compound may be improved by means for purification such as chromatography.

(6Z,9E)-12-Chloro-2,6,10-trimethyl-2,6,9-dodecatriene

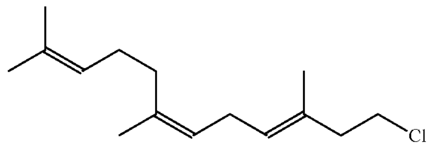 [SMILES: CC(C)=CCC/C(C)=C\C/C=C(\C)CCCl]

$C_{15}H_{25}Cl$
Colorless Oil

IR (D-ATR): ν=2965, 2916, 2856, 1648, 1449, 1376, 1324, 1294, 1246, 1151, 1108, 1087, 984, 888, 831, 727, 660 $cm^{-1}$.

$^{1}$H-NMR (500 MHz, $CDCl_3$): δ=1.61 (3H, q-like, J=~1 Hz), 1.65 (3H, q-like, J=~1 Hz), 1.68-1.70 (3H, m), 1.70 (3H, q, J=1.3 Hz), 2.02-2.10 (4H, m), 2.43 (2H, t, J=7.5 Hz), 2.71 (2H, t, J=7.3 Hz), 3.57 (2H, t, J=7.5 Hz), 5.07-5.15 (2H, m), 5.20 (1H, tq, J=7.1, 1.3 Hz) ppm.

$^{13}$C-NMR (125 MHz, $CDCl_3$): δ=15.77, 17.63, 23.37, 25.71, 26.54, 26.83, 31.97, 42.64, 43.17, 123.28, 124.21, 126.78, 130.87, 131.63, 135.63 ppm.

GC-MS (EI, 70 eV): 41, 55, 69, 81, 93, 107 (base peak), 121, 144, 158, 171, 183, 197, 211, 225, 240 ($M^+$).

Comparative Examples: Z-β-isomer, (Z)-12-chloro-2,6-dimethyl-10-methylene-2,6-dodecadiene, synthesized separately

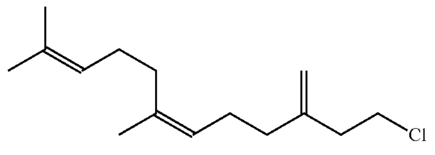 [SMILES: C=C(CCCl)CC/C=C(/C)CCC=C(C)C]

$C_{15}H_{25}Cl$
Colorless Oil

IR (D-ATR): ν=2964, 2927, 2856, 1646, 1449, 1376, 1325, 1242, 1152, 1109, 984, 895, 831, 738, 661 $cm^{-1}$.

$^{1}$H-NMR (500 MHz, $CDCl_3$): δ=1.62 (3H, br.s), 1.69 (6H, s-like), 1.97-2.10 (6H, m), 2.10-2.17 (2H, m), 2.49 (2H, t, J=7.5 Hz), 3.61 (2H, t, J=7.5 Hz), 4.82 (1H, br.s), 4.87 (1H, br.s), 5.09-5.15 (2H, m) ppm.

$^{13}$C-NMR (125 MHz, $CDCl_3$): δ=17.62, 23.34, 25.71, 26.08, 26.54, 31.98, 36.10, 39.19, 42.78, 111.63, 124.21, 124.33, 131.63, 135.74, 145.57 ppm.

GC-MS (EI, 70 eV): 27, 41, 53, 69 (base peak), 81, 93, 109, 129, 156, 169, 197, 240 ($M^+$).

Example 19: Synthesis of (6Z,9Z)-12-chloro-2,6,10-trimethyl-2,6,9-dodecatriene (When R=(Z)-3,7-dimethyl-2,6-octadienyl Group, X=Cl, and Geometrical Isomerism of Double Bond of Position 9 is Z-Form in General Formula (B))

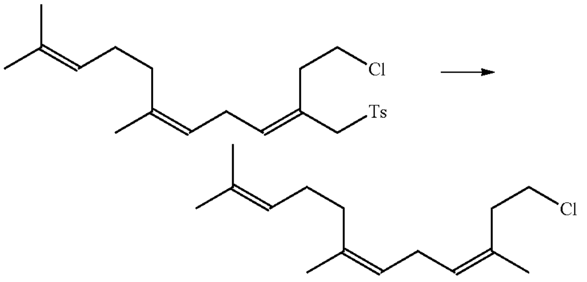

1.0 M Lithium triethylborohydride in tetrahydrofuran (4.00 ml) was poured for 5 minutes into a mixture of (3E,6Z)-(1-chloro-7,11-dimethyl-3,6,10-dodecatrien-3-yl) methyl p-tolyl sulfone (1.50 g, 86.4% GC, 92.5% EZ) synthesized by a process similar to the aforesaid Example 9, 1,3-bis(diphenylphosphino)propane palladium(II) chloride (0.10 g), and tetrahydrofuran (40 ml) in a nitrogen atmosphere under ice cooling with stirring. The reaction mixture was stirred under ice cooling for 70 minutes, then an aqueous solution (7.0 g) of 12.5% sodium hydroxide was added dropwise, and then 35% aqueous hydrogen peroxide (1.50 g) was added dropwise. Water was added to the reaction mixture, and the reaction mixture was extracted with n-hexane. The n-hexane solution was subjected to ordinary work-up, i.e., washing, drying, and concentration, and then purified by silica gel column chromatography to obtain the target compound, (6Z,9Z)-12-chloro-2,6,10-trimethyl-2,6,9-dodecatriene, in amounts of 0.140 g (97.6% GC) and 0.550 g (94.1% GC) (yield 83%).

(6Z,9Z)-12-Chloro-2,6,10-trimethyl-2,6,9-dodecatriene

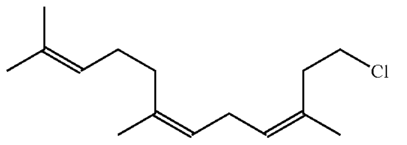 [SMILES: CC(C)=CCC/C(C)=C\C/C=C(/C)CCCl]

$C_{15}H_{25}Cl$
Colorless Oil

IR (D-ATR): ν=2966, 2928, 2856, 1660, 1446, 1377, 1318, 1297, 1241, 1145, 1108, 1084, 984, 934, 830, 725, 659 $cm^{-1}$.

$^{1}$H-NMR (500 MHz, $CDCl_3$): δ=1.62 (3H, q-like, J=~1 Hz), 1.68-1.72 (6H, m), 1.72 (3H, q, J=1.3 Hz), 2.03-2.09 (4H, m), 2.52 (2H, t, J=7.5 Hz), 2.71 (2H, t, J=7.3 Hz), 3.54 (2H, t, J=7.5 Hz), 5.08 (1H, tq-like, J=7.3, ~1.3 Hz), 5.10-5.16 (1H, m), 5.26 (1H, tq, J=7.3, ~0.8 Hz) ppm.

$^{13}$C-NMR (125 MHz, $CDCl_3$): δ=17.64, 23.15, 23.36, 25.71, 26.53, 26.76, 31.97, 35.20, 42.61, 123.31, 124.18, 127.48, 130.82, 131.67, 135.71 ppm.

GC-MS (EI, 70 eV): 41, 55, 69, 81, 93, 107 (base peak), 121, 144, 157, 171, 183, 197, 211, 225, 240 ($M^+$).

Example 20: Synthesis of (6E,9E)-12-bromo-2,6,10-trimethyl-2,6,9-dodecatriene (When R=(E)-3,7-dimethyl-2,6-octadienyl Group, X=Br, and Geometrical Isomerism of Double Bond of Position 9 is E-Form in General Formula (B))

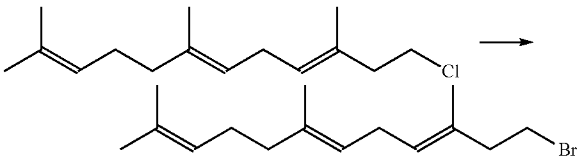

A mixture of (6E,9E)-12-chloro-2,6,10-trimethyl-2,6,9-dodecatriene (1.200 g, 81.7% EE-α) synthesized in the aforesaid Example 16, bromoethane (10.0 g), sodium bromide (0.250 g), and N-methyl-2-pyrrolidone (20 ml) was stirred in a nitrogen atmosphere for 15.5 hours at 60 to 75° C. The reaction mixture was cooled, and then water was added. The reaction mixture was extracted with n-hexane. The n-hexane solution was subjected to ordinary work-up, i.e., washing, drying, and concentration, and then purified by silica gel column chromatography to obtain the target compound, (6E,9E)-12-bromo-2,6,10-trimethyl-2,6,9-dodecatriene (1.30 g, 92.0% GC, 80.9% EE-α, yield 81%).

(6E,9E)-12-Bromo-2,6,10-trimethyl-2,6,9-dodecatriene

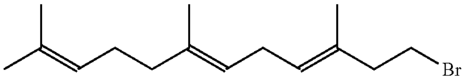 [SMILES: CC(C)=CCC/C(C)=C/C/C=C(\C)CCBr]

$C_{15}H_{25}Br$

Colorless Oil

IR (D-ATR): ν=2968, 2915, 2856, 1698, 1647, 1447, 1382, 1311, 1266, 1210, 1137, 1108, 1084, 984, 934, 888, 833, 656 $cm^{-1}$.

$^1H$-NMR (500 MHz, $CDCl_3$): δ=1.60 (3H, s-like), 1.62 (3H, q-like, J=~1.1 Hz), 1.65 (3H, q-like, J=1.1 Hz), 1.68 (3H, q-like, J=1.1 Hz), 1.95-2.02 (2H, m), 2.02-2.12 (2H, m), 2.53 (2H, t-like, J=~7.5 Hz), 2.71 (2H, t-like, J=~7 Hz), 3.43 (2H, t, J=7.5 Hz), 5.05-5.15 (2H, m), 5.21 (1H, tq, J=7.3, ~1.3 Hz) ppm.

$^{13}C$-NMR (125 MHz, $CDCl_3$): δ=15.63, 16.07, 17.68, 25.70, 26.65, 26.95, 31.67, 39.64, 42.90, 122.45, 124.24, 126.68, 131.38, 131.71, 135.47 ppm.

GC-MS (EI, 70 eV): 41, 55, 69, 81, 93, 107, 123 (base peak), 149, 173, 187, 201, 215, 241, 269, 284 ($M^+$).

Example 21: Synthesis of (6E,9Z)-12-bromo-2,6,10-trimethyl-2,6,9-dodecatriene (When R=(E)-3,7-dimethyl-2,6-octadienyl Group, X=Br, and Geometrical Isomerism of Double Bond of Position 9 is Z-Form in General Formula (B))

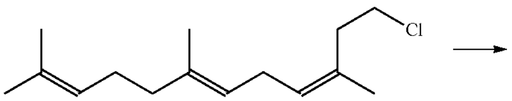

-continued

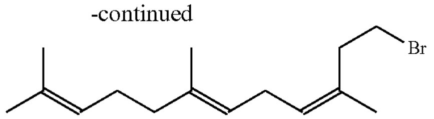

A mixture of (6E,9Z)-12-chloro-2,6,10-trimethyl-2,6,9-dodecatriene (1.60 g, 91.5% GC) synthesized in the aforesaid Example 17, bromoethane (8.00 g), sodium bromide (0.170 g), and N-methyl-2-pyrrolidone (30 ml) was stirred for 15 hours in a nitrogen atmosphere while heating under reflux at 80 to 95° C. The reaction mixture was cooled, and then water was added. The reaction mixture was extracted with n-hexane. The n-hexane solution was subjected to ordinary work-up, i.e., washing, drying, and concentration, and then purified by silica gel column chromatography to obtain the target compound, (6E,9Z)-12-bromo-2,6,10-trimethyl-2,6,9-dodecatriene (1.27 g, ~98.3% GC, 82.0% EZ, yield 73%).

(6E,9Z)-12-Bromo-2,6,10-trimethyl-2,6,9-dodecatriene

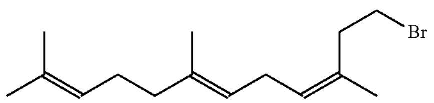 [SMILES: CC(C)=CCC/C(C)=C/C/C=C(/C)CCBr]

$C_{15}H_{25}Br$

Colorless Oil

IR (D-ATR): ν=2968, 2927, 2856, 1649, 1445, 1377, 1307, 1268, 1210, 1152, 1126, 1108, 1021, 984, 933, 887, 832, 652 $cm^{-1}$.

$^1H$-NMR (500 MHz, $CDCl_3$): δ=1.60 (3H, s-like), 1.63 (3H, q-like, J=~1 Hz), 1.67-1.74 (6H, m), 1.95-2.02 (2H, m), 2.03-2.11 (2H, m), 2.62 (2H, t, J=7.8 Hz), 2.71 (2H, t, J=7.3 Hz), 3.40 (2H, t, J=7.7 Hz), 5.05-5.14 (2H, m), 5.28 (1H, t-like, J=~7.4 Hz) ppm.

$^{13}C$-NMR (125 MHz, $CDCl_3$): δ=16.10, 17.68, 22.96, 25.69, 26.63, 26.90, 30.81, 35.50, 39.64, 122.46, 124.22, 127.24, 131.41, 131.72, 135.46 ppm.

GC-MS (EI, 70 eV): 41, 55, 69, 81, 93, 107, 123 (base peak), 135, 149, 157, 173, 187, 201, 215, 241, 255, 269, 284 ($M^+$).

Example 22: Synthesis of (6Z,9E)-12-bromo-2,6,10-trimethyl-2,6,9-dodecatriene (When R=(Z)-3,7-dimethyl-2,6-octadienyl Group, X=Br, and Geometrical Isomerism of Double Bond of Position 9 is E-Form in General Formula (B))

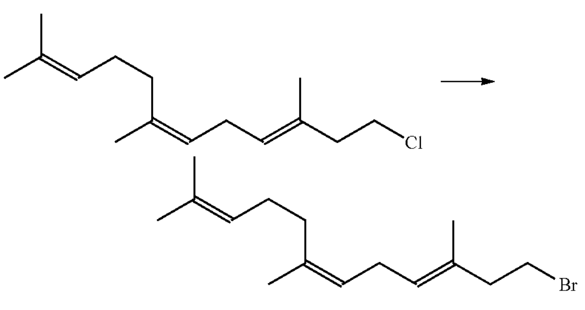

A mixture of (6Z,9E)-12-chloro-2,6,10-trimethyl-2,6,9-dodecatriene (1.00 g, 97.8% GC, 84.7% ZE) synthesized by a process similar to the aforesaid Example 18, bromoethane (5.00 g), sodium bromide (0.110 g), and N-methyl-2-pyrrolidone (20 ml) stirred for 18 hours in a nitrogen atmosphere while heating under reflux at 80° C. Bromoethane (5.00 g) was then added, and the reaction mixture was stirred for 4 hours. The reaction mixture was cooled, and then water was added. The reaction mixture was extracted with n-hexane. The n-hexane solution was subjected to ordinary work-up, i.e., washing, drying, and concentration, and then purified by silica gel column chromatography to obtain the target compound, (6Z,9E)-12-bromo-2,6,10-trimethyl-2,6,9-dodecatriene (1.27 g, ~98.3% GC, 82.0% ZE, yield 73%).

(6Z,9E)-12-Bromo-2,6,10-trimethyl-2,6,9-dodecatriene

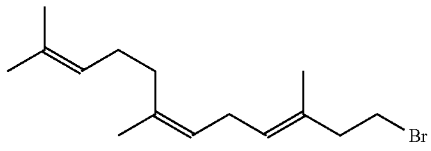 [SMILES: CC(C)=CCC/C(C)=C\C/C=C(\C)CCBr]

$C_{15}H_{25}Br$

Colorless Oil

IR (D-ATR): ν=2966, 2915, 2856, 1648, 1447, 1376, 1311, 1266, 1210, 1137, 1108, 1083, 984, 934, 888, 831, 656 $cm^{-1}$.

$^1$H-NMR (500 MHz, $CDCl_3$): δ=1.61 (3H, q-like, J=~1 Hz), 1.65 (3H, q-like, J=~1 Hz), 1.67-1.71 (6H, m), 1.98-2.14 (4H, m), 2.53 (2H, t-like, J=7.5 Hz), 2.71 (2H, t, J=7.2 Hz), 3.42 (2H, t, J=7.5 Hz), 5.07-5.15 (2H, m), 5.19 (1H, tq, J=7.1, 1.3 Hz) ppm.

$^{13}$C-NMR (125 MHz, $CDCl_3$): δ=15.63, 17.63, 23.37, 25.71, 26.54, 26.83, 31.60, 31.97, 42.91, 123.22, 124.20, 126.76, 131.63, 131.68, 135.66 ppm.

GC-MS (EI, 70 eV): 41, 55, 69, 81, 93, 107 (base peak), 121, 135, 149, 163, 177, 201, 215, 241, 255, 269, 284 ($M^+$).

Example 23: Synthesis of (6Z,9Z)-12-bromo-2,6,10-trimethyl-2,6,9-dodecatriene (When R=(Z)-3,7-dimethyl-2,6-octadienyl Group, X=Br, and Geometrical Isomerism of Double Bond of Position 9 is Z-Form in General Formula (B))

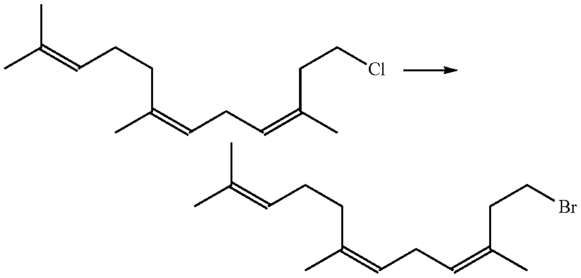

A mixture of (6Z,9Z)-12-chloro-2,6,10-trimethyl-2,6,9-dodecatriene (2.40 g, 99.1% GC, 94.6% ZZ) synthesized by a process similar to the aforesaid Example 19, bromoethane (10.0 g), sodium bromide (0.300 g), and N-methyl-2-pyrrolidone (40 ml) was stirred for 10 hours in a nitrogen atmosphere while heating under reflux at 70° C. Bromoethane (5.00 g) was then added, and the reaction mixture was stirred for 12 hours. The reaction mixture was cooled, and then water was added. The reaction mixture was extracted with n-hexane. The n-hexane solution was subjected to ordinary work-up, i.e., washing, drying, and concentration, and then purified by silica gel column chromatography to obtain the target compound, (6Z,9Z)-12-bromo-2,6,10-trimethyl-2,6,9-dodecatriene (2.66 g, 81.0 to 88.3% GC, ~88.1% ZZ, yield 85%).

(6Z,9Z)-12-Bromo-2,6,10-trimethyl-2,6,9-dodecatriene

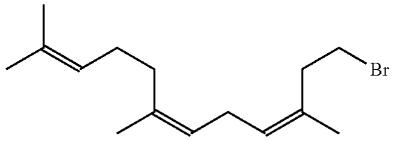 [SMILES: CC(C)=CCC/C(C)=C\C/C=C(/C)CCBr]

$C_{15}H_{25}Br$

Colorless Oil

IR (D-ATR): ν=2967, 2927, 2856, 1672, 1446, 1377, 1308, 1268, 1210, 1124, 1108, 1022, 985, 934, 830, 652 $cm^{-1}$.

$^1$H-NMR (500 MHz, $CDCl_3$): δ=1.62 (3H, q-like, J=~1 Hz), 1.68-1.71 (6H, m), 1.72 (3H, q, J=1.3 Hz), 2.05-2.10 (4H, m), 2.62 (2H, t, J=7.8 Hz), 2.70 (2H, t, J=7.3 Hz), 3.40 (2H, t, J=7.8 Hz), 5.05-5.17 (2H, m), 5.26 (1H, tq-like, J=7.3, ~0.6 Hz) ppm.

$^{13}$C-NMR (125 MHz, $CDCl_3$): δ=17.65, 22.95, 23.36, 25.72, 26.52, 26.76, 30.77, 31.97, 35.46, 123.25, 124.16, 127.38, 131.65, 131.68, 135.73 ppm.

GC-MS (EI, 70 eV): 41, 55, 69, 81, 93, 107 (base peak), 121, 135, 149, 163, 177, 201, 215, 241, 255, 269, 284 ($M^+$).

Example 24: Synthesis of (6E,9E)-12-iodo-2,6,10-trimethyl-2,6,9-dodecatriene (When R=(E)-3,7-dimethyl-2,6-octadienyl Group, X=I, and Geometrical Isomerism of Double Bond of Position 9 is E-Form in General Formula (B))

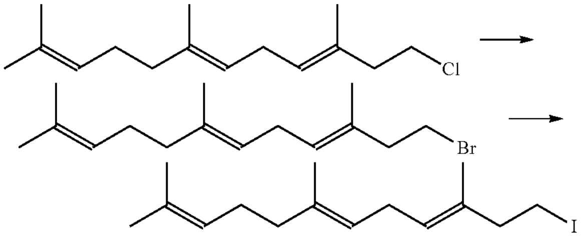

A mixture of (6E,9E)-12-chloro-2,6,10-trimethyl-2,6,9-dodecatriene (40 mg, 97.3% GC, 87.8% EE) synthesized in the aforesaid Example 16, bromoethane (2.00 g), sodium iodide (50 mg), acetone (10 g), and N-methyl-2-pyrrolidone (4.0 g) was stirred for 19 hours in a nitrogen atmosphere while heating under reflux at 70 to 85° C. The reaction mixture was cooled, and then water was added. The reaction mixture was extracted with n-hexane. The n-hexane solution was subjected to ordinary work-up, i.e., washing, drying, and concentration, and then purified by silica gel column chromatography to obtain the target compound, (6E,9E)-12-iodo-2,6,10-trimethyl-2,6,9-dodecatriene (39 mg, 92.4 to 97.2% GC, 47.4 to 89.0% EE, yield 71%).

(6E,9E)-12-Iodo-2,6,10-trimethyl-2,6,9-dodecatriene

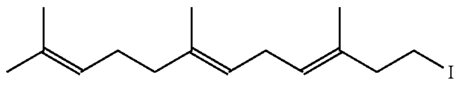 [SMILES: CC(C)=CCC/C(C)=C/C/C=C(\C)CCI]

$C_{15}H_{25}I$

Colorless Oil

IR (D-ATR): ν=2966, 2923, 2854, 1647, 1444, 1382, 1328, 1304, 1243, 1169, 1131, 1108, 984, 935, 888, 833, 622 $cm^{-1}$.

$^{1}$H-NMR (500 MHz, $CDCl_3$): δ=1.60 (3H, s-like), 1.62 (3H, q, J=1.2 Hz), 1.64 (3H, q, J=1.2 Hz), 1.68 (3H, q, J=1.2 Hz), 1.95-2.01 (2H, m), 2.02-2.11 (2H, m), 2.53 (2H, t-like, J=~8 Hz), 2.69 (2H, t-like, J=~7 Hz), 3.22 (2H, t, J=7.8 Hz), 5.04-5.14 (2H, m), 5.19 (1H, tq-like, J=~7, ~1.3 Hz) ppm.

$^{13}$C-NMR (125 MHz, $CDCl_3$): δ=5.01, 15.37, 16.10, 17.70, 25.71, 26.68, 26.96, 39.65, 43.84, 122.44, 124.27, 126.35, 131.39, 133.39, 135.47 ppm.

GC-MS (EI, 70 eV): 41, 55, 69, 81, 91, 107, 123 (base peak), 139, 155, 177, 195, 221, 263, 289.

Example 25: Synthesis of (6Z,9Z)-12-iodo-2,6,10-trimethyl-2,6,9-dodecatriene (When R=(Z)-3,7-dimethyl-2,6-octadienyl Group, X=I, and Geometrical Isomerism of Double Bond of Position 9 is Z-Form in General Formula (B))

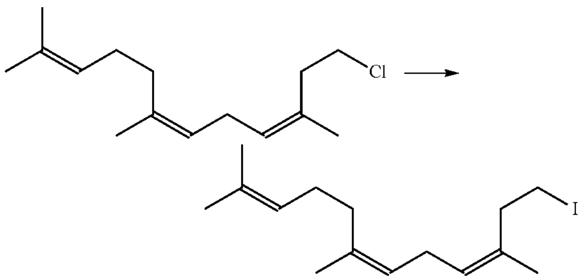

A mixture of (6Z,9Z)-12-chloro-2,6,10-trimethyl-2,6,9-dodecatriene (100 mg, 89.5% GC) synthesized by a process similar to the aforesaid Example 19, sodium iodide (450 mg), and acetone (10 ml) was stirred for 7 hours in a nitrogen atmosphere while heating under reflux at 60 to 65° C., and then 2-butanone (10 ml) was added. The reaction mixture was stirred for 3 hours at 80 to 85° C. The reaction mixture was cooled, and then concentrated at a reduced pressure. The residue was a 68.6:31.4 mixture of starting material, (6Z,9Z)-12-chloro-2,6,10-trimethyl-2,6,9-dodecatriene:target compound, (6Z,9Z)-12-iodo-2,6,10-trimethyl-2,6,9-dodecatriene. This crude product was used as such as a starting material in a subsequent step.

(6Z,9Z)-12-Iodo-2,6,10-trimethyl-2,6,9-dodecatriene

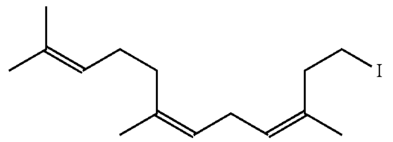 [SMILES: CC(C)=CCC/C(C)=C\C/C=C(/C)CCI]

$C_{15}H_{25}I$

GC-MS (EI, 70 eV): 41, 55, 69 (base peak), 91, 107, 123, 149, 177, 195, 219, 236, 262, 289, 332 ($M^+$).

Example 26: Synthesis of (E)-8-chloro-2,6-dimethyl-2,5-octadienene (When R=3-methyl-2-butenyl Group, X=Cl, and Geometrical Isomerism of Double Bond of Position 5 is E-Form in General Formula (B))

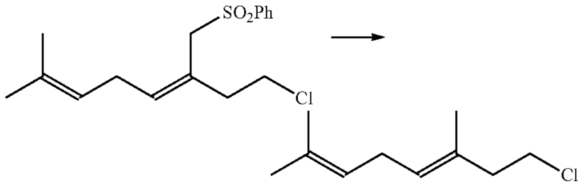

1.0 M Lithium triethylborohydride in tetrahydrofuran (60 ml) was added dropwise to a mixture of (Z)-(1-chloro-7-methyl-3,6-octadienen-3-yl)methyl phenyl sulfone (10.2 g, ~80% GC, 95.7% Z) synthesized in the aforesaid Example 12, 1,3-bis(diphenylphosphino)propane palladium(II) chloride (0.96 g), and tetrahydrofuran (300 ml) in a nitrogen atmosphere for 15 minutes under ice cooling with stirring. The reaction mixture was stirred under ice cooling for 65 minutes, then an aqueous solution (100 g) of 12.5% sodium hydroxide was added dropwise, and then 35% aqueous hydrogen peroxide (26.0 g) was added dropwise. Water was added to the reaction mixture, and the reaction mixture was extracted with n-hexane. The n-hexane solution was subjected to ordinary work-up, i.e., washing, drying, and concentration, and then purified by silica gel column chromatography to obtain the target compound, (E)-8-chloro-2,6-dimethyl-2,5-octadienene (4.19 g, 78.3 to 100% GC, yield 77%).

(E)-8-Chloro-2,6-dimethyl-2,5-octadienene

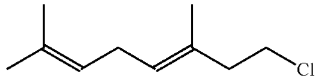

$C_{10}H_{17}Cl$

Colorless Oil

IR (D-ATR): ν=2969, 2915, 2857, 1450, 1376, 1324, 1294, 1247, 1150, 1105, 984, 933, 831, 726, 660 $cm^{-1}$.

$^{1}$H-NMR (500 MHz, $CDCl_3$): δ=1.63 (3H, s-like), 1.65 (3H, s-like), 1.69 (3H, q-like, J=~1 Hz), 2.44 (2H, t-like, J=~7.5 Hz), 2.70 (2H, t, J=7.1 Hz), 3.57 (2H, t, J=7.3 Hz), 5.06-5.11 (1H, m), 5.19-5.23 (1H, m) ppm.

$^{13}$C-NMR (125 MHz, $CDCl_3$): δ=15.76, 17.71, 25.66, 27.07, 42.63, 43.18, 122.66, 126.62, 130.91, 131.83 ppm.

GC-MS (EI, 70 eV): 41, 53, 67, 81, 93, 109 (base peak), 121, 137, 157, 172 ($M^+$).

Example 27: Synthesis of (Z)-8-chloro-2,6-dimethyl-2,5-octadienene (When R=3-methyl-2-butenyl Group, X═Cl, and Geometrical Isomerism of Double Bond of Position 5 is Z-Form in General Formula (B))

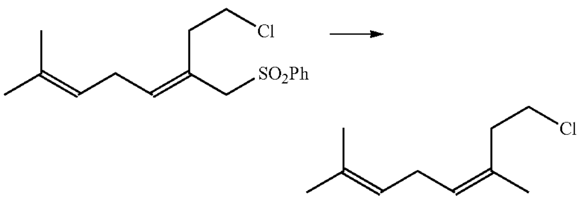

1.0 M Lithium triethylborohydridein tetrahydrofuran (22 ml) was added dropwise to a mixture of (E)-(1-chloro-7-methyl-3,6-octadienen-3-yl)methyl phenyl sulfone (3.75 g, ~80% GC, 100% E) synthesized in the aforesaid Example 12, 1,3-bis(diphenylphosphino)propane palladium(II) chloride (0.35 g), and tetrahydrofuran (120 ml) in a nitrogen atmosphere for 10 minutes under ice cooling with stirring. The reaction mixture was stirred under ice cooling for 2 hours, then an aqueous solution (80 g) of 12.5% sodium hydroxide was added dropwise, and then 35% aqueous hydrogen peroxide (9.50 g) was added dropwise. Water was added to the reaction mixture, and the reaction mixture was extracted with n-hexane. The n-hexane solution was subjected to ordinary work-up, i.e., washing, drying, and concentration, and then purified by silica gel column chromatography to obtain the target compound, (Z)-8-chloro-2,6-dimethyl-2,5-octadienene (1.58 g, 93.3 to 97.2% GC, 82.0 to 58.3% Z, yield 76%).

(Z)-8-Chloro-2,6-dimethyl-2,5-octadienene

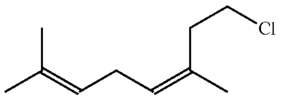

$C_{10}H_{17}Cl$

Colorless Oil

IR (D-ATR): ν=2968, 2928, 2914, 2877, 1445, 1377, 1318, 1297, 1242, 1103, 825, 725, 659 $cm^{-1}$.

$^{1}$H-NMR (500 MHz, $CDCl_3$): δ=1.64 (3H, s-like), 1.69 (3H, q-like, J=~1.1 Hz), 1.72 (3H, q-like, J=~1.3 Hz), 2.53 (2H, t, J=7.5 Hz), 2.70 (2H, t, J=7.3 Hz), 3.54 (2H, t, J=7.5 Hz), 5.05-5.10 (1H, m), 5.25-5.31 (1H, t-like, J=~7 Hz) ppm.

$^{13}$C-NMR (125 MHz, $CDCl_3$): δ=17.71, 23.14, 25.67, 27.02, 35.22, 42.62, 122.69, 126.63, 130.87, 131.83 ppm.

GC-MS (EI, 70 eV): 41, 53, 67, 81, 93, 109 (base peak), 121, 157, 172 ($M^+$).

Example 28: Synthesis of (E)-8-bromo-2,6-dimethyl-2,5-octadienene (When R=3-methyl-2-butenyl Group, X═Br, and Geometrical Isomerism of Double Bond of Position 5 is E-Form in General Formula (B))

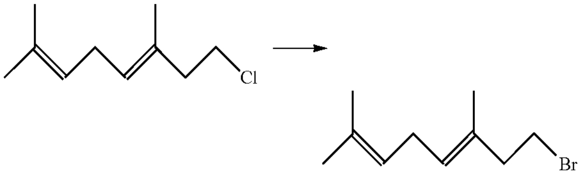

A mixture of (E)-8-chloro-2,6-dimethyl-2,5-octadienene (2.70 g, 84.6% GC) synthesized in the aforesaid Example 26, bromoethane (5.0 g), sodium bromide (0.200 g), and N-methyl-2-pyrrolidone (10 ml) was stirred in a nitrogen atmosphere for 11 hours while heating under reflux at 60 to 70° C. The reaction mixture was cooled, and then water was added. The reaction mixture was extracted with n-hexane. The n-hexane solution was subjected to ordinary work-up, i.e., washing, drying, and concentration to obtain the target compound, (E)-8-bromo-2,6-dimethyl-2,5-octadienene (2.66 g, 80.7% GC, yield 81%). This crude product had sufficient purity, and was used as such as a starting material in a subsequent step.

(E)-8-Bromo-2,6-dimethyl-2,5-octadienene

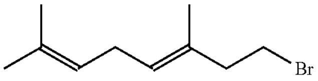

$C_{10}H_{17}Br$

Colorless Oil

IR (D-ATR): ν=2969, 2914, 2857, 1697, 1447, 1376, 1311, 1266, 1211, 1137, 1104, 984, 933, 893, 831, 759, 655 $cm^{-1}$.

$^{1}$H-NMR (500 MHz, $CDCl_3$): δ=1.63 (3H, s-like), 1.65 (3H, q-like, J=1.2 Hz), 1.69 (3H, q-like, J=~1.3 Hz), 2.53 (2H, t, J=7.7 Hz), 2.70 (2H, t, J=7.2 Hz), 3.43 (2H, t, J=7.6 Hz), 5.06-5.13 (1H, m), 5.18-5.24 (1H, m) ppm.

$^{13}$C-NMR (125 MHz, $CDCl_3$): δ=15.62, 17.71, 25.66, 27.06, 31.62, 42.89, 122.60, 126.60, 131.72, 131.85 ppm.

GC-MS (EI, 70 eV): 41, 53, 67, 81, 93, 109 (base peak), 121, 137, 203, 216 ($M^+$).

Example 29: Synthesis of (Z)-8-bromo-2,6-dimethyl-2,5-octadienene (When R=3-methyl-2-butenyl Group, X═Cl, and Geometrical Isomerism of Double Bond of Position 5 is Z-Form in General Formula (B))

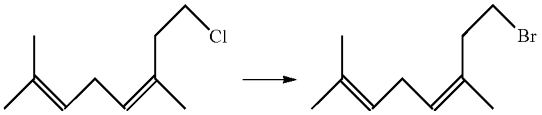

A mixture of (Z)-8-chloro-2,6-dimethyl-2,5-octadienene (1.47 g, 93.3% GC, 82.0% Z) synthesized in the aforesaid Example 27, bromoethane (10.2 g), sodium bromide (0.220 g), and N-methyl-2-pyrrolidone (10 ml) was stirred in a nitrogen atmosphere for 9 hours while heating under vigorous reflux at 80 to 90° C. The reaction mixture was cooled, and then water was added. The reaction mixture was extracted with n-hexane. The n-hexane solution was subjected to ordinary work-up, i.e., washing, drying, and concentration, and then purified by silica gel column chromatography to obtain the target compound, (Z)-8-bromo-2,6-dimethyl-2,5-octadienene (1.49 g, 91.1 to 94.4% GC, 51.8 to 73.0% Z, yield 76%).

(Z)-8-Bromo-2,6-dimethyl-2,5-octadienene

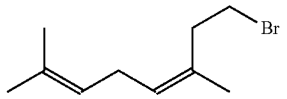

$C_{10}H_{17}Br$

Colorless Oil

IR (D-ATR): ν=2969, 2928, 2914, 2857, 1445, 1377, 1308, 1268, 1210, 1127, 1102, 889, 825, 652 $cm^{-1}$.

$^1$H-NMR (500 MHz, $CDCl_3$): δ=1.64 (3H, s-like), 1.69 (3H, q-like, J=~1.1 Hz), 1.72 (3H, q-like, J=~1.2 Hz), 2.63 (2H, t, J=7.6 Hz), 2.70 (2H, t, J=7.1 Hz), 3.40 (2H, t, J=7.6 Hz), 5.05-5.12 (1H, m), 5.28 (1H, t-like, J=~7.5 Hz) ppm.

$^{13}$C-NMR (125 MHz, $CDCl_3$): δ=17.73, 22.94, 25.67, 27.02, 30.79, 35.48, 122.62, 127.19, 131.72, 131.86 ppm.

GC-MS (EI, 70 eV): 41, 53, 67, 81, 93, 109 (base peak), 121, 137, 203, 216 ($M^+$).

Example 30: Synthesis of (1E,4E)-7-chloro-5-methyl-1-phenyl-1,4-heptadiene (When R=(E)-cinnamyl Group, X=Cl, and Geometrical Isomerism of Double Bond of Position 4 is E-Form in General Formula (B))

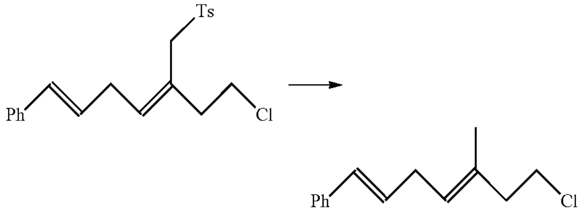

1.7 M Lithium triethylborohydridein tetrahydrofuran (8.50 ml) was poured into a mixture of (3Z,6E)-(1-chloro-7-phenyl-3,6-heptadien-3-yl)methyl p-tolyl sulfone (3.00 g, 95.6% Z) synthesized in the aforesaid Example 14, 1,3-bis (diphenylphosphino)propane palladium(II) chloride (0.24 g), and tetrahydrofuran (85 ml) in a nitrogen atmosphere for 5 minutes under ice cooling with stirring. The reaction mixture was stirred under ice cooling for 2 hours, then an aqueous solution (50 g) of 12.5% sodium hydroxide was added dropwise, and then 35% aqueous hydrogen peroxide (5.80 g) was added dropwise. Water was added to the reaction mixture, and the reaction mixture was extracted with n-hexane. The n-hexane solution was subjected to ordinary work-up, i.e., washing, drying, and concentration, and then purified by silica gel column chromatography to obtain the target compound, (1E,4E)-7-chloro-5-methyl-1-phenyl-1,4-heptadiene (1.59 g, 93.5 to 97.8% GC, 75.2 to 80.3% EE, yield 92%).

(1E,4E)-7-Chloro-5-methyl-1-phenyl-1,4-heptadiene

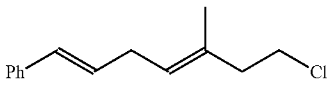

$C_{14}H_{17}Cl$

Colorless Oil

IR (D-ATR): ν=3081, 3058, 3025, 2961, 2914, 1947, 1874, 1800, 1648, 1599, 1577, 1494, 1447, 1385, 1324, 1293, 1246, 1207, 1150, 1129, 964, 910, 838, 742, 692, 657 $cm^{-1}$.

$^1$H-NMR (500 MHz, $CDCl_3$): δ=1.69 (3H, s-like), 2.50 (2H, t, J=7.3 Hz), 2.94 (2H, t-like, J=~7 Hz), 3.62 (2H, t, J=7.3 Hz), 5.36 (1H, tq, J=7.3, 1.3 Hz), 6.19 (1H, dt, J=15.9, 6.4 Hz), 6.41 (1H, dt, J=15.9, 1.6 Hz), 7.18-7.22 (1H, m), 7.26-7.32 (2H, m), 7.32-7.37 (2H, m) ppm.

$^{13}$C-NMR (125 MHz, $CDCl_3$): δ=15.74, 31.39, 42.55, 43.07, 124.79, 125.96, 126.90, 128.45, 128.64, 129.93, 132.68, 137.67 ppm.

GC-MS (EI, 70 eV): 39, 51, 65, 77, 91, 103, 115, 129 (base peak), 142, 157, 169, 184, 205, 220 ($M^+$).

Example 31: Synthesis of (1E,4E)-7-bromo-5-methyl-1-phenyl-1,4-heptadiene (When R=(E)-cinnamyl Group, X=Br, and Geometrical Isomerism of Double Bond of Position 4 is E-Form in General Formula (B))

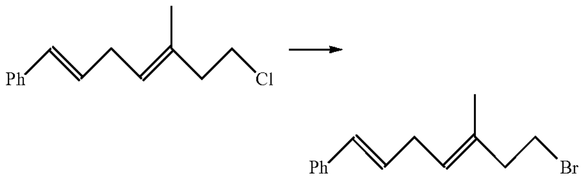

A mixture of (1E,4E)-7-chloro-5-methyl-1-phenyl-1,4-heptadiene (200 mg, 75.2% GC) synthesized in the aforesaid Example 30, sodium bromide (170 mg), and N-methyl-2-pyrrolidone (6 ml) was stirred in a nitrogen atmosphere for 9 hours while heating at 40 to 50° C. The reaction mixture was used as such in a subsequent step.

(1E,4E)-7-Bromo-5-methyl-1-phenyl-1,4-heptadiene

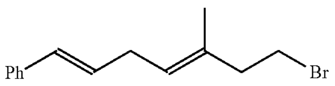

$C_{14}H_{17}Br$

GC-MS (EI, 70 eV): 39, 53, 77, 91, 115, 129, 143, 157 (base peak), 171, 185, 207, 221, 235, 249, 264 ($M^+$).

Example 32: Synthesis of (E)-1-chloro-3-methyl-3-dodecene (When R=n-octyl Group, X=Cl, and Geometrical Isomerism of Double Bond of Position 3 is E-Form in General Formula (B))

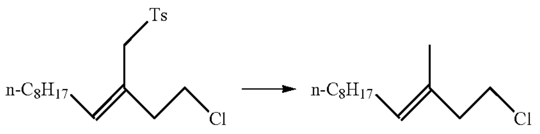

1.7 M Lithium triethylborohydride in tetrahydrofuran (3.62 ml) was poured into a mixture of (Z)-(1-chloro-3-dodecen-3-yl)methyl p-tolyl sulfone (1.27 g, ~100% Z) synthesized in the aforesaid Example 15, 1,3-bis(diphenylphosphino)propane palladium(II) chloride (100 mg), and tetrahydrofuran (40 ml) in a nitrogen atmosphere for 2 minutes under ice cooling with stirring. The reaction mixture was stirred under ice cooling for 30 minutes, then an aqueous solution (21.0 g) of 12.5% sodium hydroxide was added dropwise, and then 35% aqueous hydrogen peroxide (2.44 g) was added dropwise. Water was added to the reaction mixture, and the reaction mixture was extracted with diethyl ether. The diethyl ether solution was subjected to ordinary work-up, i.e., washing, drying, and concentration, and then purified by silica gel column chromatography to obtain the target compound, (E)-1-chloro-3-methyl-3-dodecene (630 mg, 92.8% GC, yield 78%).

(E)-1-Chloro-3-methyl-3-dodecene

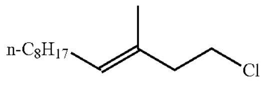

$C_{13}H_{25}Cl$

Colorless Oil

IR (D-ATR): ν=2957, 2925, 2854, 1455, 1379, 1324, 1245, 1150, 919, 725, 661 $cm^{-1}$.

$^1$H-NMR (500 MHz, $CDCl_3$): δ=0.88 (3H, t, J=7.0 Hz), 1.22-1.37 (12H, m), 1.62 (3H, s-like), 1.99 (2H, q-like, J=~7 Hz), 2.43 (2H, t, J=7.4 Hz), 3.57 (2H, t, J=7.4 Hz), 5.23 (1H, tq, J=7.2, 1.3 Hz) ppm.

$^{13}$C-NMR (125 MHz, $CDCl_3$): δ=14.10, 15.70, 22.67, 27.94, 29.27, 29.30, 29.50, 29.60, 31.88, 42.70, 43.29, 128.28, 130.75 ppm.

GC-MS (EI, 70 eV): 41, 55, 69 (base peak), 81, 97, 117, 132, 153, 165, 188, 216 ($M^+$).

Example 33: Synthesis of (Z)-1-chloro-3-methyl-3-dodecene (When R=n-octyl Group, X=Cl, and Geometrical Isomerism of Double Bond of Position 3 is Z-Form in General Formula (B))

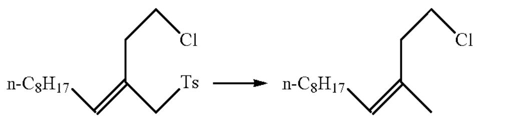

1.7 M Lithium triethylborohydride in tetrahydrofuran (3.70 ml) was poured into a mixture of (E)-(1-chloro-3-dodecen-3-yl)methyl p-tolyl sulfone (1.28 g, ~100% E) synthesized in the aforesaid Example 15, 1,3-bis(diphenylphosphino)propane palladium(II) chloride (100 mg), and tetrahydrofuran (40 ml) in a nitrogen atmosphere for 5 minutes under ice cooling with stirring. The reaction mixture was stirred under ice cooling for 85 minutes, then an aqueous solution (23.1 g) of 12.5% sodium hydroxide was added dropwise, and then 35% aqueous hydrogen peroxide (2.70 g) was added dropwise. Water was added to the reaction mixture, and the reaction mixture was extracted with n-hexane. The n-hexane solution was subjected to ordinary work-up, i.e., washing, drying, and concentration, and then purified by silica gel column chromatography to obtain the target compound, (Z)-1-chloro-3-methyl-3-dodecene (660 mg, 99.6% GC, 100% E, yield 88%).

(Z)-1-Chloro-3-methyl-3-dodecene

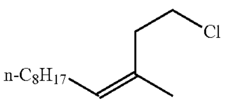

$C_{13}H_{25}Cl$

Colorless Oil

IR (D-ATR): ν=2958, 2925, 2854, 1457, 1378, 1296, 1241, 1079, 833, 723, 660 $cm^{-1}$.

$^1$H-NMR (500 MHz, $CDCl_3$): δ=0.88 (3H, t, J=7.0 Hz), 1.22-1.37 (12H, m), 1.71 (3H, q, J=1.3 Hz), 1.99 (2H, q-like, J=~7 Hz), 2.50 (2H, t, J=7.5 Hz), 3.53 (2H, t, J=7.5 Hz), 5.29 (1H, tq, J=7.3, 0.6 Hz) ppm.

$^{13}$C-NMR (125 MHz, $CDCl_3$): δ=14.11, 22.67, 23.16, 27.94, 29.29, 29.36, 29.52, 29.88, 31.88, 35.20, 42.72, 128.97, 130.61 ppm.

GC-MS (EI, 70 eV): 41, 55, 69 (base peak), 81, 97, 117, 132, 153, 165, 188, 216 ($M^+$).

Example 34: Synthesis of (E)-8-chloro-2,6-dimethyl-1,5-octadienene (When R=3-methyl-3-butenyl Group, X=Cl, and Geometrical Isomerism of Double Bond of Position 3 is E-Form in General Formula (B))

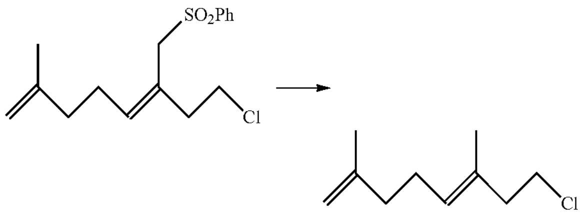

1.0 M Lithium triethylborohydride in tetrahydrofuran (9.50 ml) was poured into a mixture of (Z)-(8-chloro-2-methyl-1,5-octadienen-6-yl)methyl phenyl sulfone (1.65 g, >96.4% Z) synthesized in the aforesaid Example 13, 1,3-bis(diphenylphosphino)propane palladium(II) chloride (0.155 g), and tetrahydrofuran (50 ml) in a nitrogen atmosphere for 5 minutes under ice cooling with stirring. The reaction mixture was stirred under ice cooling for 2 hours, then an aqueous solution (16.0 g) of 12.5% sodium hydroxide was added dropwise, and then 35% aqueous hydrogen peroxide (4.20 g) was added dropwise. Water was added to the reaction mixture, and the reaction mixture was extracted with n-hexane. The n-hexane solution was subjected to ordinary work-up, i.e., washing, drying, and concentration, and then purified by silica gel column chromatography to obtain the target compound, (E)-8-chloro-2,6-dimethyl-1,5-octadienene (0.830 g, 84.9 to 91.5% GC, yield 97%).

(E)-8-Chloro-2,6-dimethyl-1,5-octadienene

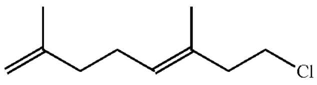

$C_{10}H_{17}Cl$
Colorless Oil

IR (D-ATR): ν=3074, 2966, 2935, 2857, 1650, 1451, 1385, 1374, 1325, 1294, 1247, 1150, 1092, 888, 726, 660 $cm^{-1}$.

$^1$H-NMR (500 MHz, $CDCl_3$): δ=1.64 (3H, s-like), 1.72 (3H, s-like), 2.01-2.07 (2H, m), 2.12-2.19 (2H, m), 2.44 (2H, t-like, J=~7 Hz), 3.56 (2H, t, J=7.3 Hz), 4.68 (1H, br.s-like), 4.71 (1H, br.s-like), 5.23 (1H, tq, J=6.9, 1.3 Hz) ppm.

$^{13}$C-NMR (125 MHz, $CDCl_3$): δ=15.74, 22.45, 26.16, 37.51, 42.61, 43.22, 109.96, 127.42, 131.21, 145.54 ppm.

GC-MS (EI, 70 eV): 27, 39, 55, 67, 81 (base peak), 91, 105, 117, 130, 144, 157, 172 ($M^+$).

Example 35: Synthesis of (E)-8-bromo-2,6-dimethyl-1,5-octadienene (When R=3-methyl-3-butenyl Group, X=Br, and Geometrical Isomerism of Double Bond of Position 3 is E-Form in General Formula (B))

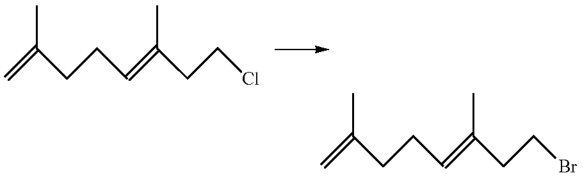

A mixture of (E)-8-chloro-2,6-dimethyl-1,5-octadienene (0.700 g, 91.5% GC) synthesized in the aforesaid Example 34, bromoethane (3.53 g), sodium bromide (0.150 g), and N-methyl-2-pyrrolidone (10 ml) was stirred in a nitrogen atmosphere for 3 hours while heating under vigorous reflux at 75 to 80° C. The reaction mixture was cooled, and then water was added. The reaction mixture was extracted with n-hexane. The n-hexane solution was subjected to ordinary work-up, i.e., washing, drying, and concentration to obtain the target compound, crude (E)-8-bromo-2,6-dimethyl-1,5-octadienene (0.830 g, 68.5% GC, yield 71%). The isomer ratio of this crude product in $^1$H-NMR was as follows: target compound, (E)-8-bromo-2,6-dimethyl-1,5-octadienene:isomer (E)-8-bromo-2,6-dimethyl 2,5-octadienene having double bond of position 1 rearranged to position 2:isomer 8-bromo-2-methyl-6-methylen-1-octene having double bond of position 5 rearranged to exo=75.4:18.5:6.1.

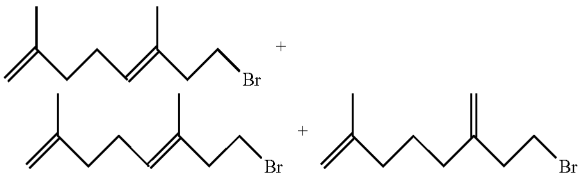

(E)-8-Bromo-2,6-dimethyl-1,5-octadienene

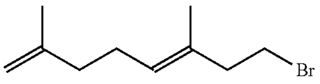

$C_{10}H_{17}Br$
Colorless Oil

IR (D-ATR): ν=3074, 2968, 2932, 2857, 1697, 1649, 1500, 1447, 1402, 1385, 1375, 1311, 1296, 1267, 1209, 1137, 888, 655 $cm^{-1}$.

$^1$H-NMR (500 MHz, $CDCl_3$): δ=1.63 (3H, s-like), 1.72 (3H, s-like), 2.01-2.07 (2H, m), 2.12-2.18 (2H, m), 2.53 (2H, t-like, J=~7.5 Hz), 3.42 (2H, t, J=7.5 Hz), 4.67 (1H, br.s-like), 4.71 (1H, br.s-like), 5.23 (1H, tq, J=6.9, 1.3 Hz) ppm.

$^{13}$C-NMR (125 MHz, $CDCl_3$): δ=15.60, 22.45, 26.16, 31.70, 37.48, 42.87, 109.98, 127.41, 132.01, 145.52 ppm.

GC-MS (EI, 70 eV), 27, 41, 55, 67, 81 (base peak), 95, 109, 121, 137, 149, 161, 174, 190, 203, 216 ($M^+$).

(E)-8-Bromo-2,6-dimethyl 2,5-octadienene

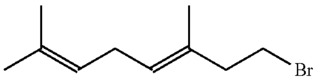

$C_{10}H_{17}Br$

GC-MS (EI, 70 eV), 27, 41, 53, 67, 81, 93, 109 (base peak), 121, 137, 149, 161, 175, 187, 201, 216 ($M^+$).

8-Bromo-2-methyl-6-methylen-1-octene

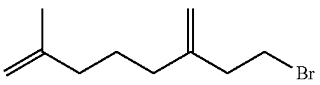

$C_{10}H_{17}Br$

GC-MS (EI, 70 eV), 27, 41, 53, 67, 81 (base peak), 95, 109, 121, 137, 160, 173, 188, 201.

Examples: Synthesis of 4-Substituted 3-Methyl-1,3-Butadiene Compound of the Following General Formula (A)

(A)

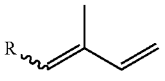

Example 36: Synthesis (1) of (3E,6E)-α-farnesene (When R=(E)-3,7-dimethyl-2,6-octadienyl Group, and Geometrical Isomerism of Double Bond of Position 3 is E-Form in General Formula (A))

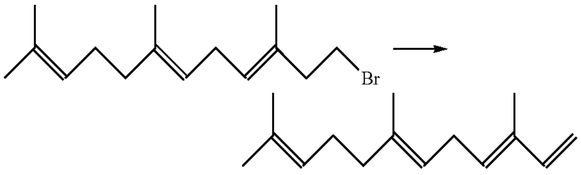

A mixture of (6E,9E)-12-bromo-2,6,10-trimethyl-2,6,9-dodecatriene (1.00 g, 92.0% GC, 80.9% EE-α) synthesized in the aforesaid Example 20, 1,5-diazabicyclo[4.3.0]-5-nonene (DBN; 655 mg), 2,6-di-t-butyl-p-cresol (BHT; 20 mg), and dimethylformamide (16 ml) was stirred in a nitrogen atmosphere for 19 hours at a room temperature. Water was added to the reaction mixture, and the reaction mixture was extracted with n-hexane. The n-hexane solution was subjected to ordinary work-up, i.e., washing, drying, and concentration to obtain a crude product (440 mg) of the target compound, (3E,6E)-α-farnesene. This crude product was purified with a crude product obtained in the Example below.

Example 37: Synthesis (2) of (3E,6E)-α-farnesene (When R=(E)-3,7-dimethyl-2,6-octadienyl Group, and Geometrical Isomerism of Double Bond of Position 3 is E-Form in general Formula (A))

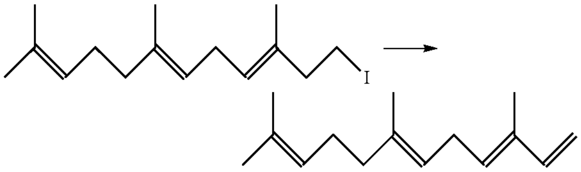

A mixture of (6E,9E)-12-iodo-2,6,10-trimethyl-2,6,9-dodecatriene (230 mg, 77.8% GC, 66.7% EE-α,) synthesized in the aforesaid Example 24, 1,5-diazabicyclo[4.3.0]-5-nonene (DBN; 130 mg), 2,6-di-t-butyl-p-cresol (BHT; 20 mg), and dimethylformamide (4 ml) was stirred in a nitrogen atmosphere for 15 hours at a room temperature. Water was added to the reaction mixture, and the reaction mixture was extracted with diethyl ether. The diethyl ether solution was subjected to ordinary work-up, i.e., washing, drying, and concentration to obtain a crude product (170 mg) of the target compound, (3E,6E)-α-farnesene. This crude product, with the crude product obtained in the previous Example (above), was purified by silica gel column chromatography to obtain the target compound, (3E,6E)-α-farnesene (380 mg, 80.6% NMR, yield 46%).

Detailed spectral analysis showed that this compound was a 80.6:12.1:7.3 isomeric mixture of target compound, (3E, 6E)-α-farnesene:E-β-isomer, (Z)-p-farnesene:(3E,6E)-3,7, 11-trimethyl-1,3,6,11-dodecatetraene having the double bond of position 10 rearranged to position 11.

(3E,6E)-α-Farnesene

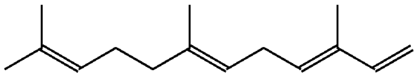

$C_{15}H_{24}$

Colorless Oil

IR (D-ATR): ν=3089, 2968, 2925, 2856, 1640, 1442, 1377, 988, 892 $cm^{-1}$.

$^1$H-NMR (500 MHz, $CDCl_3$): δ=1.60 (3H, s-like), 1.64 (3H, s-like), 1.68 (3H, q-like, J=1.1 Hz), 1.76 (3H, q-like, J=1.1 Hz), 1.96-2.02 (2H, m), 2.04-2.11 (2H, m), 2.83 (2H, t, J=7.3 Hz), 4.93 (1H, d, J=10.7 Hz), 5.08-5.16 (2H, m), 5.09 (1H, dd, J=17.4, 0.6 Hz), 5.46 (1H, t-like, J=7.3 Hz), 6.37 (1H, dd, J=17.4, 10.7 Hz) ppm.

$^{13}$C-NMR (125 MHz, $CDCl_3$): δ=11.65, 16.10, 17.68, 25.69, 26.64, 27.21, 39.64, 110.53, 122.00, 124.21, 131.43, 131.86, 133.70, 135.77, 141.52 ppm.

GC-MS (EI, 70 eV): 41, 55, 67, 79, 93 (base peak), 107, 119, 133, 147, 161, 175, 189, 204 ($M^+$).

Example 38: Synthesis of (3Z,6E)-α-farnesene (When R=(E)-3,7-dimethyl-2,6-octadienyl Group, and Geometrical Isomerism of Double Bond of Position 3 is Z-Form in General Formula (A))

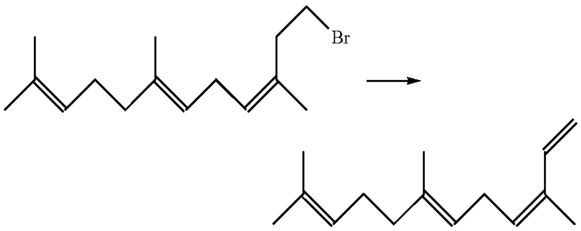

A mixture of (6E,9Z)-12-bromo-2,6,10-trimethyl-2,6,9-dodecatriene (1.15 g, 80.6% GC) synthesized in the aforesaid Example 21, 1,5-diazabicyclo[4.3.0]-5-nonene (DBN; 728 mg), 2,6-di-t-butyl-p-cresol (BHT; 20 mg), and dimethylformamide (13 ml) was stirred in a nitrogen atmosphere for 16 hours at a room temperature. Water was added to the reaction mixture, and the reaction mixture was extracted with n-hexane. The n-hexane solution was subjected to ordinary work-up, i.e., washing, drying, and concentration, and then purified by silica gel column chromatography to obtain the target compound, (3Z,6E)-α-farnesene (560 mg, 81.3% NMR, yield 85%).

(3Z,6E)-α-Farnesene

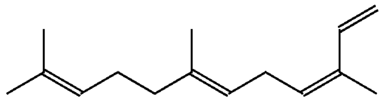

$C_{15}H_{24}$

Colorless Oil

IR (D-ATR): ν=3090, 2969, 2926, 2857, 1644, 1441, 1377, 987, 901 $cm^{-1}$.

$^1$H-NMR (500 MHz, $CDCl_3$): δ=1.60 (3H, s-like), 1.64 (3H, s-like), 1.68 (3H, q-like, J=1.2 Hz), 1.82 (3H, q-like, J=1.2 Hz), 1.94-2.02 (2H, m), 2.02-2.13 (2H, m), 2.87 (2H, t, J=7.4 Hz), 5.06-5.16 (3H, m), 5.20 (1H, d-like, J=17.2 Hz), 5.36 (1H, t-like, J=7.4 Hz), 6.81 (1H, ddd, J=17.2, 10.9, 1.0 Hz) ppm.

$^{13}$C-NMR (125 MHz, $CDCl_3$): δ=16.08, 17.67, 19.74, 25.68, 26.33, 26.64, 39.63, 113.46, 122.33, 124.22, 129.73, 131.41, 131.89, 133.64, 135.65 ppm.

GC-MS (EI, 70 eV): 41, 55, 67, 79, 93 (base peak), 107, 119, 135, 147, 161, 175, 189, 204 ($M^+$).

Example 39: Synthesis of (3E,6Z)-α-farnesene (When R=(Z)-3,7-dimethyl-2,6-octadienyl Group, and Geometrical Isomerism of Double Bond of Position 3 is E-Form in General Formula (A))

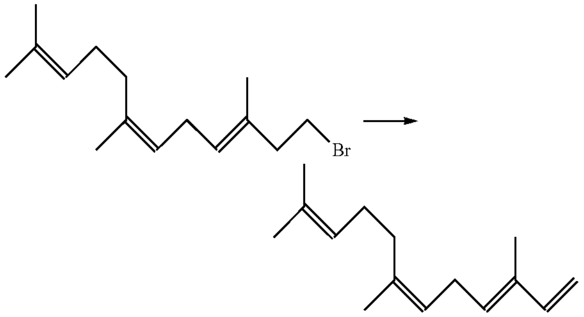

A mixture of (6Z,9E)-12-bromo-2,6,10-trimethyl-2,6,9-dodecatriene (760 mg, 83.0% GC) synthesized in the aforesaid Example 22, 1,5-diazabicyclo[4.3.0]-5-nonene (DBN; 520 mg), 2,6-di-t-butyl-p-cresol (BHT; 20 mg), and dimethylformamide (8 ml) was stirred in a nitrogen atmosphere for 23 hours at a room temperature. Water was added to the reaction mixture, and the reaction mixture was extracted with n-hexane. The n-hexane solution was subjected to ordinary work-up, i.e., washing, drying, and concentration, and then purified by silica gel column chromatography to obtain the target compound, (3E,6Z)-α-farnesene (210 mg, 85.4% NMR, yield 93%).

Detailed spectral analysis showed that this compound was a 85.4:6.8:7.8 isomeric mixture of target compound, (3E, 6Z)-α-farnesene:Z-β-isomer, (Z)-β-farnesene:(3E,6Z)-3,7, 11-trimethyl-1,3,6,11-dodecatetraene having the double bond of position 10 rearranged to position 11.

(3E,6Z)-α-Farnesene

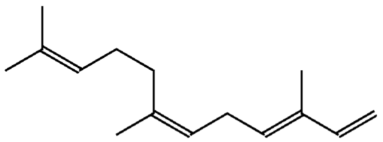

$C_{15}H_{24}$

IR (D-ATR): ν=3089, 2967, 2927, 2857, 1791, 1640, 1447, 1376, 988, 892 $cm^{-1}$.

$^1$H-NMR (500 MHz, $CDCl_3$): δ=1.62 (3H, q-like, J=~1 Hz), 1.69 (3H, s-like), 1.70 (3H, q-like, J=~1 Hz), 1.76 (3H, q-like, J=~1 Hz), 2.02-2.12 (4H, m), 2.84 (2H, t-like, J=7.3 Hz), 4.93 (1H, d, J=10.7 Hz), 5.09 (1H, d-like, J=17.4 Hz), 5.08-5.18 (2H, m), 5.44 (1H, t-like, J=7.4 Hz), 6.37 (1H, dd, J=17.4, 10.8) ppm.

$^{13}$C-NMR (125 MHz, $CDCl_3$): δ=11.64, 17.63, 23.36, 25.72, 26.52, 27.08, 31.98, 110.55, 122.77, 124.17, 131.67, 131.90, 133.63, 135.95, 141.52 ppm.

GC-MS (EI, 70 eV): 41, 55, 69, 81, 93 (base peak), 107, 119, 133, 147, 161, 175, 189, 204 ($M^+$).

Example 40: Synthesis (1) of (3Z,6Z)-α-farnesene (When R=(Z)-3,7-dimethyl-2,6-octadienyl Group, and Geometrical Isomerism of Double Bond of Position 3 is Z-Form in General Formula (A))

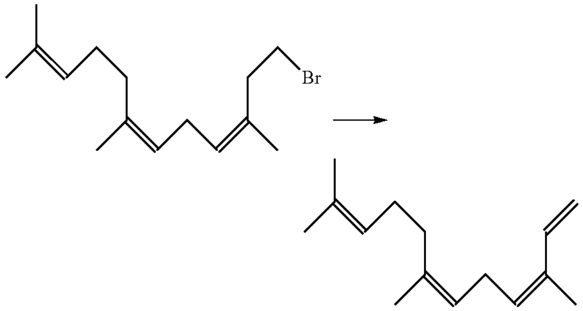

A mixture of (6Z,9Z)-12-bromo-2,6,10-trimethyl-2,6,9-dodecatriene (1.82 g, 88.3% GC) synthesized in the aforesaid Example 23, 1,5-diazabicyclo[4.3.0]-5-nonene (DBN; 1.144 g), 2,6-di-t-butyl-p-cresol (BHT; 20 mg), and dimethylformamide (20 ml) was stirred in a nitrogen atmosphere for 22 hours at a room temperature. Water was added to the reaction mixture, and the reaction mixture was extracted with n-hexane. The n-hexane solution was subjected to ordinary work-up, i.e., washing, drying, and concentration, and then purified by silica gel column chromatography to obtain the target compound, (3Z,6Z)-α-farnesene (913 mg, 93% NMR, yield 84%).

(3Z,6Z)-α-Farnesene

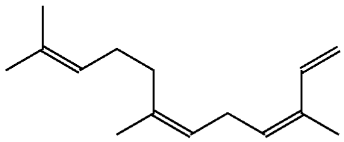

$C_{15}H_{24}$

IR (D-ATR): ν=3090, 2968, 2927, 2857, 1808, 1643, 1441, 1376, 986, 833 cm-1.

$^1$H-NMR (500 MHz, $CDCl_3$): δ=1.62 (3H, q-like, J=~1 Hz), 1.68-1.72 (3H, m), 1.69 (3H, s-like), 1.81 (3H, q-like, J=~1 Hz), 2.05-2.14 (4H, m), 2.87 (2H, t-like, J=7.4 Hz), 5.06-5.17 (3H, m), 5.20 (1H, d-like, J=17.2 Hz), 5.34 (1H, t-like, J=7.4 Hz), 6.80 (1H, ddd, J=17.4, 10.8, 0.9 Hz) ppm.

$^{13}$C-NMR (125 MHz, $CDCl_3$): δ=17.63, 19.75, 23.37, 25.71, 26.21, 26.53, 31.96, 113.50, 123.11, 124.19, 129.79, 131.66, 131.90, 133.60, 135.83 ppm.

GC-MS (EI, 70 eV): 41, 55, 69, 81, 93 (base peak), 107, 119, 133, 147, 161, 175, 189, 204 ($M^+$).

This target compound was sealed in a sample tube with nitrogen after adding BHT as a stabilizer, and stored in a refrigerator at −20° C. for three years and one month, after which $^{1}$H-NMR spectra of the sample showed that purity of the initial synthesis had been maintained. It was found that the target compound synthesized by the preparation process of the present invention withstood long-term storage and did not decompose in a short period of time as described in some literatures.

Example 41: Synthesis (2) of (3Z,6Z)-α-farnesene (When R=(Z)-3,7-dimethyl-2,6-octadienyl Group, and Geometrical Isomerism of Double Bond of Position 3 is Z-Form in General Formula (A))

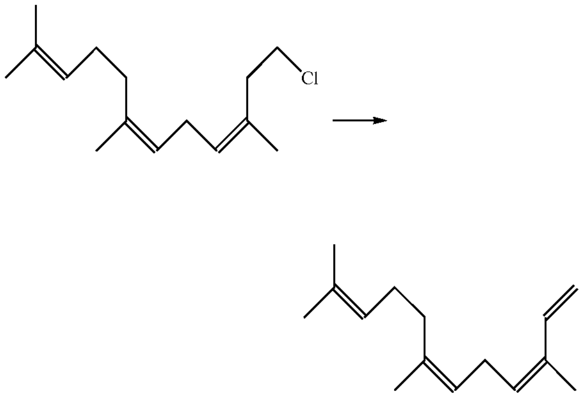

A mixture of (6Z,9Z)-12-chloro-2,6,10-trimethyl-2,6,9-dodecatriene (700 mg, ~94.8% GC) synthesized in the aforesaid Example 19, 1,8-diazabicyclo[5.4.0]-7-undecene (DBU; 2.22 g), and 2,6-di-t-butyl-p-cresol (BHT; 20 mg) was stirred in a nitrogen atmosphere for 2 hours at 60 to 80° C. DBU (2.22 g) was then added to the reaction mixture, and the reaction mixture was stirred for 1.5 hours at 80° C. The reaction mixture was poured into 10% hydrochloric acid and extracted with diethyl ether. The diethyl ether solution was subjected to ordinary work-up, i.e., washing, drying, and concentration, and then purified by silica gel column chromatography to obtain the target compound, (3Z,6Z)-α-farnesene, in amounts of 120 mg (60.0% GC, isomer purity 70.6%) and 0.27 g (43.8% GC, isomer purity ~40.0%) (yield 41% for only target isomer, isomer total yield 86%).

Detailed spectral analysis showed that this compound was an isomeric mixture of the target compound, (3Z,6Z)-α-farnesene, an isomer (2E,4E,6Z)-3,7,11-trimethyl-2,4,6,10-dodecatetraene having a conjugated triene structure in which two double bonds of positions 1 and 3 were rearranged to positions 2 and 4, and an isomer (3Z,5E)-3,7,11-trimethyl-1,3,5,10-dodecatetraene having a conjugated triene structure in which a double bond of position 6 was rearranged to position 5. It was shown that in the elimination step of the hydrogen halide, HX, under extreme conditions of intense heat in a basic condition using a chloride intermediate, wherein X=Cl, a side reaction may occur in which a double bond of the target compound was rearranged to the conjugated side.

(2E,4E,6Z)-3,7,11-Trimethyl-2,4,6,10-dodecatetraene

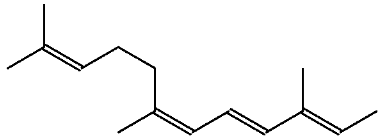

$C_{15}H_{24}$

GC-MS (EI, 70 eV): 41, 55, 77, 93, 107 (base peak), 119, 135, 147, 161, 175, 189, 204 ($M^+$).

A 2D-NOESY (NOE: nuclear Overhauser effect) correlation was observed between signals of hydrogen atoms bonded to carbon atoms at the positions shown by the bidirectional arrows in the following chemical formula:

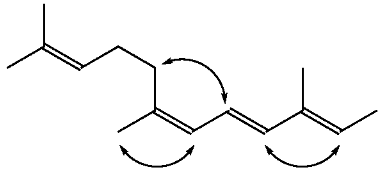

(3Z,5E)-3,7,11-Trimethyl-1,3,5,10-dodecatetraene

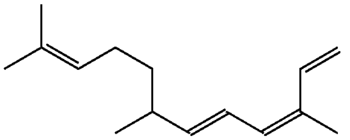

=

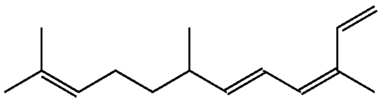

$C_{15}H_{24}$

GC-MS (EI, 70 eV): 41, 55, 77, 93, 107 (base peak), 119, 135, 148, 161, 175, 189, 204 ($M^+$).

A 2D-NOESY (NOE: nuclear Overhauser effect) correlation was observed between signals of hydrogen atoms bonded to carbon atoms at the positions shown by the bidirectional arrows in the following chemical formula:

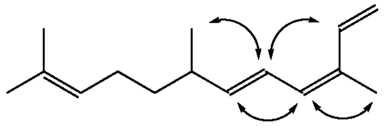

Example 42: Synthesis (3) of (3Z,6Z)-α-farnesene (When R=(Z)-3,7-dimethyl-2,6-octadienyl Group, and Geometrical Isomerism of Double Bond of Position 3 is Z-Form in General Formula (A))

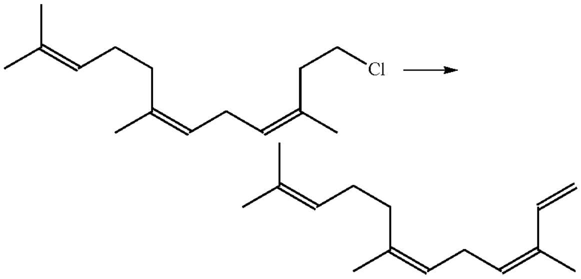

A mixture of (6Z,9Z)-12-chloro-2,6,10-trimethyl-2,6,9-dodecatriene (700 mg, ~89.5% GC) synthesized by a process similar to the aforesaid Example 19, 1,5-diazabicyclo [4.3.0]-5-nonene (DBN; 1.00 g), 2,6-di-t-butyl-p-cresol (BHT; 5 mg), and toluene (7.2 ml) was stirred in a nitrogen atmosphere for 5 hours at 70 to 80° C. DBN (1.00 g) was then added to the reaction mixture, and the reaction mixture was stirred for 5 hours at 60° C. Dimethylformamide (DMF; 10 ml) was added to the reaction mixture, and the reaction mixture was stirred for 5 hours at 60 to 80° C. The reaction mixture was poured into 2% sulfuric acid and extracted with n-hexane. The n-hexane solution was subjected to ordinary work-up, i.e., washing, drying, and concentration to obtain the target compound, (3Z,6Z)-α-farnesene (180 mg, ~95% NMR, crude yield 66%).

Example 43: Synthesis (4) of (3Z,6Z)-α-farnesene (When R=(Z)-3,7-dimethyl-2,6-octadienyl Group, and Geometrical Isomerism of Double Bond of Position 3 is Z-Form in General Formula (A))

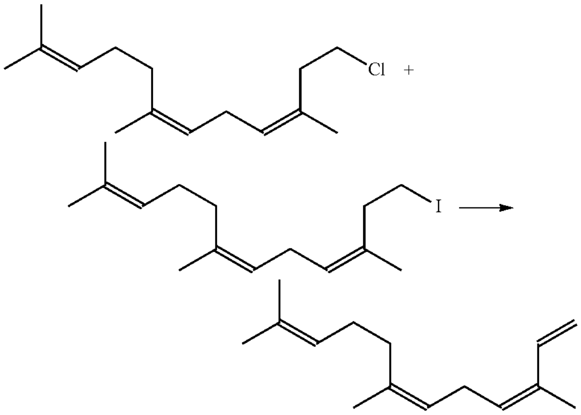

A mixture including a 68.6:31.4 mixture of (6Z,9Z)-12-chloro-2,6,10-trimethyl-2,6,9-dodecatriene:(6Z,9Z)-(12-iodo-2,6,10-trimethyl-2,6,9-dodecatriene synthesized in the aforesaid Example 25, 1,5-diazabicyclo[4.3.0]-5-nonene (DBN; 260 mg), 2,6-di-t-butyl-p-cresol (BHT; 5 mg), and dimethylformamide (DMF; 10 ml) was stirred in a nitrogen atmosphere for 6 hours while heating to increase the internal temperature from 40° C. to 80° C. DBN (260 mg) was then added, and the reaction mixture was stirred for 5 hours at 80 to 85° C. The reaction mixture was cooled, then poured into 2% sulfuric acid, and then extracted with n-hexane. The n-hexane solution was subjected to ordinary work-up, i.e., washing, drying, and concentration to obtain the target compound, (3Z,6Z)-α-farnesene (90 mg, $\sim_{90}$% NMR, quantitative crude yield).

Example 44: Synthesis of (E)-β-ocimene (When R=3-methyl-2-butenyl Group, and Geometrical Isomerism of Double Bond of Position 3 is E-Form in General Formula (A))

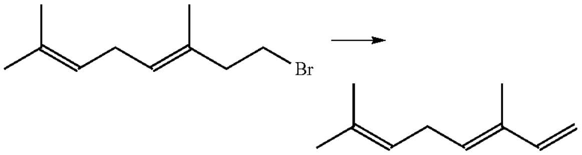

A mixture of crude (E)-8-bromo-2,6-dimethyl-2,5-octadienene (1.24 g, 80.7% GC) synthesized in the aforesaid Example 28, 1,5-diazabicyclo[4.3.0]-5-nonene (DBN; 1.04 g), 2,6-di-t-butyl-p-cresol (BHT; 40 mg), and dimethylformamide (DMF; 20 ml) was stirred in a nitrogen atmosphere for 23 hours at a room temperature. The reaction mixture was poured into 2% sulfuric acid, and then extracted with n-pentane. The n-pentane solution was subjected to ordinary work-up, i.e., washing, drying, and concentration, and then purified by silica gel column chromatography to obtain the target compound, (E)-β-ocimene (78.7% GC, yield 55%).

(E)-β-Ocimene

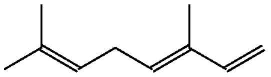

$C_{10}H_{16}$

Colorless Oil

IR (D-ATR): ν=3090, 3006, 2972, 2926, 2858, 1791, 1640, 1606, 1442, 1376, 1105, 1075, 989, 892, 866, 831 $cm^{-1}$.

$^{1}$H-NMR (500 MHz, $CDCl_3$): δ=1.64 (3H, s-like), 1.70 (3H, d-like, J=~1 Hz), 1.77 (3H, q-like, J=~1 Hz), 2.83 (2H, t, J=7.4 Hz), 4.93 (1H, d, J=10.9 Hz), 5.09 (1H, d-like, J=17.4 Hz), 5.10-5.15 (1H, m), 5.46 (1H, t-like, J=7.4 Hz), 6.38 (1H, dd, J=10.9, 17.4 Hz) ppm.

$^{13}$C-NMR (125 MHz, $CDCl_3$): δ=11.63, 17.73, 25.66, 27.31, 110.56, 122.16, 131.76, 132.16, 133.69, 141.51 ppm.

GC-MS (EI, 70 eV): 41, 53, 67, 79, 93 (base peak), 105, 121, 136 ($M^+$).

Example 45: Synthesis of (Z)-β-ocimene (When R=3-methyl-2-butenyl Group, and Geometrical Isomerism of Double Bond of Position 3 is Z-Form in General Formula (A))

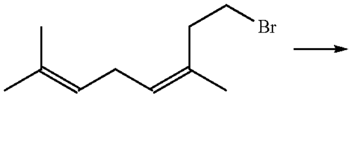

-continued

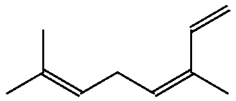

A mixture of (Z)-8-bromo-2,6-dimethyl-2,5-octadienene (300 mg, 73.0% GC) synthesized in the aforesaid Example 29, 1,5-diazabicyclo[4.3.0]-5-nonene (DBN; 250 mg), 2,6-di-t-butyl-p-cresol (BHT; 5 mg), and dimethylformamide (DMF; 5 ml) was stirred in a nitrogen atmosphere for 22 hours at a room temperature. The reaction mixture was poured into 2% sulfuric acid, and then extracted with n-pentane. The n-pentane solution was subjected to ordinary work-up, i.e., washing, drying, and concentration, and then purified by silica gel column chromatography to obtain the target compound, (E)-β-ocimene (110 mg, 73.6% GC, yield 59%).

(Z)-β-Ocimene

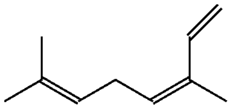

$C_{10}H_{16}$

Colorless Oil

IR (D-ATR): ν=3090, 2971, 2927, 2858, 1644, 1594, 1440, 1377, 1158, 1106, 987, 901, 860, 828 $cm^{-1}$.

$^1$H-NMR (500 MHz, $CDCl_3$): δ=1.64 (3H, s), 1.70 (3H, q-like, J=~1.2 Hz), 1.82 (3H, q-like, J=~1.2 Hz), 2.86 (2H, t-like, J=~7.2 Hz), 5.07-5.14 (2H, m), 5.22 (1H, d-like, J=~17 Hz), 5.35 (1H, t, J=7.6 Hz), 6.81 (1H, ddd, J=1.0, 10.9, ~17 Hz) ppm.

$^{13}$C-NMR (125 MHz, $CDCl_3$): δ=17.71, 19.73, 25.67, 26.45, 113.50, 122.49, 129.64, 131.94, 132.05, 133.61 ppm.

GC-MS (EI, 70 eV): 39, 53, 67, 79, 93 (base peak), 105, 121, 136 ($M^+$).

Example 46: Synthesis of (1E,4E)-5-methyl-1-phenyl-1,4,6-heptatriene (When R=(E)-cinnamyl Group, and Geometrical Isomerism of Double Bond of Position 4 is E-Form in General Formula (A))

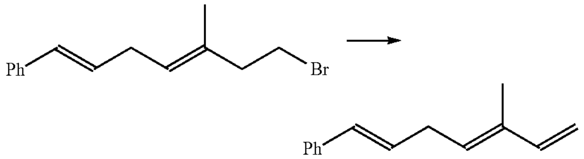

1,5-Diazabicyclo[4.3.0]-5-nonene (DBN; 260 mg) was added to a reaction mixture of (1E,4E)-7-bromo-5-methyl-1-phenyl-1,4-heptadiene synthesized in the aforesaid Example 31 and stirred in a nitrogen atmosphere for 70 minutes at 40° C. The reaction mixture was poured into 2% sulfuric acid, and then extracted with diethyl ether. The diethyl ether solution was subjected to ordinary work-up, i.e., washing, drying, and concentration, and then purified by silica gel column chromatography to try to obtain the target compound, (1E,4E)-5-methyl-1-phenyl-1,4,6-heptatriene. The target compound was extremely unstable, and within a short period of time during purification, completely isomerized to the following conjugated triene compound, (1E,3E,5E)-5-methyl-1-phenyl-1,3,5-heptatriene, having the double bonds of positions 4 and 6 rearranged to positions 3 and 5.

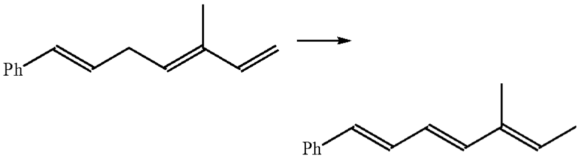

(1E,3E,5E)-5-Methyl-1-phenyl-1,3,5-heptatriene

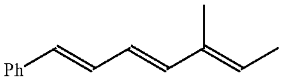

$C_{14}H_{16}$ $^1$H-NMR (500 MHz, $CDCl_3$): δ=1.78 (3H, d, J=7.3 Hz), 1.81 (3H, s-like), 5.65 (1H, q, J=7.2 Hz), 6.32 (1H, dd, J=15.3, 10.1 Hz), 6.39 (1H, d, J=15.3 Hz), 6.54 (1H, d, J=15.6), 6.84 (1H, dd, J=15.6, 10.1 Hz), 7.17-7.23 (1H, m), 7.27-7.34 (2H, m), 7.37-7.42 (2H, m) ppm.

GC-MS (EI, 70 eV): 39, 51, 65, 77, 91, 105, 128, 141, 154, 169 (base peak), 184 ($M^+$).

Example 47: Synthesis of (E)-3-methyl-1,3-dodecadiene (When R=n-octyl Group, and Geometrical Isomerism of Double Bond of Position 3 is E-Form in General Formula (A))

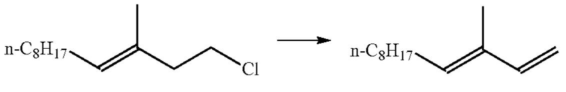

A mixture of potassium tert-butoxide (200 mg) and THE (2 ml) was poured into a mixture of (E)-1-chloro-3-methyl-3-dodecene (300 mg, 92.8% GC) synthesized in the aforesaid Example 32, 2,6-di-t-butyl-p-cresol (BHT; 5 mg), and tetrahydrofuran (THF; 3 ml) in a nitrogen atmosphere under ice cooling with stirring. Potassium tert-butoxide (200 mg) was added to the reaction mixture while returning the reaction mixture to a room temperature with stirring. The reaction mixture was then stirred for 3 hours. The reaction mixture was poured into dilute hydrochloric acid, and then extracted with diethyl ether. The diethyl ether solution was subjected to ordinary work-up, i.e., washing, drying, and concentration, and then purified by silica gel column chromatography to obtain the target compound, (E)-3-methyl-1,3-dodecadiene (252 mg, 92.7% GC, yield 93%).

(E)-3-Methyl-1,3-dodecadiene

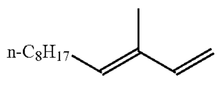

$C_{13}H_{24}$

Colorless Oil

IR (D-ATR): ν=3090, 2956, 2925, 2855, 1643, 1467, 1388, 1378, 1083, 988, 891, 721 $cm^{-1}$.

$^{1}$H-NMR (500 MHz, $CDCl_3$): δ=0.88 (3H, t, J=7.0 Hz), 1.22-1.41 (12H, m), 1.73 (3H, s-like), 2.12 (2H, q-like, J=7.4 Hz), 4.92 (1H, d, J=10.7 Hz), 5.08 (1H, d-like, J=17.2 Hz), 5.49 (1H, t, J=7.2 Hz), 6.37 (1H, ddd, J=17.3, 10.7, 0.6 Hz) ppm.

$^{13}$C-NMR (125 MHz, $CDCl_3$): δ=11.62, 14.10, 22.67, 28.22, 29.29, 29.38, 29.50 (2C), 31.88, 110.24, 133.62, 133.78, 141.68 ppm.

GC-MS (EI, 70 eV): 41, 55, 68 (base peak), 81, 95, 109, 123, 137, 151, 165, 180 (M).

Example 48: Synthesis of (Z)-3-methyl-1,3-dodecadiene (When R=n-octyl Group, and Geometrical Isomerism of Double Bond of Position 3 is Z-Form in General Formula (A))

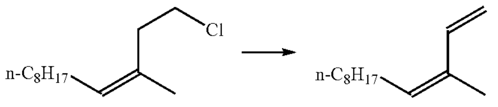

A mixture of (Z)-1-chloro-3-methyl-3-dodecene (300 mg, 99.6% GC) synthesized in the aforesaid Example 33, 2,6-di-t-butyl-p-cresol (BHT; 10 mg), 1,8-diazabicyclo[5.4.0]-7-undecene (DBU; 395 mg), and dimethylformamide (DMF; 3 ml) was stirred in a nitrogen atmosphere for 1 hour at 50° C., and then for 2.5 hours at 85 to 90° C. DBU (520 mg) was then added, and the reaction mixture was stirred for 10 hours at 90° C. The reaction mixture was cooled, then poured into dilute hydrochloric acid, and then extracted with diethyl ether. The diethyl ether solution was subjected to ordinary work-up, i.e., washing, drying, and concentration, and then purified by silica gel column chromatography to obtain the target compound, (Z)-3-methyl-1,3-dodecadiene (250 mg, ~100% GC, quantitative yield).

(Z)-3-Methyl-1,3-dodecadiene

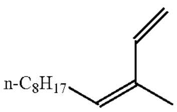

$C_{13}H_{24}$

Colorless Oil

IR (D-ATR): ν=3090, 2957, 2925, 2855, 1645, 1461, 1378, 1082, 987, 900, 721 $cm^{-1}$.

$^{1}$H-NMR (500 MHz, $CDCl_3$): δ=0.89 (3H, t, J=7.0 Hz), 1.22-1.40 (12H, m), 1.81 (3H, dd, J=2.4, 1.1 Hz), 2.15 (2H, q-like, J=~7.4 Hz), 5.07 (1H, dt, J=1.7, 10.7 Hz), 5.17 (1H, d-like, J=17.4 Hz), 5.39 (1H, t, J=7.7 Hz), 6.78 (1H, ddd, J=17.4, 10.7, 0.9 Hz) ppm.

$^{13}$C-NMR (125 MHz, $CDCl_3$): δ=14.10, 19.76, 22.66, 27.34, 29.28, 29.32, 29.49, 29.87, 31.88, 113.07, 131.63, 132.02, 133.80 ppm.

GC-MS (EI, 70 eV): 41, 55, 68 (base peak), 81, 95, 109, 123, 137, 151, 165, 180 ($M^+$).

Example 49: Synthesis of (E)-α-ocimene (When R=3-methyl-3-butenyl Group, and Geometrical Isomerism of Double Bond of Position 3 is E-Form in General Formula (A))

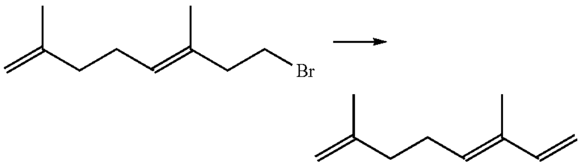

A mixture of crude (E)-8-bromo-2,6-dimethyl-1,5-octadienene (820 mg, 68.5% GC) synthesized in the aforesaid Example 35, 1,5-diazabicyclo[4.3.0]-5-nonene (DBN; 645 mg), 2,6-di-t-butyl-p-cresol (BHT; 40 mg), and dimethylformamide (DMF; 15 ml) was stirred in a nitrogen atmosphere for 20 hours at a room temperature. The reaction mixture was poured into 2% sulfuric acid, and then extracted with n-pentane. The n-pentane solution was subjected to ordinary work-up, i.e., washing, drying, and concentration, and then purified by silica gel column chromatography to obtain the target compound, (E)-α-ocimene (270 mg, 75.6% GC, yield 58%).

(E)-α-Ocimene

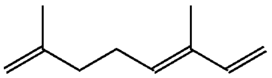

$C_{10}H_{16}$

Colorless Oil

IR (D-ATR): ν=3088, 3005, 2970, 2933, 2858, 1649, 1607, 1444, 1388, 1375, 1087, 989, 890 $cm^{-1}$.

$^{1}$H-NMR (500 MHz, $CDCl_3$): δ=1.73 (3H, s-like), 1.75 (3H, s-like), 2.09 (2H, t-like, J=~7.8 Hz), 2.28 (2H, q-like, J=7.8 Hz), 4.69-4.71 (1H, m), 4.72-4.74 (1H, m), 4.93 (1H, d-like, J=10.7 Hz), 5.09 (1H, d-like, J=17 Hz), 5.49 (1H, t-like, J=~7 Hz), 6.37 (1H, dd, J=11.0, 17.3 Hz) ppm.

$^{13}$C-NMR (125 MHz, $CDCl_3$): δ=11.67, 22.44, 26.42, 37.33, 110.09, 110.51, 132.58, 134.08, 141.49, 145.39 ppm.

GC-MS (EI, 70 eV): 27, 39, 53, 65, 81 (base peak), 93, 107, 121, 136 ($M^+$).

Synthetic Examples: Synthesis of 4-Substituted Primary Allylsulfonediene Compound (C) of the Following General Formula (C)

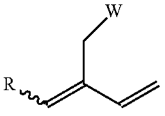

Synthetic Example 3: Synthesis (1) of (3E/Z,6Z)-(7,11-dimethyl-1,3,6,10-dodecatetraen-3-yl)methyl p-tolyl sulfone (When R=(Z)-3,7-dimethyl-2,6-octadienyl Group, and Geometrical Isomerism of Double Bond of Position 3 is E/Z Mixture in General Formula (C))

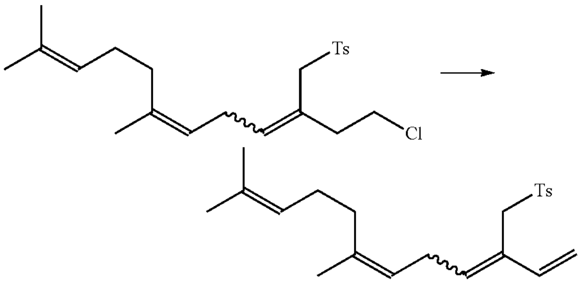

Potassium tert-butoxide (175 mg) was added to a mixture including a 76.9:23.1 ($^1$H-NMR) mixture (530 mg) of (3E, 6Z)-(1-chloro-7,11-dimethyl-3,6,10-dodecatrien-3-yl) methyl p-tolyl sulfone:(3Z,6Z)-(1-chloro-7,11-dimethyl-3, 6,10-dodecatrien-3-yl)methyl p-tolyl sulfone synthesized by a process similar to the aforesaid Example 9, 2,6-di-t-butyl-p-cresol (BHT; 80 mg), and tetrahydrofuran (THF; 15 ml) in a nitrogen atmosphere under ice cooling with stirring. The reaction mixture was stirred for 18 hours at a room temperature. GC analysis of the reaction mixture showed that the target HCl elimination reaction was accompanied by undesired elimination of p-toluenesulphinate, resulting in a complex mixture.

Synthetic Example 4: Synthesis (2) of (3E/Z,6Z)-(7,11-dimethyl-1,3,6,10-dodecatetraen-3-yl)methyl p-tolyl sulfone (When R=(Z)-3,7-dimethyl-2,6-octadienyl Group, and Geometrical Isomerism of Double Bond of Position 3 is E/Z Mixture in General Formula (C))

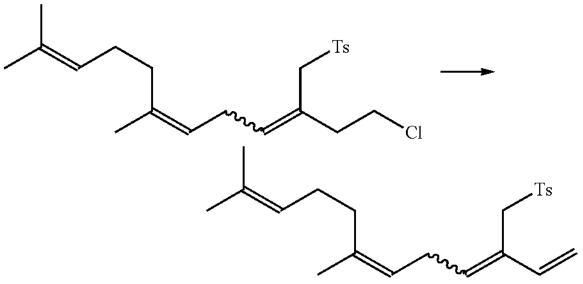

1,8-Diazabicyclo[5.4.0]-7-undecene (DBU; 480 mg) was added to a mixture including a 76.9:23.1 ($^1$H-NMR) mixture (250 mg) of (3E,6Z)-(1-chloro-7,11-dimethyl-3,6,10-dodecatrien-3-yl)methyl p-tolyl sulfone:(3Z,6Z)-(1-chloro-7,11-dimethyl-3,6,10-dodecatrien-3-yl)methyl p-tolyl sulfone synthesized by a process similar to the aforesaid Example 9, 2,6-di-t-butyl-p-cresol (BHT; 80 mg), and toluene (2 ml) in a nitrogen atmosphere at a room temperature with stirring. The reaction mixture was stirred for 1.5 hours at a room temperature, and then for 3 hours at 40° C. Toluene (4 ml) was then added, and the reaction mixture was stirred for 5 hours at 60° C. GC analysis of the reaction mixture showed that the starting material remained, and the target HCl elimination reaction had a conversion of 15%, and so isolation/purification of the target compound was not carried out.

Synthetic Example 5: Synthesis of (3Z,6E)-(7,11-dimethyl-1,3,6,10-dodecatetraen-3-yl)methyl phenyl sulfone (When R=(E)-3,7-dimethyl-2,6-octadienyl Group, and Geometrical Isomerism of Double Bond of Position 3 is Z-Form in General Formula (C))

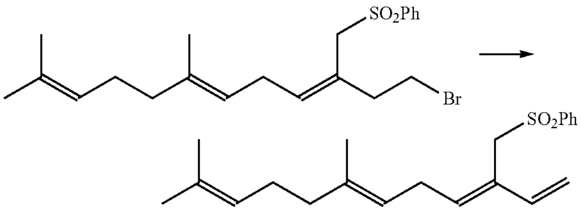

A mixture of (3Z,6E)-(1-bromo-7,11-dimethyl-3,6,10-dodecatrien-3-yl)methyl phenyl sulfone (180 mg, ~93% NMR) synthesized in the aforesaid Example 10, 2,6-di-t-butyl-p-cresol (BHT; 20 mg), 1,5-diazabicyclo[4.3.0]-5-nonene (DBN; 52 mg), and dimethylformamide (DMF; 2 ml) was stirred in a nitrogen atmosphere for 11 hours at a room temperature. The reaction proceeded slowly, and so 1,8-diazabicyclo[5.4.0]-7-undecene (DBU; 520 mg) was added to the reaction mixture, and the reaction mixture was stirred for 5 hours at 50° C. GC analysis of the reaction mixture showed that although the target compound was formed, many by-products including $C_{33}H_{44}$ hydrocarbons were formed instead of the target compound, and so isolation/purification of the target compound was not carried out.

(3Z,6E)-(7,11-dimethyl-1,3,6,10-dodecatetraen-3-yl) methyl phenyl sulfone

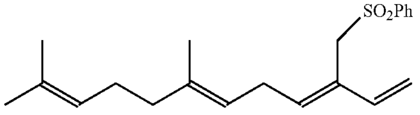

GC-MS (EI, 70 eV): 41,77,105,133 (base peak), 159, 203, 275, 344 ($M^+$).

The Examples above and the Synthetic Examples illustrated as Comparative Examples above demonstrate that among the synthetic routes from the primary allylsulfone compound (D) to the 4-substituted 3-methyl-1,3-butadiene compound (A), the process (I) via the halide compound (B), specifically, (I)-(1) reductive removal of the arenesulfonyl group, W, of the allyl position of the primary allylsulfone compound (D) to form the halide compound (B), and (I)-(2) elimination of the hydrogen halide, HX, of the halide compound (B) to obtain the target compound, 4-alkyl-3-methyl-1,3-butadiene compound (A):

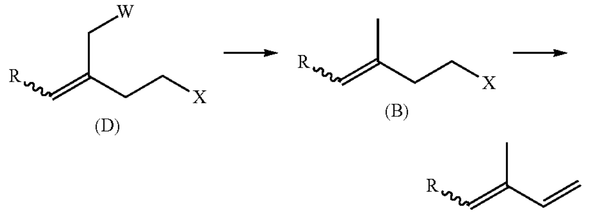

(D) (B) (A)

was preferred compared to the process (II) via the primary allylsulfonediene compound (C), specifically, (II)-(1) elimination of the hydrogen halide, HX, from the primary allylsulfone compound (D) to form the primary allylsulfonediene compound (C), and (II)-(2) reductive removal of the arenesulfonyl group, W, of the primary allylsulfonediene compound (C) to obtain the target compound, 4-substituted 3-methyl-1,3-butadiene compound (A):

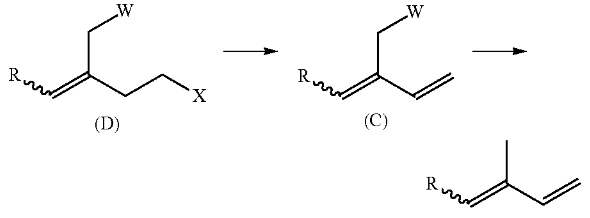

(D) (C) (A)

The invention claimed is:

1. A process for preparing a 4-substituted 3-methyl-1,3-butadiene compound of the following general formula (A):

(A)

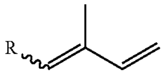

wherein R represents a linear, branched, or cyclic hydrocarbon group having 1 to 20 carbon atoms and optionally having an unsaturated bond(s), the process comprising the steps of:

subjecting a primary allylsulfone compound of the following general formula (D):

(D)

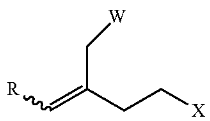

wherein R represents a linear, branched, or cyclic hydrocarbon group having 1 to 20 carbon atoms and optionally having an unsaturated bond(s), X represents a halogen atom, and W represents an arenesulfonyl group, to a reductive removal of the arenesulfonyl group, W, to form a halide compound of the following general formula (B):

(B)

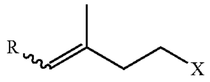

wherein R represents a linear, branched, or cyclic hydrocarbon group having 1 to 20 carbon atoms and optionally having an unsaturated bond(s), and X represents a halogen atom; and subjecting the aforesaid halide compound (B) to an elimination reaction of a hydrogen halide, HX, to form the aforesaid 4-substituted 3-methyl-1,3-butadiene compound (A).

2. A primary allylsulfone compound of the following general formula (D):

(D)

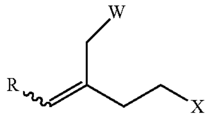

wherein R represents a linear, branched, or cyclic hydrocarbon group having 1 to 20 carbon atoms and optionally having an unsaturated bond(s), X represents a halogen atom, and W represents an arenesulfonyl group.

3. A process for preparing a primary allylsulfone compound of the following general formula (D):

(D)

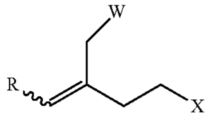

wherein R represents a linear, branched, or cyclic hydrocarbon group having 1 to 20 carbon atoms and optionally having an unsaturated bond(s), X represents a halogen atom, and W represents an arenesulfonyl group, the process comprising a step of:

subjecting a secondary allylsulfone compound of the following general formula (E):

(E)

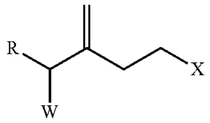

wherein R represents a linear, branched, or cyclic hydrocarbon group having 1 to 20 carbon atoms and optionally having an unsaturated bond(s), X represents a halogen atom, and W represents an arenesulfonyl group, to an allylic rearrangement reaction of the arenesulfonyl group, W, to form the aforesaid primary allylsulfone compound (D).

4. The process for preparing a 4-substituted 3-methyl-1,3-butadiene compound (A) according to claim 1, wherein R represents 3,7-dimethyl-2,6-octadienyl group or a 3-methyl-2-butenyl group.

5. The primary allylsulfone compound (D) according to claim 2, wherein R represents 3,7-dimethyl-2,6-octadienyl group or a 3-methyl-2-butenyl group.

* * * * *